United States Patent
Rubin et al.

(10) Patent No.: US 11,692,179 B2
(45) Date of Patent: Jul. 4, 2023

(54) COMPOSITIONS AND METHODS INVOLVING ENGINEERED P27

(71) Applicant: THE REGENTS OF THE UNIVERSITY OF CALIFORNIA, Santa Cruz, CA (US)

(72) Inventors: Seth Rubin, Santa Cruz, CA (US); Keelan Guiley, Santa Cruz, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 129 days.

(21) Appl. No.: 16/977,441

(22) PCT Filed: Apr. 10, 2019

(86) PCT No.: PCT/US2019/026845
§ 371 (c)(1),
(2) Date: Sep. 1, 2020

(87) PCT Pub. No.: WO2019/209538
PCT Pub. Date: Oct. 31, 2019

(65) Prior Publication Data
US 2021/0002619 A1    Jan. 7, 2021

Related U.S. Application Data

(60) Provisional application No. 62/663,914, filed on Apr. 27, 2018.

(51) Int. Cl.
*C12N 9/12* (2006.01)
*C07K 14/47* (2006.01)
*C12Q 1/48* (2006.01)

(52) U.S. Cl.
CPC ............ *C12N 9/12* (2013.01); *C07K 14/4738* (2013.01); *C12Q 1/485* (2013.01); *C12Y 207/11022* (2013.01); *G01N 2440/14* (2013.01); *G01N 2500/02* (2013.01)

(58) Field of Classification Search
CPC ...... C12N 9/12; C07K 14/4738; C07K 19/00; C12Q 1/485; C12Y 207/11022; G01N 2440/14; G01N 2500/02
See application file for complete search history.

(56) References Cited

U.S. PATENT DOCUMENTS

2002/0068706 A1    6/2002    Gyuris et al.

FOREIGN PATENT DOCUMENTS

WO    2005040207 A1    5/2005

OTHER PUBLICATIONS

UniProt Acc#A0A091J2M2 Zhang, 2014. Alignment with SID1.*
James et al, Differential Modification of p27Kip1 Controls Its Cyclin D-cdk4 Inhibitory Activity. Molecular and Cellular Biology, Jan. 2008, p. 498-510.*
NCBI Acc# NP_004055 orignally disclosed by Bullrich et al, Chromosomal mapping of members of the cdc2 family of protein kinases, cdk3, cdk6, PISSLRE, and PITALRE, and a cdk inhibitor, p27Kip1, to regions involved in human cancer Cancer Res 55 (6), 1199-1205 (1995). Alignment with SID1.*
NCBI BLAST search results with SID1. Performed Jul. 12, 2022.*
Sadowski et al., The sequence-structure relationship and protein function prediction. Current Opinion in Structural Biology, 2009, vol. 19: 357-362. (Year: 2009).*
Seffernick et al., Melamine deaminase and Atrazine chlorohydrolase: 98 percent identical but functionally different. J. Bacteriol., 2001, vol. 183 (8): 2405-2410. (Year: 2001).*
Tang et al., Identification of Dehalobacter reductive dehydrogenases that catalyse dechlorination of chloroform, 1,1,1-trichloroethane and 1,1-dichloroethane. Phil Trans R Soc B, 2013, vol. 368: Mar. 18, 2012, pp. 1-10. (Year: 2013).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
PCT/US2019/026845, "International Preliminary Report on Patentability", dated Nov. 5, 2020, 8 pages.
Altschul et al., "Basic Local Alignment Search Tool", Journal of Molecular Biology, vol. 215, No. 3, Oct. 5, 1990, pp. 403-410.
Altschul et al., "Gapped BLAST and PSI-BLAST: A New Generation of Protein Database Search Programs", Nucleic Acids Research, vol. 25, No. 17, Sep. 1, 1997, pp. 3389-3402.
Bagui et al., "P27Kip1 and p21Cip1 are not required for the formation of active D cyclin-cdk4 complexes", Molecular and Cellular Biology vol. 23, No. 20, 2003, pp. 7285-7290.
Bagui et al., "Analysis of cyclin D3-cdk4 complexes in fibroblasts expressing and lacking p27 Kip1 and p21 Cip1", Molecular and cellular biology vol. 20, No. 23, 2000, 8748-8757.
Cheng et al., "The p21Cip1 and p27Kip1 CDK 'inhibitors' are essential activators of cyclin D-dependent kinases in murine fibroblasts", The EMBO journal vol. 18, No. 6, 1999, pp. 1571-1583.
Dick et al., "Molecular mechanisms underlying RB protein function", Nature reviews Molecular cell biology vol. 14, No. 5, 2013, pp. 297-306.
Dickler et al., "MONARCH 1, a phase II study of abemaciclib, a CDK4 and CDK6 inhibitor, as a single agent, in patients with refractory HR+/HER2—metastatic breast cancer", Clinical Cancer Research 23.17, 2017, pp. 5218-5224.
Dyson, "RB1: a prototype tumor suppressor and an enigma", Genes & Development vol. 30 No. 13, 2016, pp. 1492-1502.
Finn et al., "Palbociclib and letrozole in advanced breast cancer", New England Journal of Medicine vol. 375, No. 20, 2016, pp. 1925-1936.
Grimmler et al., "Cdk-inhibitory activity and stability of p27Kip1 are directly regulated by oncogenic tyrosine kinases", Cell vol. 128, No. 2, 2007, pp. 269-280.
Hampl et al., "Levels and Interactions of p27, Cyclin D3, and CDK4 during the Formation and Maintenance of the Corpus Luteum in Mice", Biology of Reproduction, vol. 62, No. 5, 2000, pp. 1393-1401.

(Continued)

*Primary Examiner* — Ganapathirama Raghu
(74) *Attorney, Agent, or Firm* — Kilpatrick Townsend & Stockton LLP

(57) ABSTRACT

The disclosure provides polypeptides comprising an engineered p27, or a fragment thereof. Such polypeptides may be used to form trimeric protein complexes with a cyclin-dependent kinase 4 (Cdk4) (or a variant thereof) or Cdk6 (or a variant thereof), and a cyclin D (CycD) or a variant thereof.

3 Claims, 3 Drawing Sheets

Specification includes a Sequence Listing.

(56) References Cited

OTHER PUBLICATIONS

He et al., "Transient CDK4/6 inhibition protects hematopoietic stem cells from chemotherapy-induced exhaustion", Science translational medicine vol. 9, No. 387, 2017, 27 pages.
James et al., "Differential modification of p27Kip1 controls its cyclin D-cdk4 inhibitory activity", Molecular and Cellular Biology vol. 28, No. 1, 2008, pp. 498-510.
Kato et al., "Inactivation of the cyclin D-dependent kinase in the rat fibroblast cell line, 3Y1, induced by contact inhibition", Journal of Biological Chemistry vol. 272, No. 12, 1997, pp. 8065-8070.
Labaer et al., "New functional activities for the p21 family of CDK inhibitors", Genes & Development vol. 11, No. 7, 1997, pp. 847-862.
Ladha et al., "Regulation of exit from quiescence by p27 and cyclin D1-CDK4", Molecular and cellular biology vol. 18, No. 11, 1998, pp. 6605-6615.
Parry et al., "Cyclin D-CDK subunit arrangement is dependent on the availability of competing INK4 and p21 class inhibitors", Molecular and Cellular Biology vol. 19, No. 3, 1999, pp. 1775-1783.
Patel et al., "Brk/Protein Tyrosine Kinase 6 Phosphorylates p27KIP1, Regulating the Activity of Cyclin D-Cyclin-Dependent Kinase 4", Molecular and Cellular Biology vol. 35, No. 9, 2015, pp. 1506-1522.
PCT/US2019/026845, International Search Report and Written Opinion, dated Jul. 15, 2019, 11 pages.
Qu et al., "Regulation of the Mammalian Cell Cycle: A model of the G1-to-S Transition", American Journal of Physiology: Cell Physiology, vol. 284, No. 2, 2002, pp. C349-C364.
Ray et al., "p27Kip1 Inhibits Cyclin D-Cyclin-Dependent Kinase 4 by Two Independent Modes", Molecular Cell Biology, vol. 29, No. 4, Feb. 2009, pp. 986-999.
Sherr et al., "Targeting CDK4 and CDK6: from discovery to therapy", Cancer discovery vol. 6, No. 4, 2016, pp. 353-367.
Xu et al., "Recent advances of highly selective CDK4/6 inhibitors in breast cancer", Journal of Hematology & Oncology vol. 10, No. 1, 2017, pp. 1-12.

* cited by examiner

| | Cdk4-Cyclin D1 | | Cdk4-Cyclin D1-p27(EEE) | |
|---|---|---|---|---|
| | $K_M$ (μM) | $V_{max}$ (μM/min) | $K_M$ (μM) | $V_{max}$ (μM/min) |
| Rb 771-928 | 1.0 ± 0.6 | 1.6 ± 0.1 | 0.04 ± 0.02 | 0.22 ± 0.05 |
| FoxM1 | 3 ± 2 | 0.2 ± 0.1 | 0.03 ± 0.02 | 0.4 ± 0.2 |
| Histone H1 | no detectable activity | | 0.12 ± 0.02 | 0.26 ± 0.03 |

COMPOSITIONS AND METHODS INVOLVING ENGINEERED P27

CROSS-REFERENCES TO RELATED APPLICATIONS

This application is a National Stage of International Application No. PCT/US2019/026845, filed Apr. 10, 2019, which claims priority to U.S. Provisional Application No. 62/663,914, filed Apr. 27, 2018, the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support under Grant Nos. CA132685 and CA206244, awarded by the National Institutes of Health. The government has certain rights in this invention.

BACKGROUND

Cyclin-dependent kinases (Cdk) 4 and 6 promote cell proliferation through their kinase activity. Inhibitors of Cdk4 and Cdk6 may function as cancer therapeutics. The active cellular form of the enzyme Cdk4 or Cdk6 is in complex with cyclin D (CycD) and p27. Current inhibitors of Cdk4/6 were developed using Cdk4-CycD dimeric complexes that lack p27, in part because of the technical challenges in generating the active form of p27. However, the Cdk4-CycD dimeric complex does not readily form in all cells. Further, certain complexes including p27 may be resistant to treatments.

SUMMARY

In one aspect, the disclosure features a polypeptide comprising an engineered p27, or a fragment thereof, wherein the engineered p27 has at least one amino acid substitution at a position selected from the group consisting of Y74, Y88, and Y89, wherein the engineered p27 forms a trimeric protein complex with (i) a cyclin-dependent kinase 4 (Cdk4) or a variant thereof, or a Cdk6 or a variant thereof, and (ii) a cyclin D (CycD) or a variant thereof, and wherein the amino acid positions are determined with reference to the sequence of SEQ ID NO: 1.

In some embodiments, the engineered p27 comprises amino acid substitution Y74E or Y74D. In some embodiments, the engineered p27 comprises amino acid substitution Y74E, Y74D, or Y74R. In some embodiments, the engineered p27 comprises amino acid substitution Y88E or Y88D. In some embodiments, the engineered p27 comprises amino acid substitution Y89E or Y89D.

In some embodiments of this aspect, the engineered p27 comprises a sequence having at least 90% sequence identity to the sequence of SEQ ID NO: 1.

In some embodiments of this aspect, the engineered p27 comprises a sequence of KPSACRNLFGPVDHEELT RDLEKHCRDMEEASQRKWNFDFQNHKPLEGKX$_1$E WQEVEKGSLPEFX$_2$X$_3$RPPRPPKGA (SEQ ID NO: 59), wherein X$_1$ is Y, E, D, or R; X$_2$ is Y, E, or D; and X$_3$ is Y, E, or D, and wherein at least one of X$_1$, X$_2$, and X$_3$ is not Y. In some embodiments, X$_1$ is Y. In some embodiments, X$_1$ is E. In some embodiments, X$_1$ is D. In some embodiments, X$_1$ is R. In some embodiments, X$_2$ is Y. In some embodiments, X$_2$ is E. In some embodiments, X$_2$ is D. In some embodiments, X$_3$ is Y. In some embodiments, X$_3$ is E. In some embodiments, X$_3$ is D.

In some embodiments of this aspect, the engineered p27 comprises a sequence having at least 90% sequence identity to the sequence of (SEQ ID NO: 6)
KPSACRNLFGPVDHEELTRDLEKHCRDMEEASQRKWNFDFQNHKPLEGKE

EWQEVEKGSLPEFYYRPPRPPKGA or (SEQ ID NO: 4)
MSNVRVSNGSPSLERMDARQAEHPKPSACRNLFGPVDHEELTRDLEKHCR

DMEEASQRKWNFDFQNHKPLEGKEEWQEVEKGSLPEFYYRPPRPPKGACK

VPAQESQDVSGSRPAAPLIGAPANSEDTHLVDPKTDPSDSQTGLAEQCAG

IRKRPATDDSSTQNKRANRTEENVSDGSPNAGSVEQTPKKPGLRRRQT.

In some embodiments of this aspect, the engineered p27 comprises a sequence having at least 90% sequence identity to the sequence of (SEQ ID NO: 12)
KPSACRNLFGPVDHEELTRDLEKHCRDMEEASQRKWNFDFQNHKPLEGK

REWQEVEKGSLPEFYYRPPRPPKGA or (SEQ ID NO: 10)
MSNVRVSNGSPSLERMDARQAEHPKPSACRNLFGPVDHEELTRDLEKHC

RDMEEASQRKWNFDFQNHKPLEGKREWQEVEKGSLPEFYYRPPRPPKGA

CKVPAQESQDVSGSRPAAPLIGAPANSEDTHLVDPKTDPSDSQTGLAEQ

CAGIRKRPATDDSSTQNKRANRTEENVSDGSPNAGSVEQTPKKPGLRRR

QT.

In some embodiments of this aspect, the engineered p27 comprises a sequence having at least 90% sequence identity to the sequence of (SEQ ID NO: 15)
KPSACRNLFGPVDHEELTRDLEKHCRDMEEASQRKWNFDFQNHKPLEGKY

EWQEVEKGSLPEFEYRPPRPPKGA or (SEQ ID NO: 13)
MSNVRVSNGSPSLERMDARQAEHPKPSACRNLFGPVDHEELTRDLEKHCR

DMEEASQRKWNFDFQNHKPLEGKYEWQEVEKGSLPEFYRPPRPPKGACK

VPAQESQDVSGSRPAAPLIGAPANSEDTHLVDPKTDPSDSQTGLAEQCAG

IRKRPATDDSSTQNKRANRTEENVSDGSPNAGSVEQTPKKPGLRRRQT.

In some embodiments of this aspect, the engineered p27 comprises a sequence having at least 90% sequence identity to the sequence of (SEQ ID NO: 21)
KPSACRNLFGPVDHEELTRDLEKHCRDMEEASQRKWNFDFQNHKPLEGKY

EWQEVEKGSLPEFYERPPRPPKGA or (SEQ ID NO: 19)
MSNVRVSNGSPSLERMDARQAEHPKPSACRNLFGPVDHEELTRDLEKHCR

DMEEASQRKWNFDFQNHKPLEGKYEWQEVEKGSLPEFYERPPRPPKGACK

-continued

VPAQESQDVSGSRPAAPLIGAPANSEDTHLVDPKTDPSDSQTGLAEQCAG

IRKRPATDDSSTQNKRANRTEENVSDGSPNAGSVEQTPKKPGLRRRQT.

In some embodiments of this aspect, the engineered p27 comprises a sequence having at least 90% sequence identity to the sequence of (SEQ ID NO: 27)
KPSACRNLFGPVDHEELTRDLEKHCRDMEEASQRKWNFDFQNHKPLEGKE EWQEVEKGSLPEFEYRPPRPPKGA
or (SEQ ID NO: 25)
MSNVRVSNGSPSLERMDARQAEHPKPSACRNLFGPVDHEELTRDLEKHCR

DMEEASQRKWNFDFQNHKPLEGKEEWQEVEKGSLPEFEYRPPRPPKGACK

VPAQESQDVSGSRPAAPLIGAPANSEDTHLVDPKTDPSDSQTGLAEQCAG

IRKRPATDDSSTQNKRANRTEENVSDGSPNAGSVEQTPKKPGLRRRQT.

In some embodiments of this aspect, the engineered p27 comprises a sequence having at least 90% sequence identity to the sequence of (SEQ ID NO: 30)
KPSACRNLFGPVDHEELTRDLEKHCRDMEEASQRKWNFDFQNHKPLEGK EEWQEVEKGSLPEFYERPPRPPKGA
or (SEQ ID NO: 28)
MSNVRVSNGSPSLERMDARQAEHPKPSACRNLFGPVDHEELTRDLEKHC

RDMEEASQRKWNFDFQNHKPLEGKEEWQEVEKGSLPEFYERPPRPPKGA

CKVPAQESQDVSGSRPAAPLIGAPANSEDTHLVDPKTDPSDSQTGLAEQ

CAGIRKRPATDDSSTQNKRANRTEENVSDGSPNAGSVEQTPKKPGLRRR

QT.

In some embodiments of this aspect, the engineered p27 comprises a sequence having at least 90% sequence identity to the sequence of (SEQ ID NO: 33)
KPSACRNLFGPVDHEELTRDLEKHCRDMEEASQRKWNFDFQNHKPLEGK YEWQEVEKGSLPEFEERPPRPPKGA
or (SEQ ID NO: 31)
MSNVRVSNGSPSLERMDARQAEHPKPSACRNLFGPVDHEELTRDLEKHC

RDMEEASQRKWNFDFQNHKPLEGKYEWQEVEKGSLPEFEERPPRPPKGA

CKVPAQESQDVSGSRPAAPLIGAPANSEDTHLVDPKTDPSDSQTGLAEQ

CAGIRKRPATDDSSTQNKRANRTEENVSDGSPNAGSVEQTPKKPGLRRR

QT.

In some embodiments of this aspect, the engineered p27 comprises a sequence having at least 90% sequence identity to the sequence of (SEQ ID NO: 36)
KPSACRNLFGPVDHEELTRDLEKHCRDMEEASQRKWNFDFQNHKPLEGKE EWQEVEKGSLPEFEERPPRPPKGA
or (SEQ ID NO: 34)
MSNVRVSNGSPSLERMDARQAEHPKPSACRNLFGPVDHEELTRDLEKHCR

DMEEASQRKWNFDFQNHKPLEGKEEWQEVEKGSLPEFEERPPRPPKGACK

VPAQESQDVSGSRPAAPLIGAPANSEDTHLVDPKTDPSDSQTGLAEQCAG

IRKRPATDDSSTQNKRANRTEENVSDGSPNAGSVEQTPKKPGLRRRQT.

In another aspect, the disclosure features a trimeric protein complex comprising: (i) a polypeptide comprising an engineered p27 as described in the previous aspect, or a phosphorylated, wild-type p27 or a fragment thereof; (ii) a Cdk4 or a variant thereof, or a Cdk6 or a variant thereof; and (iii) a CycD or a variant thereof, wherein the Cdk4 or the variant thereof or the Cdk6 or the variant thereof in the trimeric protein complex is an active kinase.

In some embodiments of this aspect, the Cdk4 or the variant thereof or the Cdk6 or the variant thereof is capable of phosphorylating a protein comprising a phosphorylation site having the sequence $X_1PX_2X_3$ (SEQ ID NO: 60), wherein $X_1$ is S or T; $X_2$ is any amino acid; and $X_3$ is K or R. In some embodiments, the protein comprising the phosphorylation site is retinoblastoma protein (Rb), FoxM1, or histone H1.

In some embodiments of this aspect, the CycD is CycD1, CycD2, CycD3, or a variant thereof.

In some embodiments of this aspect, the CycD1 or the variant thereof comprises a sequence having at least 90% sequence identity to the sequence of (SEQ ID NO: 55)
MEHQLLCCEVETIRRAYPDANLLNDRVLRAMLKAEETCAPSVSYFKCVQK

EVLPSMRKIVATWMLEVCEEQKCEEEVFPLAMNYLDRFLSLEPVKKSRLQ

LLGATCMFVASKMKETIPLTAEKLCIYTDNSIRPEELLQMELLLVNKLKW

NLAAMTPHDFIEHFLSKMPEAEENKQIIRKHAQTFVALCATDVKFISNPP

SMVAAGSVVAAVQGLNLRSPNNFLSYYRLTRFLSRVIKCDPDCLRACQEQ

IEALLESSLRQAQQNMDPKAAEEEEEEEEVDLACTPTDVRDVDI,
or (SEQ ID NO: 56)
DANLLNDRVLRAMLKAEETCAPSVSYFKCVQKEVLPSMRKIVATWMLEVC

EEQKCEEEVFPLAMNYLDRFLSLEPVKKSRLQLLGATCMFVASKMKETIP

LTAEKLCIYTDNSIRPEELLQMELLLVNKLKWNLAAMTPHDFIEHFLSKM

PEAEENKQIIRKHAQTFVALCATDVKFISNPPSMVAAGSVVAAVQGLNLR

SPNNFLSYYRLTRFLSRVIKCDPDCLRACQEQIEALLESSLRQAQQNMD.

In some embodiments of this aspect, the CycD2 comprises a sequence having at least 90% sequence identity to the sequence of (SEQ ID NO: 57)
MELLCHEVDPVRRAVRDRNLLRDDRVLQNLLTIEERYLPQCSYFKCVQKD

IQPYMRRMVATWMLEVCEEQKCEEEVFPLAMNYLDRFLAGVPTPKSHLQL

LGAVCMFLASKLKETSPLTAEKLCIYTDNSIKPQELLEWELVVLGKLKWN

LAAVTPHDFIEHILRKLPQQREKLSLIRKHAQTFIALCATDFKFAMYPPS

MIATGSVGAAICGLQQDEEVSSLTCDALTELLAKITNTDVDCLKACQEQI

EAVLLNSLQQYRQDQRDGSKSEDELDQASTPTDVRDIDL.

In some embodiments of this aspect, the CycD3 comprises a sequence having at least 90% sequence identity to the sequence of (SEQ ID NO: 58)
MELLCCEGTRHAPRAGPDPRLLGDQRVLQSLLRLEERYVPRASYFQCVQR

EIKPHMRKMLAYWMLEVCEEQRCEEEVFPLAMNYLDRYLSCVPTRKAQLQ

LLGAVCMLLASKLRETTPLTIEKLCIYTDHAVSPRQLRDWEVLVLGKLKW

DLAAVIAHDFLAFILHRLSLPRDRQALVKKHAQTFLALCATDYTFAMYPP

SMIATGSIGAAVQGLGACSMSGDELTELLAGITGTEVDCLRACQEQIEAA

LRESLREASQTSSSPAPKAPRGSSSQGPSQTSTPTDVTAIHL.

In some embodiments of this aspect, the Cdk4 or a variant thereof comprises a sequence having at least 90% sequence identity to the sequence of (SEQ ID NO: 37)
MATSRYEPVAEIGVGAYGTVYKARDPHSGHFVALKSVRVPNGGGGGGGLP

ISTVREVALLRRLEAFEHPNVVRLMDVCATSRTDREIKVTLVFEHVDQDL

RTYLDKAPPPGLPAETIKDLMRQFLRGLDFLHANCIVHRDLKPENILVTS

GGTVKLADFGLARIYSYQMALTPVVVTLWYRAPEVLLQSTYATPVDMWSV

GCIFAEMFRRKPLFCGNSEADQLGKIFDLIGLPPEDDWPRDVSLPRGAFP

PRGPRPVQSVVPEMEESGAQLLLEMLTFNPHKRISAFRALQHSYLHKDEG

NPE.

In some embodiments of this aspect, the variant of Cdk4 comprises T172E or T172D, and the amino acid positions are determined with reference to the sequence of SEQ ID NO: 37. In some embodiments, the variant of Cdk4 comprises a sequence having at least 90% sequence identity to the sequence of (SEQ ID NO: 39)
MATSRYEPVAEIGVGAYGTVYKARDPHSGHFVALKSVRVPNGGGGGGGLP

ISTVREVALLRRLEAFEHPNVVRLMDVCATSRTDREIKVTLVFEHVDQDL

RTYLDKAPPPGLPAETIKDLMRQFLRGLDFLHANCIVHRDLKPENILVTS

GGTVKLADFGLARIYSYQMALEPVVVTLWYRAPEVLLQSTYATPVDMWSV

GCIFAEMFRRKPLFCGNSEADQLGKIFDLIGLPPEDDWPRDVSLPRGAFP

PRGPRPVQSVVPEMEESGAQLLLEMLTFNPHKRISAFRALQHSYLHKDEG

NPE,
or (SEQ ID NO: 38)
MATSRYEPVAEIGVGAYGTVYKARDPHSGHFVALKSVRVPNGGGGGGGLP

ISTVREVALLRRLEAFEHPNVVRLMDVCATSRTDREIKVTLVFEHVDQDL

RTYLDKAPPPGLPAETIKDLMRQFLRGLDFLHANCIVHRDLKPENILVTS

GGTVKLADFGLARIYSYQMALDPVVVTLWYRAPEVLLQSTYATPVDMWSV

GCIFAEMFRRKPLFCGNSEADQLGKIFDLIGLPPEDDWPRDVSLPRGAFP

PRGPRPVQSVVPEMEESGAQLLLEMLTFNPHKRISAFRALQHSYLHKDEG

NPE.

In some embodiments of this aspect, the variant of Cdk4 has amino acid residues 44 to 46 deleted, G43E or G43D, and G47E or G47D, and the amino acid positions are determined with reference to the sequence of SEQ ID NO: 37. In some embodiments, the variant of Cdk4 comprises a sequence having at least 90% sequence identity to the sequence of (SEQ ID NO: 42)
MATSRYEPVAEIGVGAYGTVYKARDPHSGHFVALKSVRVPNGEDGLPIST

VREVALLRRLEAFEHPNVVRLMDVCATSRTDREIKVTLVFEHVDQDLRTY

LDKAPPPGLPAETIKDLMRQFLRGLDFLHANCIVHRDLKPENILVTSGGT

VKLADFGLARIYSYQMALTPVVVTLWYRAPEVLLQSTYATPVDMWSVGCI

FAEMFRRKPLFCGNSEADQLGKIFDLIGLPPEDDWPRDVSLPRGAFPPRG

PRPVQSVVPEMEESGAQLLLEMLTFNPHKRISAFRALQHSYLHKDEGNP

E, (SEQ ID NO: 41)
MATSRYEPVAEIGVGAYGTVYKARDPHSGHFVALKSVRVPNGDEGLPISTV

REVALLRRLEAFEHPNVVRLMDVCATSRTDREIKVTLVFEHVDQDLRTYLD

KAPPPGLPAETIKDLMRQFLRGLDFLHANCIVHRDLKPENILVTSGGTVKL

ADFGLARIYSYQMALTPVVVTLWYRAPEVLLQSTYATPVDMWSVGCIFAEM

FRRKPLFCGNSEADQLGKIFDLIGLPPEDDWPRDVSLPRGAFPPRGPRPVQ

SVVPEMEESGAQLLLEMLTFNPHKRISAFRALQHSYLHKDEGNPE, (SEQ ID NO: 40)
MATSRYEPVAEIGVGAYGTVYKARDPHSGHFVALKSVRVPNGEEGLPISTV

REVALLRRLEAFEHPNVVRLMDVCATSRTDREIKVTLVFEHVDQDLRTYLD

KAPPPGLPAETIKDLMRQFLRGLDFLHANCIVHRDLKPENILVTSGGTVKL

ADFGLARIYSYQMALTPVVVTLWYRAPEVLLQSTYATPVDMWSVGCIFAEM

FRRKPLFCGNSEADQLGKIFDLIGLPPEDDWPRDVSLPRGAFPPRGPRPVQ

SVVPEMEESGAQLLLEMLTFNPHKRISAFRALQHSYLHKDEGNPE,
or (SEQ ID NO: 43)
MATSRYEPVAEIGVGAYGTVYKARDPHSGHFVALKSVRVPNGDDGLPISTV

REVALLRRLEAFEHPNVVRLMDVCATSRTDREIKVTLVFEHVDQDLRTYLD

KAPPPGLPAETIKDLMRQFLRGLDFLHANCIVHRDLKPENILVTSGGTVKL

ADFGLARIYSYQMALTPVVVTLWYRAPEVLLQSTYATPVDMWSVGCIFAEM

FRRKPLFCGNSEADQLGKIFDLIGLPPEDDWPRDVSLPRGAFPPRGPRPVQ

SVVPEMEESGAQLLLEMLTFNPHKRISAFRALQHSYLHKDEGNPE.

In some embodiments of this aspect, the variant of Cdk4 has amino acid residues 44 to 46 deleted, G43E or G43D, G47E or G47D, and T172E or T172D, wherein the amino acid positions are determined with reference to the sequence of SEQ ID NO: 37. In some embodiments, the variant of Cdk4 comprises a sequence having at least 90% sequence identity to the sequence of (SEQ ID NO: 48)
MATSRYEPVAEIGVGAYGTVYKARDPHSGHFVALKSVRVPNGEEGLPIST
VREVALLRRLEAFEHPNVVRLMDVCATSRTDREIKVTLVFEHVDQDLRTY
LDKAPPPGLPAETIKDLMRQFLRGLDFLHANCIVHRDLKPENILVTSGGT
VKLADFGLARIYSYQMALEPVVVTLWYRAPEVLLQSTYATPVDMWSVGCI
FAEMFRRKPLFCGNSEADQLGKIFDLIGLPPEDDWPRDVSLPRGAFPPRG
PRPVQSVVPEMEESGAQLLLEMLTFNPHKRISAFRALQHSYLHKDEGNP
E,
or (SEQ ID NO: 44)
MATSRYEPVAEIGVGAYGTVYKARDPHSGHFVALKSVRVPNGEEGLPIST
VREVALLRRLEAFEHPNVVRLMDVCATSRTDREIKVTLVFEHVDQDLRTY
LDKAPPPGLPAETIKDLMRQFLRGLDFLHANCIVHRDLKPENILVTSGGT
VKLADFGLARIYSYQMALDPVVVTLWYRAPEVLLQSTYATPVDMWSVGCI
FAEMFRRKPLFCGNSEADQLGKIFDLIGLPPEDDWPRDVSLPRGAFPPRG
PRPVQSVVPEMEESGAQLLLEMLTFNPHKRISAFRALQHSYLHKDEGNP
E.

In some embodiments of this aspect, the Cdk6 comprises a sequence having at least 90% sequence identity to the sequence of (SEQ ID NO: 52)
MEKDGLCRADQQYECVAEIGEGAYGKVFKARDLKNGGRFVALKRVRVQTG
EEGMPLSTIREVAVLRHLETFEHPNVVRLFDVCTVSRTDRETKLTLVFEH
VDQDLTTYLDKVPEPGVPTETIKDMMFQLLRGLDFLHSHRVVHRDLKPQN
ILVTSSGQIKLADFGLARIYSFQMALTSVVVTLWYRAPEVLLQSSYATPV
DLWSVGCIFAEMFRRKPLFRGSSDVDQLGKILDVIGLPGEEDWPRDVALP
RQAFHSKSAQPIEKFVTDIDELGKDLLLKCLTFNPAKRISAYSALSHPYF
QDLERCKENLDSHLPPSQNTSELNTA.

In some embodiments of this aspect, the variant of Cdk6 comprises T177E or T177D, wherein the amino acid positions are determined with reference to the sequence of SEQ ID NO: 52. In some embodiments, the variant of Cdk6 comprises a sequence having at least 90% sequence identity to the sequence of (SEQ ID NO: 54)
MEKDGLCRADQQYECVAEIGEGAYGKVFKARDLKNGGRFVALKRVRVQTG
EEGMPLSTIREVAVLRHLETFEHPNVVRLFDVCTVSRTDRETKLTLVFEH
VDQDLTTYLDKVPEPGVPTETIKDMMFQLLRGLDFLHSHRVVHRDLKPQN
ILVTSSGQIKLADFGLARIYSFQMALESVVVTLWYRAPEVLLQSSYATPV
DLWSVGCIFAEMFRRKPLFRGSSDVDQLGKILDVIGLPGEEDWPRDVALP
RQAFHSKSAQPIEKFVTDIDELGKDLLLKCLTFNPAKRISAYSALSHPYF
QDLERCKENLDSHLPPSQNTSELNTA,
or (SEQ ID NO: 53)
MEKDGLCRADQQYECVAEIGEGAYGKVFKARDLKNGGRFVALKRVRVQTG
EEGMPLSTIREVAVLRHLETFEHPNVVRLFDVCTVSRTDRETKLTLVFEH
VDQDLTTYLDKVPEPGVPTETIKDMMFQLLRGLDFLHSHRVVHRDLKPQN
ILVTSSGQIKLADFGLARIYSFQMALDSVVVTLWYRAPEVLLQSSYATPV
DLWSVGCIFAEMFRRKPLFRGSSDVDQLGKILDVIGLPGEEDWPRDVALP
RQAFHSKSAQPIEKFVTDIDELGKDLLLKCLTFNPAKRISAYSALSHPYF
QDLERCKENLDSHLPPSQNTSELNTA.

In some embodiments of this aspect, the phosphorylated, wild-type p27 or a fragment thereof comprises the sequence of any one of SEQ ID NOS: 1-3 and is phosphorylated at Y74, Y88, and/or Y89, in which the amino acid positions are determined with reference to the sequence of SEQ ID NO: 1.

In another aspect, the disclosure features a method of screening for inhibitors of a trimeric protein complex comprising an active Cdk4 or a variant thereof, or an active Cdk6 or a variant thereof, comprising: (a) providing a trimeric protein complex described in the previous aspect; (b) contacting the trimeric protein complex with a compound and a substrate of the Cdk4 or the variant thereof or the Cdk6 or the variant thereof and (c) determining the phosphorylation status of the substrate, wherein the compound is an inhibitor of the trimeric protein complex if the compound inhibits the phosphorylation activity of the Cdk4 or the variant thereof or the Cdk6 or the variant thereof.

In some embodiments of this aspect, the method further comprises, prior to step (a), phosphorylating a wild-type p27 or a fragment thereof by contacting the wild-type p27 with a kinase. In some embodiments, the kinase is selected from the group consisting of Brk kinase, Src kinase, and Abl kinase.

In some embodiments of this aspect, the method further comprises, after step (c), comparing the phosphorylation status of the substrate with the phosphorylation status of the substrate when the compound is not present.

In some embodiments of this aspect, the substrate comprises a phosphorylation site having the sequence $X_1PX_2X_3$ (SEQ ID NO: 60), wherein $X_1$ is S or T; $X_2$ is any amino acid; and $X_3$ is K or R. In some embodiments, the substrate comprising the phosphorylation site is Rb, FoxM1, histone H1, or a variant thereof.

In another aspect, the disclosure features a method of expressing and purifying a trimeric protein complex comprising (i) a phosphorylated, wild-type p27 or a fragment thereof (ii) a Cdk4 or a variant thereof or a Cdk6 or a variant thereof and (iii) a CycD or a variant thereof, the method comprising: (a) expressing the Cdk4 or the variant thereof or the Cdk6 or the variant thereof, and the CycD or the variant thereof in a first cell line, where the first cell line comprises one or more expression vectors configured to express the Cdk4 or the variant thereof or the Cdk6 or the variant thereof, and the CycD or the variant thereof; (b) expressing the wild-type p27 or the fragment thereof in a second cell line, where the second cell line comprises an expression vector configured to express the wild-type p27 or the fragment thereof; (c) purifying the Cdk4 or the variant thereof or the Cdk6 or the variant thereof, and the CycD or the variant thereof from the first cell line and the wild-type p27 or the fragment thereof from the second cell line; (d) phosphorylating the wild-type p27 or the fragment thereof obtained from step (c) with a kinase; and (e) combining the phosphorylated, wild-type p27 or the fragment thereof obtained from step (d) with the purified Cdk4 or the variant thereof or the purified Cdk6 or the variant thereof, and the CycD or the variant thereof obtained from step (c) under conditions that allow the formation of the trimeric protein complex, wherein the Cdk4 or the variant thereof or the Cdk6 or the variant thereof in the trimeric protein complex is an active kinase.

In some embodiments of this aspect, the expression vector is a baculovirus vector. In some embodiments, the first and/or second cell line is an insect cell line.

DETAILED DESCRIPTION OF THE EMBODIMENTS

I. Introduction

Figure 1A:
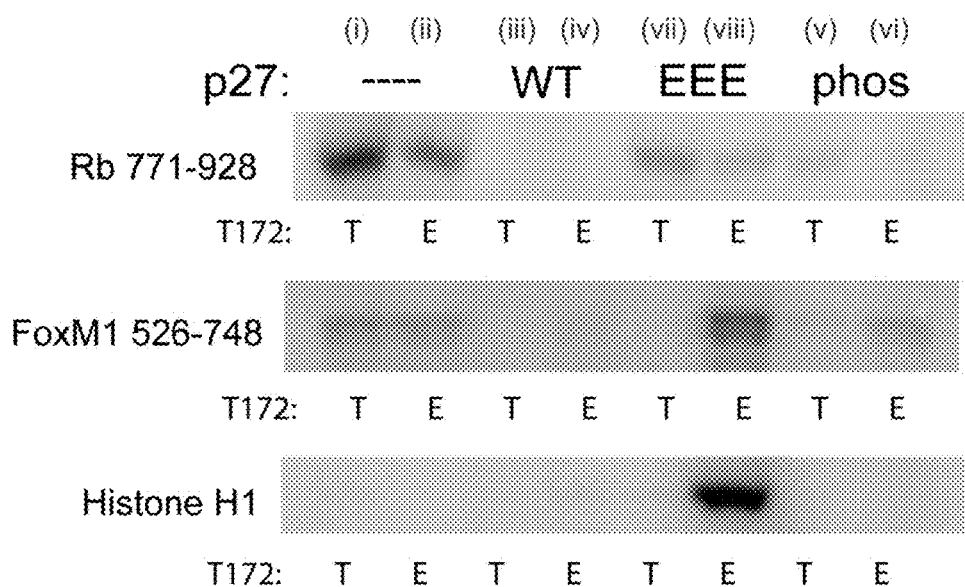
FIG. 1A shows $^{32}$P-ATP labeling of the indicated substrate with each of complexes (i)-(viii) as described in Example 3 (WT: wild-type, EEE: Y74E, Y88E, and Y89E substitutions in p27, phos: Brk-phosphorylated p27).

Genetic and biochemical studies have demonstrated that the retinoblastoma protein (Rb) pathway is a major regulator of cell cycle progression in G1 phase[1,2]. In G0/G1 phase, Rb and its family members p107 and p130 inhibit the E2F family of transcription factors (e.g., E2F1-5). In response to mitogenic signals, cyclin-dependent kinase (Cdk)-cyclin complexes phosphorylate Rb family members, which results in the disruption of complexes between Rb and E2F family members and allows the transcription of genes essential for S-phase progression. Cdk-cyclin complexes, e.g., Cdk4/6-CycD and Cdk2-CycE/A, are inhibited by proteins from the p16 family and can be either inhibited or activated by proteins from the p27 (p21, p27, p57) family.

With the goal of preventing Rb inactivation and cancer cell-cycle progression, specific inhibitors of Cdk4 and/or Cdk6 have been developed in the past decade. These inhibitors were found in screens against recombinant Cdk4-CycD dimeric complex. One of these inhibitors, palbociclib, was approved in 2015 for the treatment of estrogen receptor-positive breast cancer[3-5]. Several other Cdk4/6 inhibitors are being tested (e.g., ribociclib, abemaciclib, trilaciclib) in multiple cancer types[6-8]. Key unresolved challenges limiting Cdk4/6 inhibitors are, e.g., mechanisms of inherent resistance, acquired resistance, and early adaptation.

The activity of p27 (also known as cyclin-dependent kinase inhibitor 1B) towards Cdk4/6 is complex. p27 inhibits Cdk4/6-CycD activity in vitro and in cells under conditions of growth arrest[9-13]. At the same time, however, p27 increases Cdk4/6-CycD stability and is always present in active Cdk4/6-CycD complexes that phosphorylate Rb in proliferating cells[14-18]. Phosphorylation of p27 by tyrosine kinases (e.g., Src kinase, Brk kinase, Abl kinase) on amino acid residues Y74, Y88, and Y89 of p27 further increases Cdk4/6 activity, and this phosphorylation has been suggested to switch p27 from an inhibitor to an activator[19-21].

Disclosed herein are the structure and activity of the p27-Cdk4/6-CycD complex. Also disclosed is a method of expressing and purifying an active, recombinant p27-Cdk4/6-CycD complex.

In some embodiments, the method involves treating p27 with an active kinase (e.g., tyrosine kinase) such as recombinant Brk, Src, or Abl kinases. In some aspects of this embodiment, the p27 is treated prior to assembly of the enzyme. In other embodiments, the method involves using a p27 polypeptide that comprises a mutation at Y74, a mutation at Y88, and/or a mutation at Y89, or any combination thereof. In some aspects of this embodiment, the p27 polypeptide comprises a Y74E mutation and no mutation at Y88 or Y89. In other aspects, the p27 polypeptide comprises a Y88E mutation and a Y89E mutation In other aspects, the p27 polypeptide comprises a Y74R mutation, a Y88E mutation, and a Y89E mutation. It is disclosed herein that p27-activated Cdk4-CycD complex: (1) has broader substrate specificity than the Cdk4-CycD dimeric complex and (2) is resistant to treatment of palbociclib. For these reasons, the p27-Cdk4/6-CycD enzyme complex may be used for screening of new inhibitors that are effective in different cancer types.

II. Definitions

As used herein, the term "engineered p27" refers to a p27 polypeptide that contains one or more amino acid substitutions, additions, and/or deletions relative to the amino acid sequence of a wild-type p27 (e.g., SEQ ID NO: 1). An engineered p27 may have the same length as a wild-type p27 or may be a fragment of the wild-type p27. An engineered p27 as described herein may have at least one amino acid substitution at a position selected from the group consisting of Y74, Y88, and Y89, in which the amino acid positions are determined with reference to the sequence of SEQ ID NO: 1. Further, an engineered p27 as described herein forms a trimeric protein complex with a cyclin-dependent kinase 4 (Cdk4) or a variant thereof, or Cdk6 or a variant thereof, and a cyclin D (CycD) or a variant thereof.

As used herein, the term "Cdk4 or a variant thereof" refers to a wild-type cyclin-dependent kinase 4 (Cdk4) or a variant of the wild-type Cdk4. A wild-type Cdk4 may have the sequence of SEQ ID NO: 37. A variant of the wild-type Cdk4 (also called Cdk4 variant) refers to a Cdk4 that contains one or more amino acid substitutions, additions, and/or deletions relative to the amino acid sequence of the wild-type Cdk4 (e.g., SEQ ID NO: 37). A Cdk4 variant may have the same length as a wild-type Cdk4 or may be a fragment of the wild-type Cdk4. A Cdk4 variant as described herein is capable of phosphorylation activity and can form a trimeric complex with a CycD or a variant thereof, and an engineered p27 or a wild-type p27. An active Cdk4 or a variant thereof as used herein refers to a Cdk4 or a variant thereof that is an active kinase and is capable of phosphorylating at a phosphorylation site, e.g., a phosphorylation site having the sequence $X_1PX_2X_3$ (SEQ ID NO: 60), wherein $X_1$ is S or T; $X_2$ is any amino acid; and $X_3$ is K or R.

As used herein, the term "Cdk6 or a variant thereof" refers to a wild-type cyclin-dependent kinase 6 (Cdk6) or a variant of the wild-type Cdk6. A wild-type Cdk6 may have the sequence of SEQ ID NO: 52. A variant of the wild-type Cdk6 (also called Cdk6 variant) refers to a Cdk6 that contains one or more amino acid substitutions, additions, and/or deletions relative to the amino acid sequence of the wild-type Cdk6 (e.g., SEQ ID NO: 52). A Cdk6 variant may have the same length as a wild-type Cdk6 or may be a fragment of the wild-type Cdk6. A Cdk6 variant as described herein is capable of phosphorylation activity and can form a trimeric complex with a CycD or a variant thereof, and an engineered p27 or a wild-type p27. An active Cdk6 or a variant thereof as used herein refers to a Cdk6 or a variant thereof that is an active kinase and is capable of phosphorylating at a phosphorylation site, e.g., a phosphorylation site having the sequence $X_1PX_2X_3$ (SEQ ID NO: 60), wherein $X_1$ is S or T; $X_2$ is any amino acid; and $X_3$ is K or R.

As used herein, the term "cyclin D (CycD) or a variant thereof" refers to a wild-type CycD or a variant of the wild-type CycD (also called CycD variant) that is capable of forming a trimeric protein complex described herein comprising an active Cdk4 (or a variant thereof) or Cdk6 (or a variant thereof). A wild-type CycD may be a wild-type CycD1, CycD2, or CycD3. A trimeric protein complex describe herein may comprise any one of the CycD1, CycD2, CycD3, or a variant thereof described herein.

As used herein, the term "trimeric protein complex" or "trimeric complex" refers to a complex formed by three proteins: (i) an engineered p27 or wild-type p27; (ii) a Cdk4 (or a variant thereof) or Cdk6 (or a variant thereof); and (iii) a cyclin D (CycD) (or a variant thereof).

As used herein, the term "percent (%) sequence identity" refers to the percentage of amino acid or nucleic acid residues of a candidate sequence that are identical to the amino acid or nucleic acid residues of a reference sequence after aligning the sequences and introducing gaps, if necessary, to achieve the maximum percent identity (i.e., gaps can be introduced in one or both of the candidate and reference sequences for optimal alignment). In some embodiments, percent sequence identity can be any integer from 50% to 100%. In some embodiments, a sequence is substantially identical to a reference sequence if the sequence has at least 50%, 55%, 60%, 65%, 70%, 75%, 80%, 85%, 90%, 91%, 92%, 93%, 94%, 95%, 96%, 97%, 98%, or 99% sequence identity to the reference sequence as determined using the methods described herein; preferably BLAST using standard parameters, as described below.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A comparison window includes reference to a segment of any one of the number of contiguous positions, e.g., a segment of at least 10 residues. In some embodiments, the comparison window has from 10 to 600 residues, e.g., about 10 to about 30 residues, about 10 to about 20 residues, about 50 to about 200 residues, or about 100 to about 150 residues, in which a sequence may be compared to a reference sequence of the same number of contiguous positions after the two sequences are optimally aligned.

Alignment for purposes of determining percent sequence identity can be achieved in various ways that are within the skill in the art, for instance, using publicly available computer software such as BLAST, ALIGN, or Megalign (DNASTAR) software. The BLAST and BLAST 2.0 algorithms are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. Those skilled in the art can determine appropriate parameters for measuring alignment, including any algorithms needed to achieve maximal alignment over the full length of the sequences being compared. In some embodiments, the percent amino acid or nucleic acid sequence identity of a given candidate sequence to, with, or against a given reference sequence (which can alternatively be phrased as a given candidate sequence that has or includes a certain percent amino acid or nucleic acid sequence identity to, with, or against a given reference sequence) is calculated as follows:

$$100 \times (\text{fraction of } A/B)$$

where A is the number of amino acid or nucleic acid residues scored as identical in the alignment of the candidate sequence and the reference sequence, and where B is the total number of amino acid or nucleic acid residues in the reference sequence. In some embodiments where the length of the candidate sequence does not equal to the length of the reference sequence, the percent amino acid or nucleic acid sequence identity of the candidate sequence to the reference sequence would not equal to the percent amino acid or nucleic acid sequence identity of the reference sequence to the candidate sequence.

In particular embodiments, a reference sequence aligned for comparison with a candidate sequence may show that the candidate sequence exhibits from 50% to 100% identity across the full length of the candidate sequence or a selected portion of contiguous amino acid or nucleic acid residues of the candidate sequence. The length of the candidate sequence aligned for comparison purpose is at least 30%, e.g., at least 40%, e.g., at least 50%, 60%, 70%, 80%, 90%, or 100% of the length of the reference sequence. When a position in the candidate sequence is occupied by the same amino acid or nucleic acid residue as the corresponding position in the reference sequence, then the molecules are identical at that position.

III. Trimeric Protein Complex

In response to mitogenic signals, complexes involving p27, Cdk4 or Cdk6, and cyclin D (CycD) phosphorylate retinoblastoma protein (Rb), leading to the transcription of genes essential for S-phase cell cycle progression. In order to prevent Rb phosphorylation and cancer cell cycle progression, inhibitors of Cdk4 and Cdk6 have been developed in screens using a dimer of Cdk4 or Cdk6 and CycD due to technical challenges in generating the active form of p27 that can complex with Cdk4 or Cdk6 and CycD. However, the dimeric complex does not readily form in the cell. The protein p27 is always found together in complex with active Cdk4 or Cdk6 and CycD and may increase Cdk4/6-CycD stability. The disclosure features trimeric protein complexes comprising p27, Cdk4 (or a variant thereof) or Cdk6 (or a variant thereof), and CycD, in which the Cdk4 (or a variant thereof) or Cdk6 (or a variant thereof) in the trimeric protein complex is an active kinase. The trimeric protein complexes featured herein are closer mimics of the p27-Cdk4/6-CycD complexes found in vivo compared to the Cdk4/6-CycD dimeric complexes used in the past. The trimeric protein complexes described herein may serve as a better tool in screening and selecting chemical compounds that can function as inhibitors of the trimeric protein complex and Cdk4 or Cdk6 to prevent the phosphorylation of Rb, and accordingly, arresting cancer cell cycle progression.

In some embodiments, a trimeric protein complex described herein may comprise an engineered p27, a Cdk4 (or a variant thereof) or a Cdk6 (or a variant thereof), and a CycD (or a variant thereof), in which the Cdk4, Cdk6, or the variant thereof in the trimeric protein complex is an active kinase. The engineered p27 in the trimeric protein complex may have at least one amino acid substitution at a position selected from the group consisting of Y74, Y88, and Y89, in which the amino acid positions are determined with reference to the sequence of SEQ ID NO: 1. Examples of engineered p27 are provided in detail further herein.

In other embodiments, a trimeric protein complex may comprise a phosphorylated, wild-type p27, or a fragment thereof, a Cdk4 (or a variant thereof) or a Cdk6 (or a variant thereof), and a CycD (or a variant thereof), in which the Cdk4 (the variant thereof) or the Cdk6 (or the variant thereof) in the trimeric protein complex is an active kinase. In some embodiments, the phosphorylated, wild-type p27 or a fragment thereof comprises the sequence of any one of SEQ ID NOS: 1-3 and is phosphorylated at Y74, Y88, and/or Y89, wherein the amino acid positions are determined with reference to the sequence of SEQ ID NO: 1. In order to form a trimeric protein complex with an active Cdk4 (or a variant thereof) or Cdk6 (or a variant thereof), a wild-type p27 (or a fragment thereof) may be expressed from a separate cell line and phosphorylated by a kinase prior to formation of the trimeric protein complex.

IV. Engineered p27

The disclosure features an engineered p27 that can form a trimeric protein complex with a Cdk4 (or a variant thereof) or a Cdk6 (or a variant thereof), and a CycD (or a variant thereof). An engineered p27 as described herein may have at least one amino acid substitution at a position selected from the group consisting of Y74, Y88, and Y89, in which the amino acid positions are determined with reference to the sequence of SEQ ID NO: 1. In the trimeric protein complex, an engineered p27 may increase the stability of the dimer of Cdk4 (or a variant thereof) or Cdk6 (or a variant thereof) and CycD (or a variant thereof). In some embodiments, an engineered p27 may have the same length as a wild-type p27 and contains at least one amino acid substitution at a position selected from the group consisting of Y74, Y88, and Y89. In some embodiments, an engineered p27 may be a fragment of the wild-type p27 and contains at least one amino acid substitution at a position selected from the group consisting of Y74, Y88, and Y89.

In some embodiments, an engineered p27 may have one amino acid substitution at a position selected from the group consisting of Y74, Y88, and Y89. In some embodiments, an engineered p27 may have two amino acid substitutions at two positions selected from the group consisting of Y74, Y88, and Y89 (e.g., Y74 and Y88, Y74 and Y89, or Y88 and Y89). In some embodiments, an engineered p27 may have three amino acid substitutions at positions Y74, Y88, and Y89. In some embodiments, the amino acid substation at position Y74 may include, but are not limited to, Y74E and Y74D. In some embodiments, the amino acid substation at position Y74 may include, but are not limited to, Y74E, Y74D, and Y74R. The amino acid substitution at position Y88 may include, but are not limited to, Y88E and Y88D. The amino acid substitution at position Y89 may include, but are not limited to, Y89E and Y89D. In further embodiments, an engineered p27 may be phosphorylated, i.e., phosphorylated at a tyrosine residue (e.g., phosphorylated at one or more of Y74, Y88, and Y89).

Table 1 below lists the sequence of a wild-type p27, fragments of the wild-type p27, and various engineered p27 proteins containing at least one amino acid substitution at a position selected from the group consisting of Y74, Y88, and Y89, in which the amino acid positions are determined with reference to the sequence of SEQ ID NO: 1. An engineered p27 described herein may have at least 90% sequence identity (e.g., 92%, 93%, 94%, 95%, 96%, 97%, 98%, 99%, or 100%) to any one of the sequences of SEQ ID NOS: 1-36 listed in Table 1 and one or more amino acid substitutions, additions, and/or deletions relative to the wild-type p27 (SEQ ID NO: 1).

TABLE 1

| SEQ ID NO | Protein | Sequence |
|---|---|---|
| 1 | Full-length wild-type p27 | MSNVRVSNGSPSLERMDARQAEHPKPSACRNLFGPVDHEELTRDLE KHCRDMEEASQRKWNFDFQNHKPLEGKYEWQEVEKGSLPEFYYR PPRPPKGACKVPAQESQDVSGSRPAAPLIGAPANSEDTHLVDPKTDP SDSQTGLAEQCAGIRKRPATDDSSTQNKRANRTEENVSDGSPNAGS VEQTPKKPGLRRRQT |
| 2 | Amino acids 25-106 of full-length wild-type p27 | KPSACRNLFGPVDHEELTRDLEKHCRDMEEASQRKWNFDFQNHKP LEGKYEWQEVEKGSLPEFYYRPPRPPKGACKVPAQES |
| 3 | Amino acids 25-98 of full-length wild-type p27 | KPSACRNLFGPVDHEELTRDLEKHCRDMEEASQRKWNFDFQNHKP LEGKYEWQEVEKGSLPEFYYRPPRPPKGA |
| 4 | Full-length p27 with Y74E | MSNVRVSNGSPSLERMDARQAEHPKPSACRNLFGPVDHEELTRDLE KHCRDMEEASQRKWNFDFQNHKPLEGKEEWQEVEKGSLPEFYYRP PRPPKGACKVPAQESQDVSGSRPAAPLIGAPANSEDTHLVDPKTDPS DSQTGLAEQCAGIRKRPATDDSSTQNKRANRTEENVSDGSPNAGSV EQTPKKPGLRRRQT |
| 5 | Amino acids 25-106 of p27 with Y74E | KPSACRNLFGPVDHEELTRDLEKHCRDMEEASQRKWNFDFQNHKP LEGKEEWQEVEKGSLPEFYYRPPRPPKGACKVPAQES |

TABLE 1-continued

| SEQ ID NO | Protein | Sequence |
|---|---|---|
| 6 | Amino acids 25-98 of p27 with Y74E | KPSACRNLFGPVDHEELTRDLEKHCRDMEEASQRKWNFDFQNHKP LEGKEEWQEVEKGSLPEFYYRPPRPPKGA |
| 7 | Full-length p27 with Y74D | MSNVRVSNGSPSLERMDARQAEHPKPSACRNLFGPVDHEELTRDLE KHCRDMEEASQRKWNFDFQNHKPLEGKDEWQEVEKGSLPEFYYR PPRPPKGACKVPAQESQDVSGSRPAAPLIGAPANSEDTHLVDPKTDP SDSQTGLAEQCAGIRKRPATDDSSTQNKRANRTEENVSDGSPNAGS VEQTPKKPGLRRRQT |
| 8 | Amino acids 25-106 of p27 with Y74D | KPSACRNLFGPVDHEELTRDLEKHCRDMEEASQRKWNFDFQNHKP LEGKDEWQEVEKGSLPEFYYRPPRPPKGACKVPAQES |
| 9 | Amino acids 25-98 of p27 with Y74D | KPSACRNLFGPVDHEELTRDLEKHCRDMEEASQRKWNFDFQNHKP LEGKDEWQEVEKGSLPEFYYRPPRPPKGA |
| 10 | Full-length p27 with Y74R | MSNVRVSNGSPSLERMDARQAEHPKPSACRNLFGPVDHEELTRDLE KHCRDMEEASQRKWNFDFQNHKPLEGKREWQEVEKGSLPEFYYR PPRPPKGACKVPAQESQDVSGSRPAAPLIGAPANSEDTHLVDPKTDP SDSQTGLAEQCAGIRKRPATDDSSTQNKRANRTEENVSDGSPNAGS VEQTPKKPGLRRRQT |
| 11 | Amino acids 25-106 of p27 with Y74R | KPSACRNLFGPVDHEELTRDLEKHCRDMEEASQRKWNFDFQNHKP LEGKREWQEVEKGSLPEFYYRPPRPPKGACKVPAQES |
| 12 | Amino acids of 25-98 p27 with Y74R | KPSACRNLFGPVDHEELTRDLEKHCRDMEEASQRKWNFDFQNHKP LEGKREWQEVEKGSLPEFYYRPPRPPKGA |
| 13 | Full-length p27 with Y88E | MSNVRVSNGSPSLERMDARQAEHPKPSACRNLFGPVDHEELTRDLE KHCRDMEEASQRKWNFDFQNHKPLEGKYEWQEVEKGSLPEFEYRP PRPPKGACKVPAQESQDVSGSRPAAPLIGAPANSEDTHLVDPKTDPS DSQTGLAEQCAGIRKRPATDDSSTQNKRANRTEENVSDGSPNAGSV EQTPKKPGLRRRQT |
| 14 | Amino acids 25-106 of p27 with Y88E | KPSACRNLFGPVDHEELTRDLEKHCRDMEEASQRKWNFDFQNHKP LEGKYEWQEVEKGSLPEFEYRPPRPPKGACKVPAQES |
| 15 | Amino acids 25-98 of p27 with Y88E | KPSACRNLFGPVDHEELTRDLEKHCRDMEEASQRKWNFDFQNHKP LEGKYEWQEVEKGSLPEFEYRPPRPPKGA |
| 16 | Full-length p27 with Y88D | MSNVRVSNGSPSLERMDARQAEHPKPSACRNLFGPVDHEELTRDLE KHCRDMEEASQRKWNFDFQNHKPLEGKYEWQEVEKGSLPEFDYR PPRPPKGACKVPAQESQDVSGSRPAAPLIGAPANSEDTHLVDPKTDP SDSQTGLAEQCAGIRKRPATDDSSTQNKRANRTEENVSDGSPNAGS VEQTPKKPGLRRRQT |
| 17 | Amino acids 25-106 of p27 with Y88D | KPSACRNLFGPVDHEELTRDLEKHCRDMEEASQRKWNFDFQNHKP LEGKYEWQEVEKGSLPEFDYRPPRPPKGACKVPAQES |
| 18 | Amino acids 25-98 of p27 with Y88D | KPSACRNLFGPVDHEELTRDLEKHCRDMEEASQRKWNFDFQNHKP LEGKYEWQEVEKGSLPEFDYRPPRPPKGA |
| 19 | Full-length p27 with Y89E | MSNVRVSNGSPSLERMDARQAEHPKPSACRNLFGPVDHEELTRDLE KHCRDMEEASQRKWNFDFQNHKPLEGKYEWQEVEKGSLPEFYERP PRPPKGACKVPAQESQDVSGSRPAAPLIGAPANSEDTHLVDPKTDPS DSQTGLAEQCAGIRKRPATDDSSTQNKRANRTEENVSDGSPNAGSV EQTPKKPGLRRRQT |
| 20 | Amino acids 25-106 of p27 with Y89E | KPSACRNLFGPVDHEELTRDLEKHCRDMEEASQRKWNFDFQNHKP LEGKYEWQEVEKGSLPEFYERPPRPPKGACKVPAQES |
| 21 | Amino acids 25-98 of p27 with Y89E | KPSACRNLFGPVDHEELTRDLEKHCRDMEEASQRKWNFDFQNHKP LEGKYEWQEVEKGSLPEFYERPPRPPKGA |

TABLE 1-continued

| SEQ ID NO | Protein | Sequence |
|---|---|---|
| 22 | Full-length p27 with Y89D | MSNVRVSNGSPSLERMDARQAEHPKPSACRNLFGPVDHEELTRDLE KHCRDMEEASQRKWNFDFQNHKPLEGKYEWQEVEKGSLPEFYDR PPRPPKGACKVPAQESQDVSGSRPAAPLIGAPANSEDTHLVDPKTDP SDSQTGLAEQCAGIRKRPATDDSSTQNKRANRTEENVSDGSPNAGS VEQTPKKPGLRRRQT |
| 23 | Amino acids 25-106 of p27 with Y89D | KPSACRNLFGPVDHEELTRDLEKHCRDMEEASQRKWNFDFQNHKP LEGKYEWQEVEKGSLPEFYDRPPRPPKGACKVPAQES |
| 24 | Amino acids of p27 25-98 with Y89D | KPSACRNLFGPVDHEELTRDLEKHCRDMEEASQRKWNFDFQNHKP LEGKYEWQEVEKGSLPEFYDRPPRPPKGA |
| 25 | Full length-p27 with Y74E and Y88E | MSNVRVSNGSPSLERMDARQAEHPKPSACRNLFGPVDHEELTRDLE KHCRDMEEASQRKWNFDFQNHKPLEGKEEWQEVEKGSLPEFEYRP PRPPKGACKVPAQESQDVSGSRPAAPLIGAPANSEDTHLVDPKTDPS DSQTGLAEQCAGIRKRPATDDSSTQNKRANRTEENVSDGSPNAGSV EQTPKKPGLRRRQT |
| 26 | Amino acids 25-106 of p27 with Y74E and Y88E | KPSACRNLFGPVDHEELTRDLEKHCRDMEEASQRKWNFDFQNHKP LEGKEEWQEVEKGSLPEFEYRPPRPPKGACKVPAQES |
| 27 | Amino acids 25-98 of p27 with Y74E and Y88E | KPSACRNLFGPVDHEELTRDLEKHCRDMEEASQRKWNFDFQNHKP LEGKEEWQEVEKGSLPEFEYRPPRPPKGA |
| 28 | Full-length p27 with Y74E and Y89E | MSNVRVSNGSPSLERMDARQAEHPKPSACRNLFGPVDHEELTRDLE KHCRDMEEASQRKWNFDFQNHKPLEGKEEWQEVEKGSLPEFYERP PRPPKGACKVPAQESQDVSGSRPAAPLIGAPANSEDTHLVDPKTDPS DSQTGLAEQCAGIRKRPATDDSSTQNKRANRTEENVSDGSPNAGSV EQTPKKPGLRRRQT |
| 29 | Amino acids 25-106 of p27 with Y74E and Y89E | KPSACRNLFGPVDHEELTRDLEKHCRDMEEASQRKWNFDFQNHKP LEGKEEWQEVEKGSLPEFYERPPRPPKGACKVPAQES |
| 30 | Amino acids 25-98 of p27 with Y74E and Y89E | KPSACRNLFGPVDHEELTRDLEKHCRDMEEASQRKWNFDFQNHKP LEGKEEWQEVEKGSLPEFYERPPRPPKGA |
| 31 | Full-length p27 with Y88E and Y89E | MSNVRVSNGSPSLERMDARQAEHPKPSACRNLFGPVDHEELTRDLE KHCRDMEEASQRKWNFDFQNHKPLEGKYEWQEVEKGSLPEFEERP PRPPKGACKVPAQESQDVSGSRPAAPLIGAPANSEDTHLVDPKTDPS DSQTGLAEQCAGIRKRPATDDSSTQNKRANRTEENVSDGSPNAGSV EQTPKKPGLRRRQT |
| 32 | Amino acids 25-106 of p27 with Y88E and Y89E | KPSACRNLFGPVDHEELTRDLEKHCRDMEEASQRKWNFDFQNHKP LEGKYEWQEVEKGSLPEFEERPPRPPKGACKVPAQES |
| 33 | Amino acids 25-98 of p27 with Y88E and Y89E | KPSACRNLFGPVDHEELTRDLEKHCRDMEEASQRKWNFDFQNHKP LEGKYEWQEVEKGSLPEFEERPPRPPKGA |
| 34 | Full-length p27 with Y74E, Y88E, and Y89E | MSNVRVSNGSPSLERMDARQAEHPKPSACRNLFGPVDHEELTRDLE KHCRDMEEASQRKWNFDFQNHKPLEGKEEWQEVEKGSLPEFEERP PRPPKGACKVPAQESQDVSGSRPAAPLIGAPANSEDTHLVDPKTDPS DSQTGLAEQCAGIRKRPATDDSSTQNKRANRTEENVSDGSPNAGSV EQTPKKPGLRRRQT |
| 35 | Amino acids 25-106 of p27 with Y74E, Y88E, and Y89E | KPSACRNLFGPVDHEELTRDLEKHCRDMEEASQRKWNFDFQNHKP LEGKEEWQEVEKGSLPEFEERPPRPPKGACKVPAQES |

TABLE 1-continued

| SEQ ID NO | Protein | Sequence |
|---|---|---|
| 36 | Amino acids 25-98 of p27 with Y74E, Y88E, and Y89E | KPSACRNLFGPVDHEELTRDLEKHCRDMEEASQRKWNFDFQNHKP LEGKEEWQEVEKGSLPEFEERPPRPPKGA |

V. Cdk4, Cdk6, or a Variant Thereof

Cyclin-dependent kinase 4 or 6 (Cdk4 or Cdk6), when in complex with p27 and CycD, may act as an active kinase in phosphorylating Rb. The Cdk4 or Cdk6 in the trimeric protein complexes described herein may be a wild-type Cdk4 or a wild-type Cdk6, respectively. In other embodiments, the Cdk4 or Cdk6 in the trimeric protein complexes described herein may be a variant of the wild-type Cdk4 or the wild-type Cdk6, respectively, containing one or more amino acid substitutions, additions, and/or deletions relative to the wild-type protein sequence. A Cdk4 or Cdk6 variant may have the same length as the wild-type protein or may be a fragment of the wild-type protein. A Cdk4 variant or Cdk6 variant described herein is capable of phosphorylation activity and can form a trimeric complex with a CycD or a variant thereof, and an engineered p27.

Table 2 below lists the sequences of wild-type Cdk4 and Cdk6 and various Cdk4 and Cdk6 variants containing one or more amino acid substitutions relative to the wild-type protein, in which the amino acid positions are determined with reference to the sequence of SEQ ID NO: 37 (Cdk4) or SEQ ID NO: 52 (Cdk6). A Cdk4 variant described herein may have at least 90% sequence identity (e.g., 92%, 93%, 94%, 95%, 96%, 97%, 98%, 99%, or 100%) to any one of the sequences of SEQ ID NOS: 37-51 listed in Table 2 and one or more amino acid substitutions, additions, and/or deletions relative to the wild-type Cdk4 (SEQ ID NO: 37). A Cdk6 variant described herein may have at least 90% sequence identity (e.g., 92%, 93%, 94%, 95%, 96%, 97%, 98%, 99%, or 100%) to any one of the sequences of SEQ ID NOS: 52-54 listed in Table 2 and one or more amino acid substitutions, additions, and/or deletions relative to the wild-type Cdk4 (SEQ ID NO: 52).

TABLE 2

| SEQ ID NO | Protein | Sequence |
|---|---|---|
| 37 | Wild-type Cdk4 | MATSRYEPVAEIGVGAYGTVYKARDPHSGHFVALKSVRVPNGGGG GGGLPISTVREVALLRRLEAFEHPNVVRLMDVCATSRTDREIKVTL VFEHVDQDLRTYLDKAPPPGLPAETIKDLMRQFLRGLDFLHANCIV HRDLKPENILVTSGGTVKLADFGLARIYSYQMALTPVVVTLWYRAP EVLLQSTYATPVDMWSVGCIFAEMFRRKPLFCGNSEADQLGKIFDL IGLPPEDDWPRDVSLPRGAFPPRGPRPVQSVVPEMEESGAQLLLEM LTFNPHKRISAFRALQHSYLHKDEGNPE |
| 38 | Cdk4 variant with T172D | MATSRYEPVAEIGVGAYGTVYKARDPHSGHFVALKSVRVPNGGGG GGGLPISTVREVALLRRLEAFEHPNVVRLMDVCATSRTDREIKVTL VFEHVDQDLRTYLDKAPPPGLPAETIKDLMRQFLRGLDFLHANCIV HRDLKPENILVTSGGTVKLADFGLARIYSYQMALDPVVVTLWYRA PEVLLQSTYATPVDMWSVGCIFAEMFRRKPLFCGNSEADQLGKIFD LIGLPPEDDWPRDVSLPRGAFPPRGPRPVQSVVPEMEESGAQLLLE MLTFNPHKRISAFRALQHSYLHKDEGNPE |
| 39 | Cdk4 variant with T172E | MATSRYEPVAEIGVGAYGTVYKARDPHSGHFVALKSVRVPNGGGG GGGLPISTVREVALLRRLEAFEHPNVVRLMDVCATSRTDREIKVTL VFEHVDQDLRTYLDKAPPPGLPAETIKDLMRQFLRGLDFLHANCIV HRDLKPENILVTSGGTVKLADFGLARIYSYQMALEPVVVTLWYRAP EVLLQSTYATPVDMWSVGCIFAEMFRRKPLFCGNSEADQLGKIFDL IGLPPEDDWPRDVSLPRGAFPPRGPRPVQSVVPEMEESGAQLLLEM LTFNPHKRISAFRALQHSYLHKDEGNPE |
| 40 | Cdk4 variant with amino acids 44 to 46 deleted, G43E, and G47E | MATSRYEPVAEIGVGAYGTVYKARDPHSGHFVALKSVRVPNGEEG LPISTVREVALLRRLEAFEHPNVVRLMDVCATSRTDREIKVTLVFEH VDQDLRTYLDKAPPPGLPAETIKDLMRQFLRGLDFLHANCIVHRDL KPENILVTSGGTVKLADFGLARIYSYQMALTPVVVTLWYRAPEVLL QSTYATPVDMWSVGCIFAEMFRRKPLFCGNSEADQLGKIFDLIGLPP EDDWPRDVSLPRGAFPPRGPRPVQSVVPEMEESGAQLLLEMLTFNP HKRISAFRALQHSYLHKDEGNPE |
| 41 | Cdk4 variant with amino acids 44 to 46 deleted, G43D, and G47E | MATSRYEPVAEIGVGAYGTVYKARDPHSGHFVALKSVRVPNGDEG LPISTVREVALLRRLEAFEHPNVVRLMDVCATSRTDREIKVTLVFEH VDQDLRTYLDKAPPPGLPAETIKDLMRQFLRGLDFLHANCIVHRDL KPENILVTSGGTVKLADFGLARIYSYQMALTPVVVTLWYRAPEVLL QSTYATPVDMWSVGCIFAEMFRRKPLFCGNSEADQLGKIFDLIGLPP EDDWPRDVSLPRGAFPPRGPRPVQSVVPEMEESGAQLLLEMLTFNP HKRISAFRALQHSYLHKDEGNPE |

TABLE 2-continued

| SEQ ID NO | Protein | Sequence |
|---|---|---|
| 42 | Cdk4 variant with amino acids 44 to 46 deleted, G43E, and G47D | MATSRYEPVAEIGVGAYGTVYKARDPHSGHFVALKSVRVPNGEDG<br>LPISTVREVALLRRLEAFEHPNVVRLMDVCATSRTDREIKVTLVFEH<br>VDQDLRTYLDKAPPPGLPAETIKDLMRQFLRGLDFLHANCIVHRDL<br>KPENILVTSGGTVKLADFGLARIYSYQMALTPVVVTLWYRAPEVLL<br>QSTYATPVDMWSVGCIFAEMFRRKPLFCGNSEADQLGKIFDLIGLPP<br>EDDWPRDVSLPRGAFPPRGPRPVQSVVPEMEESGAQLLLEMLTFNP<br>HKRISAFRALQHSYLHKDEGNPE |
| 43 | Cdk4 variant with amino acids 44 to 46 deleted, G43D, and G47D | MATSRYEPVAEIGVGAYGTVYKARDPHSGHFVALKSVRVPNGDDG<br>LPISTVREVALLRRLEAFEHPNVVRLMDVCATSRTDREIKVTLVFEH<br>VDQDLRTYLDKAPPPGLPAETIKDLMRQFLRGLDFLHANCIVHRDL<br>KPENILVTSGGTVKLADFGLARIYSYQMALTPVVVTLWYRAPEVLL<br>QSTYATPVDMWSVGCIFAEMFRRKPLFCGNSEADQLGKIFDLIGLPP<br>EDDWPRDVSLPRGAFPPRGPRPVQSVVPEMEESGAQLLLEMLTFNP<br>HKRISAFRALQHSYLHKDEGNPE |
| 44 | Cdk4 variant with T172D, amino acids 44 to 46 deleted, G43E, and G47E | MATSRYEPVAEIGVGAYGTVYKARDPHSGHFVALKSVRVPNGEEG<br>LPISTVREVALLRRLEAFEHPNVVRLMDVCATSRTDREIKVTLVFEH<br>VDQDLRTYLDKAPPPGLPAETIKDLMRQFLRGLDFLHANCIVHRDL<br>KPENILVTSGGTVKLADFGLARIYSYQMALDPVVVTLWYRAPEVLL<br>QSTYATPVDMWSVGCIFAEMFRRKPLFCGNSEADQLGKIFDLIGLPP<br>EDDWPRDVSLPRGAFPPRGPRPVQSVVPEMEESGAQLLLEMLTFNP<br>HKRISAFRALQHSYLHKDEGNPE |
| 45 | Cdk4 variant with T172D, amino acids 44 to 46 deleted, G43D, and G47E | MATSRYEPVAEIGVGAYGTVYKARDPHSGHFVALKSVRVPNGDEG<br>LPISTVREVALLRRLEAFEHPNVVRLMDVCATSRTDREIKVTLVFEH<br>VDQDLRTYLDKAPPPGLPAETIKDLMRQFLRGLDFLHANCIVHRDL<br>KPENILVTSGGTVKLADFGLARIYSYQMALDPVVVTLWYRAPEVLL<br>QSTYATPVDMWSVGCIFAEMFRRKPLFCGNSEADQLGKIFDLIGLPP<br>EDDWPRDVSLPRGAFPPRGPRPVQSVVPEMEESGAQLLLEMLTFNP<br>HKRISAFRALQHSYLHKDEGNPE |
| 46 | Cdk4 variant with T172D, amino acids 44 to 46 deleted, G43E, and G47D | MATSRYEPVAEIGVGAYGTVYKARDPHSGHFVALKSVRVPNGEDG<br>LPISTVREVALLRRLEAFEHPNVVRLMDVCATSRTDREIKVTLVFEH<br>VDQDLRTYLDKAPPPGLPAETIKDLMRQFLRGLDFLHANCIVHRDL<br>KPENILVTSGGTVKLADFGLARIYSYQMALDPVVVTLWYRAPEVLL<br>QSTYATPVDMWSVGCIFAEMFRRKPLFCGNSEADQLGKIFDLIGLPP<br>EDDWPRDVSLPRGAFPPRGPRPVQSVVPEMEESGAQLLLEMLTFNP<br>HKRISAFRALQHSYLHKDEGNPE |
| 47 | Cdk4 variant with T172D, amino acids 44 to 46 deleted, G43D, and G47D | MATSRYEPVAEIGVGAYGTVYKARDPHSGHFVALKSVRVPNGDDG<br>LPISTVREVALLRRLEAFEHPNVVRLMDVCATSRTDREIKVTLVFEH<br>VDQDLRTYLDKAPPPGLPAETIKDLMRQFLRGLDFLHANCIVHRDL<br>KPENILVTSGGTVKLADFGLARIYSYQMALDPVVVTLWYRAPEVLL<br>QSTYATPVDMWSVGCIFAEMFRRKPLFCGNSEADQLGKIFDLIGLPP<br>EDDWPRDVSLPRGAFPPRGPRPVQSVVPEMEESGAQLLLEMLTFNP<br>HKRISAFRALQHSYLHKDEGNPE |
| 48 | Cdk4 variant with T172E, amino acids 44 to 46 deleted, G43E, and G47E | MATSRYEPVAEIGVGAYGTVYKARDPHSGHFVALKSVRVPNGEEG<br>LPISTVREVALLRRLEAFEHPNVVRLMDVCATSRTDREIKVTLVFEH<br>VDQDLRTYLDKAPPPGLPAETIKDLMRQFLRGLDFLHANCIVHRDL<br>KPENILVTSGGTVKLADFGLARIYSYQMALEPVVVTLWYRAPEVLL<br>QSTYATPVDMWSVGCIFAEMFRRKPLFCGNSEADQLGKIFDLIGLPP<br>EDDWPRDVSLPRGAFPPRGPRPVQSVVPEMEESGAQLLLEMLTFNP<br>HKRISAFRALQHSYLHKDEGNPE |
| 49 | Cdk4 variant with T172E, amino acids 44 to 46 deleted, G43D, and G47E | MATSRYEPVAEIGVGAYGTVYKARDPHSGHFVALKSVRVPNGDEG<br>LPISTVREVALLRRLEAFEHPNVVRLMDVCATSRTDREIKVTLVFEH<br>VDQDLRTYLDKAPPPGLPAETIKDLMRQFLRGLDFLHANCIVHRDL<br>KPENILVTSGGTVKLADFGLARIYSYQMALEPVVVTLWYRAPEVLL<br>QSTYATPVDMWSVGCIFAEMFRRKPLFCGNSEADQLGKIFDLIGLPP<br>EDDWPRDVSLPRGAFPPRGPRPVQSVVPEMEESGAQLLLEMLTFNP<br>HKRISAFRALQHSYLHKDEGNPE |
| 50 | Cdk4 variant with T172E, amino acids 44 to 46 deleted, G43E, and G47D | MATSRYEPVAEIGVGAYGTVYKARDPHSGHFVALKSVRVPNGEDG<br>LPISTVREVALLRRLEAFEHPNVVRLMDVCATSRTDREIKVTLVFEH<br>VDQDLRTYLDKAPPPGLPAETIKDLMRQFLRGLDFLHANCIVHRDL<br>KPENILVTSGGTVKLADFGLARIYSYQMALEPVVVTLWYRAPEVLL<br>QSTYATPVDMWSVGCIFAEMFRRKPLFCGNSEADQLGKIFDLIGLPP<br>EDDWPRDVSLPRGAFPPRGPRPVQSVVPEMEESGAQLLLEMLTFNP<br>HKRISAFRALQHSYLHKDEGNPE |

TABLE 2-continued

| SEQ ID NO | Protein | Sequence |
|---|---|---|
| 51 | Cdk4 variant with T172E, amino acids 44 to 46 deleted, G43D, and G47D | MATSRYEPVAEIGVGAYGTVYKARDPHSGHFVALKSVRVPNGDDG LPISTVREVALLRRLEAFEHPNVVRLMDVCATSRTDREIKVTLVFEH VDQDLRTYLDKAPPPGLPAETIKDLMRQFLRGLDFLHANCIVHRDL KPENILVTSGGTVKLADFGLARIYSYQMALEPVVVTLWYRAPEVLL QSTYATPVDMWSVGCIFAEMFRRKPLFCGNSEADQLGKIFDLIGLPP EDDWPRDVSLPRGAFPPRGPRPVQSVVPEMEESGAQLLLEMLTFNP HKRISAFRALQHSYLHKDEGNPE |
| 52 | Wild-type Cdk6 | MEKDGLCRADQQYECVAEIGEGAYGKVFKARDLKNGGRFVALKR VRVQTGEEGMPLSTIREVAVLRHLETFEHPNVVRLFDVCTVSRTDR ETKLTLVFEHVDQDLTTYLDKVPEPGVPTETIKDMMFQLLRGLDFL HSHRVVHRDLKPQNILVTSSGQIKLADFGLARIYSFQMALTSVVVTL WYRAPEVLLQSSYATPVDLWSVGCIFAEMFRRKPLFRGSSDVDQLG KILDVIGLPGEEDWPRDVALPRQAFHSKSAQPIEKFVTDIDELGKDL LLKCLTFNPAKRISAYSALSHPYFQDLERCKENLDSHLPPSQNTSEL NTA |
| 53 | Cdk6 variant with T177D | MEKDGLCRADQQYECVAEIGEGAYGKVFKARDLKNGGRFVALKR VRVQTGEEGMPLSTIREVAVLRHLETFEHPNVVRLFDVCTVSRTDR ETKLTLVFEHVDQDLTTYLDKVPEPGVPTETIKDMMFQLLRGLDFL HSHRVVHRDLKPQNILVTSSGQIKLADFGLARIYSFQMALDSVVVT LWYRAPEVLLQSSYATPVDLWSVGCIFAEMFRRKPLFRGSSDVDQL GKILDVIGLPGEEDWPRDVALPRQAFHSKSAQPIEKFVTDIDELGKD LLLKCLTFNPAKRISAYSALSHPYFQDLERCKENLDSHLPPSQNTSE LNTA |
| 54 | Cdk6 variant with T177E | MEKDGLCRADQQYECVAEIGEGAYGKVFKARDLKNGGRFVALKR VRVQTGEEGMPLSTIREVAVLRHLETFEHPNVVRLFDVCTVSRTDR ETKLTLVFEHVDQDLTTYLDKVPEPGVPTETIKDMMFQLLRGLDFL HSHRVVHRDLKPQNILVTSSGQIKLADFGLARIYSFQMALESVVVTL WYRAPEVLLQSSYATPVDLWSVGCIFAEMFRRKPLFRGSSDVDQLG KILDVIGLPGEEDWPRDVALPRQAFHSKSAQPIEKFVTDIDELGKDL LLKCLTFNPAKRISAYSALSHPYFQDLERCKENLDSHLPPSQNTSEL NTA |

VI. Cyclin D

The CycD or a variant thereof in the trimeric protein complexes described herein may be a wild-type CycD or a variant of the wild-type CycD. A wild-type CycD may be a wild-type CycD1, CycD2, or CycD3. A CycD variant comprises one or more amino acid substitutions, additions, and/or deletions relative to the wild-type protein sequence (e.g., wild-type CycD1, CycD2, or CycD3). A trimeric protein complex comprising an active Cdk4 (or a variant thereof) or Cdk6 (or a variant thereof) describe herein may comprise any one of CycD1, CycD2, CycD3, or a variant thereof described herein.

Table 3 below lists the sequences of wild-type CycD1, CycD2, CycD3, and various CycD variants containing one or more amino acid substitutions relative to the wild-type protein, in which the amino acid positions are determined with reference to the sequence of SEQ ID NO: 55 (CycD1), SEQ ID NO: 57 (CycD2), or SEQ ID NO: 58 (CycD3). A CycD1 variant described herein may have at least 90% sequence identity (e.g., 92%, 93%, 94%, 95%, 96%, 97%, 98%, 99%, or 100%) to the sequence of SEQ ID NO: 55 or 56 listed in Table 3 and one or more amino acid substitutions, additions, and/or deletions relative to the wild-type CycD1 (SEQ ID NO: 55). A CycD2 variant described herein may have at least 90% sequence identity (e.g., 92%, 93%, 94%, 95%, 96%, 97%, 98%, 99%, or 100%) to the sequence of SEQ ID NO: 57 listed in Table 3 and one or more amino acid substitutions, additions, and/or deletions relative to the wild-type CycD2 (SEQ ID NO: 57). A CycD3 variant described herein may have at least 90% sequence identity (e.g., 92%, 93%, 94%, 95%, 96%, 97%, 98%, 99%, or 100%) to the sequence of SEQ ID NO: 58 listed in Table 3 and one or more amino acid substitutions, additions, and/or deletions relative to the wild-type CycD3 (SEQ ID NO: 58).

TABLE 3

| SEQ ID NO | Protein | Sequence |
|---|---|---|
| 55 | Full-length wild-type CycD1 | MEHQLLCCEVETIRRAYPDANLLNDRVLRAMLKAEETCAPSVSYF KCVQKEVLPSMRKIVATWMLEVCEEQKCEEEVFPLAMNYLDRFLS LEPVKKSRLQLLGATCMFVASKMKETIPLTAEKLCIYTDNSIRPEEL LQMELLLVNKLKWNLAAMTPHDFIEHFLSKMPEAEENKQIIRKHAQ TFVALCATDVKFISNPPSMVAAGSVVAAVQGLNLRSPNNFLSYYRL TRFLSRVIKCDPDCLRACQEQIEALLESSLRQAQQNMDPKAAEEEEE EEEEVDLACTPTDVRDVDI |

TABLE 3-continued

| SEQ ID NO | Protein | Sequence |
|---|---|---|
| 56 | Amino acids 19-267 of full-length wild-type CycD1 | DANLLNDRVLRAMLKAEETCAPSVSYFKCVQKEVLPSMRKIVATW MLEVCEEQKCEEEVFPLAMNYLDRFLSLEPVKKSRLQLLGATCMF VASKMKETIPLTAEKLCIYTDNSIRPEELLQMELLLVNKLKWNLAA MTPHDFIEHFLSKMPEAEENKQIIRKHAQTFVALCATDVKFISNPPS MVAAGSVVAAVQGLNLRSPNNFLSYYRLTRFLSRVIKCDPDCLRAC QEQIEALLESSLRQAQQNMD |
| 57 | Full-length wild-type CycD2 | MELLCHEVDPVRRAVRDRNLLRDDRVLQNLLTIEERYLPQCSYFKC VQKDIQPYMRRMVATWMLEVCEEQKCEEEVFPLAMNYLDRFLAG VPTPKSHLQLLGAVCMFLASKLKETSPLTAEKLCIYTDNSIKPQELL EWELVVLGKLKWNLAAVTPHDFIEHILRKLPQQREKLSLIRKHAQT FIALCATDFKFAMYPPSMIATGSVGAAICGLQQDEEVSSLTCDALTE LLAKITNTDVDCLKACQEQIEAVLLNSLQQYRQDQRDGSKSEDELD QASTPTDVRDIDL |
| 58 | Full-length wild-type CycD3 | MELLCCEGTRHAPRAGPDPRLLGDQRVLQSLLRLEERYVPRASYFQ CVQREIKPHMRKMLAYWMLEVCEEQRCEEEVFPLAMNYLDRYLS CVPTRKAQLQLLGAVCMLLASKLRETTPLTIEKLCIYTDHAVSPRQL RDWEVLVLGKLKWDLAAVIAHDFLAFILHRLSLPRDRQALVKKHA QTFLALCATDYTFAMYPPSMIATGSIGAAVQGLGACSMSGDELTEL LAGITGTEVDCLRACQEQIEAALRESLREASQTSSSPAPKAPRGSSSQ GPSQTSTPTDVTAIHL |

VII. Methods of Generating a Trimeric Protein Complex

In some embodiments, for a trimeric protein complex comprising an engineered p27, a Cdk4 (or a variant thereof) or a Cdk6 (or a variant thereof), and a CycD (or a variant thereof), each member of the trimeric protein complex may be expressed from the same cell line or from separate cell lines. In some embodiments, all three members may be co-expressed from the same cell line, in which each member may be encoded in an expression vector configured to express the protein. In other embodiments, for a trimeric protein complex comprising a phosphorylated, wild-type p27 or a fragment thereof (e.g., any one of SEQ ID NOS: 1-3), a Cdk4 (or a variant thereof) or a Cdk6 (or a variant thereof), and a CycD (or a variant thereof), the wild-type p27, or a fragment thereof, may be expressed in a cell line separately from the other two members of the complex. Once the wild-type p27, or a fragment thereof, is isolated and purified, the wild-type p27, or a fragment thereof, may be incubated with a kinase (e.g., Brk kinase, Src kinase, and Abl kinase) in order to generate the phosphorylated wild-type p27 or fragment thereof. The phosphorylated, wild-type p27, or fragment thereof, may then be incubated with the Cdk4 (or a variant thereof) or Cdk6 (or a variant thereof), and the CycD or a variant thereof, in order to generate the trimeric protein complex.

Each protein in the trimeric protein complex described herein may be produced from a host cell. A host cell refers to a vehicle that includes the necessary cellular components, e.g., organelles, needed to express the proteins and complexes described herein from their corresponding nucleic acids. The nucleic acids may be included in nucleic acid vectors that can be introduced into the host cell by conventional techniques known in the art (e.g., transformation, transfection, electroporation, calcium phosphate precipitation, direct microinjection, infection, etc.). The choice of nucleic acid vectors depends in part on the host cells to be used. Generally, preferred host cells are of either prokaryotic (e.g., bacterial) or eukaryotic (e.g., insect or mammalian) origin.

Nucleic Acid Vectors and Host Cells

A nucleic acid sequence encoding the amino acid sequence of a protein (e.g., a engineered p27) may be prepared by a variety of methods known in the art. These methods include, but are not limited to, oligonucleotide-mediated (or site-directed) mutagenesis and PCR mutagenesis. A nucleic acid molecule encoding a protein may be obtained using standard techniques, e.g., gene synthesis. Alternatively, a nucleic acid molecule encoding a wild-type protein (e.g., a wild-type p27 having the sequence of SEQ ID NO: 1) may be mutated to contain specific amino acid substitutions using standard techniques in the art, e.g., QuikChange™ mutagenesis. Nucleic acid molecules may be synthesized using a nucleotide synthesizer or PCR techniques.

Nucleic acid sequences encoding a protein in the trimeric protein complex of the disclosure (e.g., an engineered p27) may be inserted into a vector capable of replicating and expressing the nucleic acid molecules in prokaryotic or eukaryotic host cells. Many vectors are available in the art and can be used for the purpose of the disclosure. Each vector may contain various components that may be adjusted and optimized for compatibility with the particular host cell. For example, the vector components may include, but are not limited to, an origin of replication, a selection marker gene, a promoter, a ribosome binding site, a signal sequence, the nucleic acid sequence encoding the protein of interest, and a transcription termination sequence. In some embodiments, a vector used to express a protein in the trimeric protein complex may be a baculovirus vector. In some embodiments, the baculovirus vector may have a polyhedrin promoter. In some embodiments, a vector used to express a protein in the trimeric protein complex may be a PGEX vector. In some embodiments, the PGEX vector may have a T7 promoter.

In some embodiments, insect cells are used as host cells for the disclosure. Examples of insect cells types include, but are not limited to, Sf9, Sf21, and S2 cells. In particular embodiments, Sf9 cells may be used to express a protein in the trimeric protein complex of the disclosure. In other embodiments, E. coli cells are used as host cells for the invention. Examples of E. coli strains include, but are not limited to, *E. coli* 294 (ATCC® 31,446), *E. coli* λ1776 (ATCC® 31,537, *E. coli* BL21 (DE3) (ATCC® BAA-1025), and *E. coli* RV308 (ATCC® 31,608). Different host cells have characteristic and specific mechanisms for the post-translational processing and modification of protein products. In other embodiments, mammalian cells are used as host cells for the invention. Examples of mammalian cell types include, but are not limited to, human embryonic kidney (HEK) (e.g., HEK293, HEK 293F), Chinese hamster ovary (CHO), HeLa, COS, PC3, Vero, MC3T3, NS0, Sp2/0, VERY, BHK, MDCK, W138, BT483, Hs578T, HTB2, BT20, T47D, NS0 (a murine myeloma cell line that does not endogenously produce any immunoglobulin chains), CRL7O3O, and HsS78Bst cells. Appropriate cell lines or host systems may be chosen to ensure the correct modification and processing of the protein expressed. The above-described expression vectors may be introduced into appropriate host cells using conventional techniques in the art, e.g., transformation, transfection, electroporation, calcium phosphate precipitation, and direct microinjection. Once the vectors are introduced into host cells for protein production, host cells are cultured in conventional nutrient media modified as appropriate for inducing promoters, selecting transformants, or amplifying the genes encoding the desired sequences. Methods for expression of therapeutic proteins are known in the art, see, for example, Paulina Balbas, Argelia Lorence (eds.) Recombinant Gene Expression: Reviews and Protocols (*Methods in Molecular Biology*), Humana Press; 2nd ed. 2004 (Jul. 20, 2004) and Vladimir Voynov and Justin A. Caravella (eds.) Therapeutic Proteins: Methods and Protocols (*Methods in Molecular Biology*) Humana Press; 2nd ed. 2012 (Jun. 28, 2012).

Protein Production, Recovery, and Purification

Host cells used to produce the proteins and complexes of the disclosure may be grown in media known in the art and suitable for culturing of the selected host cells. Examples of suitable media for bacterial host cells include Luria broth (LB) plus necessary supplements, such as a selection agent, e.g., ampicillin. Examples of suitable media for mammalian host cells include Minimal Essential Medium (MEM), Dulbecco's Modified Eagle's Medium (DMEM), Expi293™ Expression Medium, DMEM with supplemented fetal bovine serum (FBS), and RPMI-1640. Host cells are cultured at suitable temperatures, such as from about 20° C. to about 39° C., e.g., from 25° C. to about 37° C., preferably 37° C., and $CO_2$ levels, such as 5 to 10% (preferably 8%). The pH of the medium is generally from about 6.8 to 7.4, e.g., 7.0, depending mainly on the host organism. If an inducible promoter is used in the expression vector of the invention, protein expression may be induced under conditions suitable for the activation of the promoter.

Protein recovery typically involves disrupting the host cell, generally by such means as osmotic shock, sonication, or lysis. Once the cells are disrupted, cell debris may be removed by centrifugation or filtration. The proteins may be further purified. A protein or complex of the disclosure may be purified by any method known in the art of protein purification, for example, by protein A affinity, other chromatography (e.g., ion exchange, affinity, and size-exclusion column chromatography), centrifugation, differential solubility, or by any other standard technique for the purification of proteins. (see Process Scale Purification of Antibodies, Uwe Gottschalk (ed.) John Wiley & Sons, Inc., 2009).

In some instances, a protein may be conjugated to a purification tag to facilitate purification and isolation of the protein from, e.g., a whole cell lysate mixture. In some embodiments, the purification tag binds to another moiety that has a specific affinity for the purification tag. In some embodiments, such moieties which specifically bind to the purification tag are attached to a solid support, such as a matrix, a resin, or agarose beads. Examples of purification tags that may be joined to a protein include, but are not limited to, a glutathione S-transferase (GST) tag and a hexa-histidine peptide (SEQ ID NO: 66). GST is a 211 amino acid protein (about 26 kDa) whose DNA sequence may be integrated into expression vectors for production of recombinant proteins. The result of expression from this vector is a GST-tagged fusion protein in which the functional GST protein may be fused to, e.g., the N-terminus or C-terminus of the recombinant protein. Because GST folds rapidly into a stable and highly soluble protein upon translation, inclusion of the GST tag may promote greater expression and solubility of recombinant proteins than expression without the tag. In addition, GST-tagged fusion proteins may be purified or detected based on the ability of GST to bind its substrate, glutathione (GSH). In some embodiments, a solid support may be functionalized with GSH to isolate and purified GST-tagged fusion proteins. A hexa-histidine peptide (HHHHHH (SEQ ID NO: 66)) binds to nickel-functionalized agarose affinity column with micromolar affinity. In some embodiments, the purification tag may be cleaved from the fusion protein once it is purified. A protease cleavage sequence (e.g., a TEV protease cleavage sequence ENLYFQG (SEQ ID NO: 67) may be inserted between the protein of interest and the purification tag.

In other embodiments, a FLAG peptide, a myc peptide, or a hemagglutinin (HA) peptide may be used as a purification tag. In some embodiments, a FLAG peptide includes the sequence DYKDDDDK (SEQ ID NO: 68). In some embodiments, a FLAG peptide includes integer multiples of the sequence DYKDDDDK (SEQ ID NO: 68) in tandem series, e.g., 3×DYKDDDDK (SEQ ID NO: 71). In some embodiments, a myc peptide includes the sequence EQKLISEEDL (SEQ ID NO: 69). In some embodiments, a myc peptide includes integer multiples of the sequence EQKLISEEDL (SEQ ID NO: 69) in tandem series, e.g., 3×EQKLISEEDL (SEQ ID NO: 72). In some embodiments, an HA peptide includes the sequence YPYDVPDYA (SEQ ID NO: 70). In some embodiments, an HA peptide includes integer multiples of the sequence YPYDVPDYA (SEQ ID NO: 70) in tandem series, e.g., 3×YPYDVPDYA (SEQ ID NO: 73). Antibodies that specifically recognize and bind to the FLAG, myc, or HA purification tag are well-known in the art and often commercially available. A solid support (e.g., a matrix, a resin, or agarose beads) functionalized with these antibodies may be used to purify a protein that includes a FLAG, myc, or HA peptide.

VIII. Methods of Screening Inhibitors

The disclosure also features methods of screening for inhibitors of the trimeric protein complexes described herein, which are closer mimics of the p27-Cdk4/6-CycD complexes found in vivo compared to the Cdk4/6-CycD dimeric complexes. The method comprises (a) providing the trimeric protein complex by incubating: (i) an engineered p27 described herein or a phosphorylated, wild-type p27 or a fragment thereof; (e.g., any one of SEQ ID NOS: 1-36); (ii) a Cdk4 (or a variant thereof) or Cdk6 (or a variant thereof); and (iii) a CycD or a variant thereof, under conditions that allow the formation of the trimeric protein complex comprising an active Cdk4 (or a variant thereof) or Cdk6 (or a variant thereof); (b) contacting the trimeric protein complex with a compound and a substrate of the Cdk4 (or a variant thereof) or Cdk6 (or a variant thereof); (c) determining the phosphorylation status of the substrate, wherein the compound is an inhibitor of the trimeric protein complex if the compound inhibits the phosphorylation activity of the Cdk4 (or a variant thereof) or Cdk6 (or a variant thereof).

In some embodiments of the methods of screening for inhibitors of the trimeric protein complexes described herein, the substrate used may comprise a phosphorylation site having the sequence is $X_1PX_2X_3$ (SEQ ID NO: 60), wherein $X_1$ is S or T; $X_2$ is any amino acid; and $X_3$ is K or R. An active Cdk4 (or a variant thereof) or Cdk6 (or a variant thereof) in the complex may phosphorylate the substrate at $X_1$ in the phosphorylation site. In some embodiments, any protein having a phosphorylation site having the sequence is $X_1PX_2X_3$ (SEQ ID NO: 60) may be used in the methods. Examples of a substrate include, but are not limited to, Rb, FoxM1, histone H1, or a variant thereof. The sequences of some exemplary substrates and their variants are listed in Table 4 below.

TABLE 4

| SEQ ID NO | Protein | Sequence |
| --- | --- | --- |
| 61 | Full-length, wild-type Rb | MPPKTPRKTAATAAAAAAEPPAPPPPPPPEEDPEQDSGPEDLPLVR LEFEETEEPDFTALCQKLKIPDHVRERAWLTWEKVSSVDGVLGGY IQKKKELWGICIFIAAVDLDEMSFTFTELQKNIEISVHKFFNLLKEI DTSTKVDNAMSRLLKKYDVLFALFSKLERTCELIYLTQPSSSISTEI NSALVLKVSWITFLLAKGEVLQMEDDLVISFQLMLCVLDYFIKLS PPMLLKEPYKTAVIPINGSPRTPRRGQNRSARIAKQLENDTRIIEVL CKEHECNIDEVKNVYFKNFIPFMNSLGLVTSNGLPEVENLSKRYE EIYLKNKDLDARLFLDHDKTLQTDSIDSFETQRTPRKSNLDEEVNV IPPHTPVRTVMNTIQQLMMILNSASDQPSENLISYFNNCTVNPKESI LKRVKDIGYIFKEKFAKAVGQGCVEIGSQRYKLGVRLYYRVMES MLKSEEERLSIQNFSKLLNDNIFHMSLLACALEVVMATYSRSTSQ NLDSGTDLSFPWILNVLNLKAFDPYKVIESFIKAEGNLTREMIKHL ERCEHRIMESLAWLSDSPLFDLIKQSKDREGPTDHLESACPLNLPL QNNHTAADMYLSPVRSPKKKGSTTRVNSTANAETQATSAFQTQK PLKSTSLSLFYKKVYRLAYLRLNTLCERLLSEHPELEHIIWTLFQHT LQNEYELMRDRHLDQIMMCSMYGICKVKNIDLKFKIIVTAYKDLP HAVQETFKRVLIKEEEYDSIIVFYNSVFMQRLKTNILQYASTRPPTL SPIPHIPRSPYKFPSSPLRIPGGNIYISPLKSPYKISEGLPTPTKMTPRS RILVSIGESFGTSEKFQKINQMVCNSDRVLKRSAEGSNPPKPLKKL RFDIEGSDEADGSKHLPGESKFQQKLAEMTSTRTRMQKQKMNDS MDTSNKEEK |
| 62 | C-terminal fragment (amino acids 771-928) of wild-type Rb | YASTRPPTLSPIPHIPRSPYKFPSSPLRIPGGNIYISPLKSPYKISEGLP TPTKMTPRSRILVSIGESFGTSEKFQKINQMVCNSDRVLKRSAEGS NPPKPLKKLRFDIEGSDEADGSKHLPGESKFQQKLAEMTSTRTRM QKQKMNDSMDTSNKEEK |
| 63 | Full-length, wild-type FoxM1 | MKTSPRRPLILKRRRLPLPVQNAPSETSEEEPKRSPAQQESNQAEA SKEVAESNSCKFPAGIKIINHPTMPNTQVVAIPNNANIHSIITALTA KGKESGSSGPNKFILISCGGAPTQPPGLRPQTQTSYDAKRTEVTLE TLGPKPAARDVNLPRPPGALCEQKRETCADGEAAGCTINNSLSNI QWLRKMSSDGLGSRSIKQEMEEKENCHLEQRQVKVEEPSRPSAS WQNSVSERPPYSYMAMIQFAINSTERKRMTLKDIYTWIEDHFPYF KHIAKPGWKNSIRHNLSLHDMFVRETSANGKVSPWTIHPSANRYL TLDQVFKPLDPGSPQLPEHLESQQKRPNPELRRNMTIKTELPLGAR RKMKPLLPRVSSYLVPIQFPVNQSLVLQPSVKVPLPLAASLMSSEL ARHSKRVRIAPKVLLAEEGIAPLSSAGPGKEEKLLFGEGFSPLLPV QTIKEEEIQPGEEMPHLARPIKVESPPLEEWPSPAPSFKEESSHSWE DSSQSPTPRPKKSYSGLRSPTRCVSEMLVIQHRERRERSRSRRKQH LLPPCVDEPELLFSEGPSTSRWAAELPFPADSSDPASQLSYSQEVG GPFKTPIKETLPISSTPSKSVLPRTPESWRLTPPAKVGGLDFSPVQTS QGASDPLPDPLGLMDLSTTPLQSAPPLESPQRLLSSEPLDLISVPFG NSSPSDIDVPKPGSPEPQVSGLAANRSLTEGLVLDTMNDSLSKILL DISFPGLDEDPLGPDNINWSQFIPELQ |
| 64 | Transactivation domain (amino acids 526-748) of wild-type FoxM1 | CVSEMLVIQHRERRERSRSRRKQHLLPPCVDEPELLFSEGPSTSRW AAELPFPADSSDPASQLSYSQEVGGPFKTPIKETLPISSTPSKSVLPR TPESWRLTPPAKVGGLDFSPVQTSQGASDPLPDPLGLMDLSTTPL QSAPPLESPQRLLSSEPLDLISVPFGNSSPSDIDVPKPGSPEPQVSGL AANRSLTEGLVLDTMNDSLSKILLDISFPGLDEDPL |
| 65 | Full-length, wild-type histone H1 | MSETVPPAPAASAAPEKPLAGKKAKKPAKAAAASKKKPAGPSVS ELIVQAASSSKERGGVSLAALKKALAAAGYDVEKNNSRIKLGIKS LVSKGTLVQTKGTGASGSFKLNKKASSVETKPGASKVATKTKAT GASKKLKKATGASKKSVKTPKKAKKPAATRKSSKNPKKPKTVKP KKVAKSPAKAKAVKPKAAKARVTKPKTAKPKKAAPKKK |

Methods and techniques for determining the phosphorylation status of a protein are available in the art. For example, radioactive $^{32}$P-ATP may be used in phosphorylating a protein. $^{32}$P-ATP is subsequently incorporated into the protein. Analysis of the phosphorylated protein may be performed by autoradiography. Other methods for measuring phosphorylation may involve isolating the phosphorylated protein by immunoprecipitation, followed by measurement of reactivity of the phosphorylated protein with a labeled phospho-threonine specific antibody. Antibodies specific for certain phosphorylated threonine residues may also be used directly on live cells with phosphorylated proteins on the cell surface or on whole cell lysates or a mixture of proteins after the lysates or the mixture of proteins are separated by electrophoresis and transferred to a membrane (e.g., PVDF or nitrocellulose in Western blots). Moreover, mass spectrometric techniques such as collision-induced dissociation (CID) and electron transfer dissociation (ETD) may also provide comprehensive parallel analysis of peptide sequences and phosphorylation.

Enzyme-linked immunosorbent assays (ELISAs) may also be used to measure phosphorylation. ELISA may be more quantitative than Western blotting. The format for this microplate-based assay typically utilizes a capture antibody specific for the desired protein, independent of the phosphorylation state in order to first capture the protein on the microplate. A detection antibody specific for the phosphorylation site to be analyzed is then added. These assays are typically designed using colorimetric or fluorometric detection. The intensity of the resulting signal is directly proportional to the concentration of phosphorylated protein present in the original sample. The results from ELISA are easily quantifiable by utilizing a calibrated standard. Further, high specificity is possible due to the use of two antibodies specific for the target protein employed together in the sandwich format. The higher sensitivity often accomplished using ELISAs may allow for smaller sample volumes and the detection of low abundance proteins. Finally, the microplate-based format also allows for much higher throughput than traditional Western blotting.

EXAMPLES

Example 1—Generating Trimeric Protein Complex p27-Cdk4-CycD Using an Engineered p27

Human Cdk4 variant (SEQ ID NO: 48), CycD1 variant (SEQ ID NO: 56), and engineered p27 (SEQ ID NO: 6 for amino acids 25-98 of p27 with Y74E) were co-expressed in Sf9 cells (Expression Systems, Davis, Calif.). Cells were simultaneously infected with three baculovirus vectors configured to express the Cdk4 variant, the CycD1 variant, and the engineered p27. Each baculovirus vector was generated using the pFastbac system, which utilizes the polyhedrin promoter. The Cdk4 variant and the engineered p27 were expressed as a GST fusion protein and the CycD1 variant was co-expressed untagged. Lysates were first purified by GS4B affinity chromatography (GE Healthcare). The protein complex was then eluted from the resin and subject to SOURCE 15Q anion exchange chromatography (GE Healthcare). The elution fraction from the anion exchange chromatography was then subjected to TEV protease cleavage overnight in 25 mM Tris, 200 mM NaCl, 1 mM DTT, and 0.5 mM EDTA (pH 8.0) at 4° C. The purified p27-Cdk4-CycD1 trimeric protein complex was then passed over GS4B affinity resin again to remove free GST. The p27-Cdk4-CycD1 trimeric protein complex was then concentrated, and stored in a buffer containing 20 mM Tris, 200 mM NaCl, 1 mM DTT, and 20% glycerol (pH 8.0).

Example 2—Generating Trimeric Protein Complex p27-Cdk4-CycD Using a Wild-Type p27

A dimer of Cdk4-CycD1 was first purified following the same protocol of expression and purification as described above, except the baculovirus vector configured to express p27 was left out of the initial infection. Engineered p27 (SEQ ID NO: 6 for amino acids 25-98 of p27 with Y74E) was expressed in E. coli as a fusion protein from a PGEX vector backbone containing T7 promoter. GST-p27 KID fusion was purified as described above.

In order to generate phosphorylated p27 KID, human Brk kinase was expressed in Sf9 cells as a GST fusion protein using the same pFastbac system (polyhedrin promoter). GST-Brk kinase fusion was purified as described above, except the GST fusion tag was not cut. About 100 mg p27 KID was treated with 10% GST-Brk kinase fusion (m/m) in a buffer containing 50 mM Tris, 150 mM NaCl, 1 mM DTT, 10 mM $MgCl_2$ and 1 mM ATP (pH 8.0) and incubated at 4° C. for 24 hours. The phosphorylated p27 was purified by passing through GS4B affinity resin to remove GST-Brk kinase and eluted from a Superdex 75 column (GE Healthcare) in a buffer containing 25 mM Tris, 100 mM NaCl, and 1 mM DTT, (pH 8.0). To form and reconstitute the Cdk4-CycD1-phosp27 trimeric protein complex, three-fold molar excess of phosp27 was mixed with the purified Cdk4-CycD1 dimeric complex. After incubation for 30 minutes on ice, the trimeric protein complex was purified from a Superdex 75 column (GE Healthcare) in a buffer containing 25 mM Tris, 100 mM NaCl, and 1 mM DTT, (pH 8.0).

Example 3—Kinase Assays

The phosphorylation activity of Cdk4 in various complexes was tested using different substrates. The protein complexes tested were:

(i) Cdk4-CycD1 dimeric complex (SEQ ID NO: 37 for wild-type Cdk4 and SEQ ID NO: 56 for CycD1 variant), (ii) Cdk4-CycD1 dimeric complex (SEQ ID NO: 39 for Cdk4 variant having T172E substitution and SEQ ID NO: 56 for CycD1 variant), (iii) wild-type p27-Cdk4-CycD1 trimeric complex with unphosphorylated p27 (SEQ ID NO: 1 for wild-type p27, SEQ ID NO: 37 for wild-type Cdk4 and SEQ ID NO: 56 for CycD1 variant), (iv) wild-type p27-Cdk4-CycD1 trimeric complex with unphosphorylated p27 (SEQ ID NO: 1 for wild-type p27, SEQ ID NO: 39 for Cdk4 variant having T172E substitution and SEQ ID NO: 56 for CycD1 variant), (v) wild-type p27-Cdk4-CycD1 trimeric complex with phosphorylated p27 (SEQ ID NO: 1 for wild-type p27, SEQ ID NO: 37 for wild-type Cdk4 and SEQ ID NO: 56 for CycD1 variant), (vi) wild-type p27-Cdk4-CycD1 trimeric complex with phosphorylated p27 (SEQ ID NO: 1 for wild-type p27, SEQ ID NO: 37 for Cdk4 variant having T172E substitution and SEQ ID NO: 56 for CycD1 variant), (vii) engineered p27-Cdk4-CycD1 trimeric complex (SEQ ID NO: 34 or 35 for full-length p27 with Y74E, Y88E, and Y89E, or for amino acids 25-106 of p27 with Y74E, Y88E, and Y89E, respectively, SEQ ID NO: 37 for wild-type Cdk4 and SEQ ID NO: 56 for CycD1 variant), and (viii) engineered p27-Cdk4-CycD1 trimeric complex (SEQ ID NO: 34 or 35 for full-length p27 with Y74E, Y88E, and Y89E, or for amino acids 25-106 of p27 with Y74E, Y88E, and Y89E, respectively, SEQ ID NO: 37 for Cdk4 variant having T172E substitution and SEQ ID NO: 56 for CycD1 variant).

The substrates used in the kinase assays were the C-terminal domain of the retinoblastoma protein (Rb (771-928); SEQ ID NO: 62), the transactivation domain of FoxM1 (FoxM1 (526-748); SEQ ID NO: 64), and full-length histone H1 (SEQ ID NO: 65).

To observe kinase activity of the Cdk4 or variant thereof in the protein complexes described above, 0.5 µM protein complex was mixed with 20 µM substrate in a buffer containing 25 mM Tris, 200 mM NaCl, 10 mM $MgCl_2$, 1 mM DTT, 250 µM ATP, and 100 µCi of $^{32}$P-γ-ATP (pH 7.0). The substrate was diluted into the reaction buffer at the appropriate concentration, and the reaction was initiated through addition of the complex. The reaction was quenched after 30 minutes through addition of SDS-PAGE loading buffer.

Figure 1B:
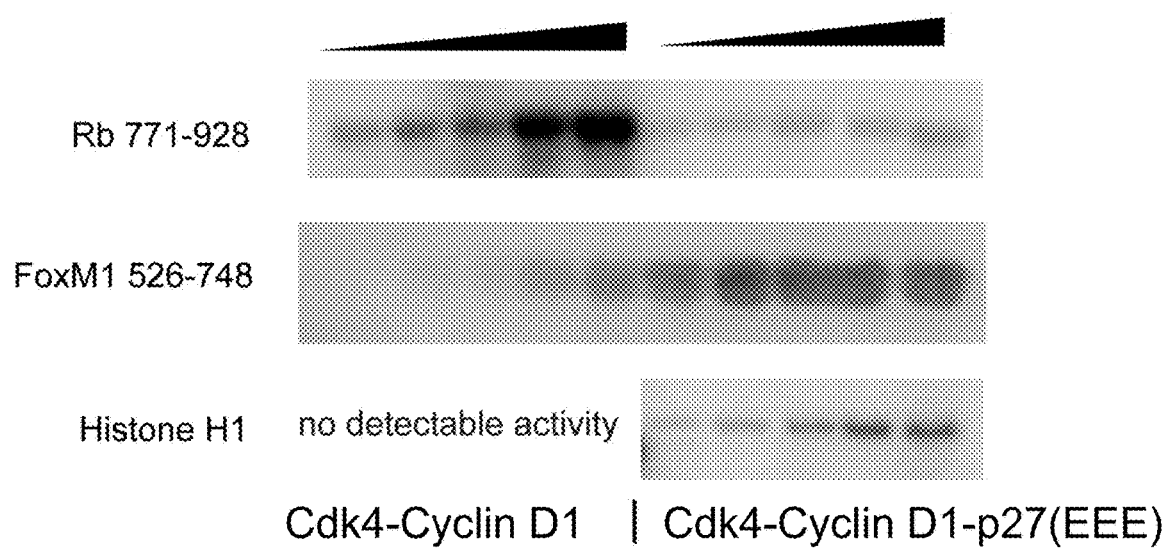
FIG. 1B shows steady-state kinetic assays measuring initial rate of phosphorylation as a function of ATP concentration for the indicated protein complex and substrate.
Figures 1C, 1D:
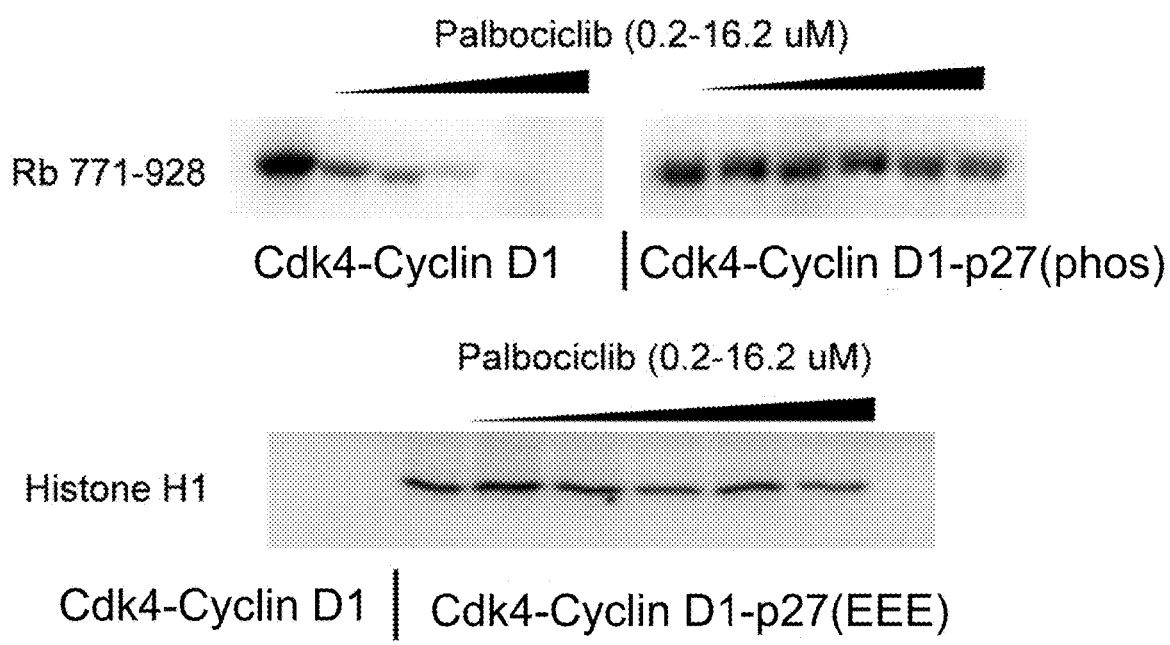
FIG. 1C shows a summary of kinetic results. The engineered p27 with Y74E, Y88E, and Y89E-Cdk4-CycD1 trimeric complex enhances ATP substrate capture and has a greater activity toward FoxM1 and histone 1.
FIG. 1D shows the wild-type p27-Cdk4-CycD1 trimeric complex with phosphorylated p27 and engineered p27 with Y74E, Y88E, and Y89E-Cdk4-CycD1 trimeric complex are poorly inhibited by palbociclib.
Figure 1E:
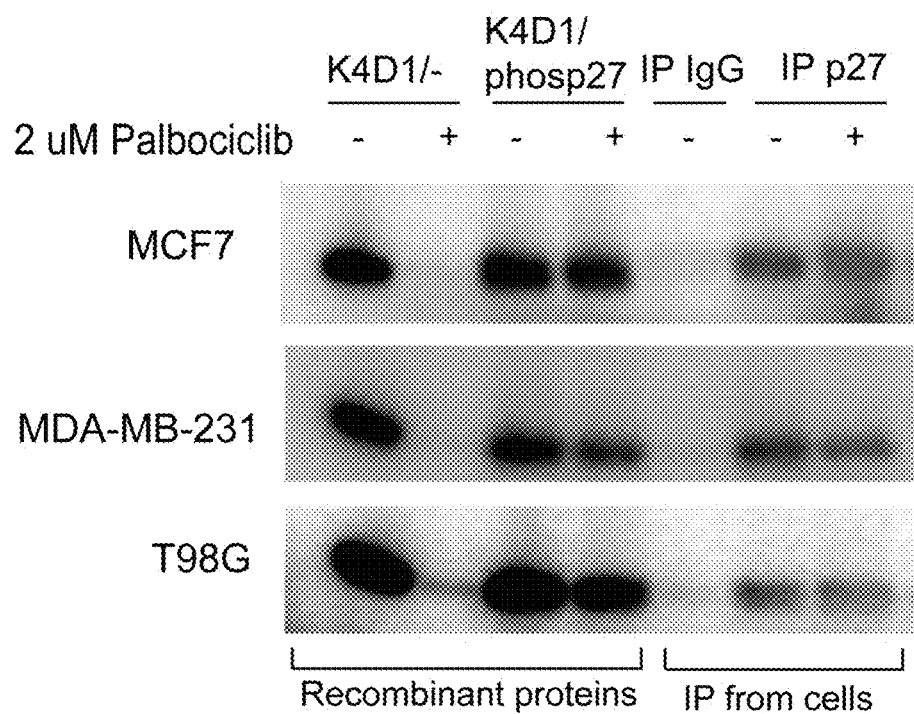
FIG. 1E shows the endogenous p27-Cdk4-CycD1 trimeric complex immunoprecipitated from cells was not sensitive to palbociclib inhibition.

It was found that 1) Cdk4-CycD dimeric complex had high phosphorylation activity specifically for Rb; 2) the wild-type p27-Cdk4-CycD1 trimeric complex with unphosphorylated p27 (e.g., complexes (iii) and (iv) described above) was inhibited; and 3) the wild-type p27-Cdk4-CycD1 trimeric complex with phosphorylated p27 (e.g., complexes (v) and (vi) described above) and the engineered p27-Cdk4-CycD1 trimeric complex (e.g., complexes (vii) and (viii) described above) had phosphorylation activity toward all substrates. Through additional steady state kinetic analysis (FIGS. 1B and 1C), it was found that the engineered p27-Cdk4-CycD1 trimeric complex (e.g., complexes (vii) and (viii) described above) had a reduced KM for ATP. It was also found in a kinase assay that the wild-type p27-Cdk4-CycD1 trimeric complex with phosphorylated p27 and the engineered p27 with Y74E, Y88E, and Y89E-Cdk4-CycD1 trimeric complex were resistant to palbociclib inhibition (FIG. 1D). Compared to the data in FIG. 1D, which used recombinantly expressed proteins in a cell-free system, FIG. 1E shows that endogenous p27-Cdk4-CycD1 trimeric complex immunoprecipitated from cells was also not sensitive to palbociclib inhibition. Indicated cell lysates were immunoprecipitated with control or anti-p27 antibody, and the activity of the immunoprecipitate was used to phosphorylate Rb771-928 with $^{32}$P-ATP in the absence or presence of palbociclib. Reactions with the indicated recombinant dimer (K4D1/−) or trimer (K4D1/phosp27) enzymes are shown for comparison in the first four lanes of each SDS-PAGE gel in FIG. 1E. MCF7 and MDA-MB-231 cells are Rb-positive and palbociclib-sensitive breast cancer cells that differ in estrogen receptor status. T98G cells are glioma cells that are relatively less sensitive to palbociclib.

REFERENCES

1. Dick F A, Rubin S M. Molecular mechanisms underlying RB protein function. *Nat Rev Mol Cell Biol*. 2013; 14(5): 297-306. PubMed PMID: 23594950; PubMed Central PMCID: PMCPMC4754300.
2. Dyson N J. RB1: a prototype tumor suppressor and an enigma. *Genes Dev*. 2016; 30(13):1492-502. PubMed PMID: 27401552; PubMed Central PMCID: PMCPMC4949322.
3. Finn R S, Martin M, Rugo H S, Jones S, Im S A, Gelmon K, Harbeck N, Lipatov O N, Walshe J M, Moulder S, Gauthier E, Lu D R, Randolph S, Dieras V, Slamon D J. Palbociclib and Letrozole in *Advanced Breast Cancer. N Engl J Med*. 2016; 375(20):1925-36. PubMed PMID: 27959613.
4. Sherr C J. A New Cell-Cycle Target in Cancer-Inhibiting Cyclin D-Dependent Kinases 4 and 6. *N Engl J Med*. 2016; 375(20):1920-3. PubMed PMID: 27959598.
5. Sherr C J, Beach D, Shapiro G I. Targeting CDK4 and CDK6: From Discovery to Therapy. *Cancer Discov*. 2016; 6(4):353-67. PubMed PMID: 26658964; PubMed Central PMCID: PMCPMC4821753.
6. Dickler M N, Tolaney S M, Rugo H S, Cortes J, Dieras V, Patt D, Wildiers H, Hudis C A, O'Shaughnessy J, Zamora E, Yardley D A, Frenzel M, Koustenis A, Baselga J. MONARCH 1, A Phase II Study of Abemaciclib, a CDK4 and CDK6 Inhibitor, as a Single Agent, in Patients with Refractory HR(+)/HER2(−) Metastatic Breast Cancer. *Clin Cancer Res*. 2017; 23(17):5218-24. PubMed PMID: 28533223; PubMed Central PMCID: PMCPMC5581697.
7. He S, Roberts P J, Sorrentino J A, Bisi J E, Storrie-White H, Tiessen R G, Makhuli K M, Wargin W A, Tadema H, van Hoogdalem E J, Strum J C, Malik R, Sharpless N E. Transient CDK4/6 inhibition protects hematopoietic stem cells from chemotherapy-induced exhaustion. *Sci Transl Med*. 2017; 9(387). PubMed PMID: 28446688.
8. Xu H, Yu S, Liu Q, Yuan X, Mani S, Pestell R G, Wu K. Recent advances of highly selective CDK4/6 inhibitors in breast cancer. *J Hematol Oncol*. 2017; 10(1):97. PubMed PMID: 28438180; PubMed Central PMCID: PMCPMC5404666.
9. Bagui T K, Jackson R J, Agrawal D, Pledger W J. Analysis of cyclin D3-cdk4 complexes in fibroblasts expressing and lacking p27(kip1) and p21(cip1). *Mol Cell Biol*. 2000; 20(23):8748-57. PubMed PMID: 11073976; PubMed Central PMCID: PMCPMC86501.
10. Kato A, Takahashi H, Takahashi Y, Matsushime H. Inactivation of the cyclin D-dependent kinase in the rat fibroblast cell line, 3Y1, induced by contact inhibition. *J Biol Chem*. 1997; 272(12):8065-70. PubMed PMID: 9065480.
11. Kato J Y, Matsuoka M, Polyak K, Massague J, Sherr C J. Cyclic AMP-induced G1 phase arrest mediated by an inhibitor (p27Kip1) of cyclin-dependent kinase 4 activation. *Cell*. 1994; 79(3):487-96. PubMed PMID: 7954814.
12. Ladha M H, Lee K Y, Upton T M, Reed M F, Ewen M E. Regulation of exit from quiescence by p27 and cyclin D1-CDK4. *Mol Cell Biol*. 1998; 18(11):6605-15. PubMed PMID: 9774675; PubMed Central PMCID: PMCPMC109245.
13. Toyoshima H, Hunter T. p27, a novel inhibitor of G1 cyclin-Cdk protein kinase activity, is related to p21. *Cell*. 1994; 78(1):67-74. PubMed PMID: 8033213.
14. Bagui T K, Mohapatra S, Haura E, Pledger W J. P27Kip1 and p21Cip1 are not required for the formation of active D cyclin-cdk4 complexes. *Mol Cell Biol*. 2003; 23(20): 7285-90. PubMed PMID: 14517297; PubMed Central PMCID: PMCPMC230308.
15. Cheng M, Olivier P, Diehl J A, Fero M, Roussel M F, Roberts J M, Sherr C J. The p21(Cip1) and p27(Kip1) CDK 'inhibitors' are essential activators of cyclin D-dependent kinases in murine fibroblasts. *EMBO J*. 1999; 18(6):1571-83. PubMed PMID: 10075928; PubMed Central PMCID: PMCPMC1171245.
16. LaBaer J, Garrett M D, Stevenson L F, Slingerland J M, Sandhu C, Chou H S, Fattaey A, Harlow E. New functional activities for the p21 family of CDK inhibitors. *Genes Dev.* 1997; 11 (7): 847-62. PubMed PMID: 9106657.
17. Parry D, Mahony D, Wills K, Lees E. Cyclin D-CDK subunit arrangement is dependent on the availability of competing INK4 and p21 class inhibitors. *Mol Cell Biol.* 1999; 19(3):1775-83. PubMed PMID: 10022865; PubMed Central PMCID: PMCPMC83971.
18. Soos T J, Kiyokawa H, Yan J S, Rubin M S, Giordano A, DeBlasio A, Bottega S, Wong B, Mendelsohn J, Koff A. Formation of p27-CDK complexes during the human mitotic cell cycle. *Cell Growth Differ.* 1996; 7(2):135-46. PubMed PMID: 8822197.
19. Grimmler M, Wang Y, Mund T, Cilensek Z, Keidel E M, Waddell M B, Jakel H, Kullmann M, Kriwacki R W, Hengst L. Cdk-inhibitory activity and stability of p27Kip1 are directly regulated by oncogenic tyrosine kinases. *Cell.* 2007; 128(2):269-80. PubMed PMID: 17254966.
20. James M K, Ray A, Leznova D, Blain S W. Differential modification of p27Kip1 controls its cyclin D-cdk4 inhibitory activity. *Mol Cell Biol.* 2008; 28(1):498-510. PubMed PMID: 17908796; PubMed Central PMCID: PMCPMC2223302.
21. Patel P, Asbach B, Shteyn E, Gomez C, Coltoff A, Bhuyan S, Tyner A L, Wagner R, Blain S W. Brk/Protein tyrosine kinase 6 phosphorylates p27KIP1, regulating the activity of cyclin D-cyclin-dependent kinase 4. *Mol Cell Biol.* 2015; 35(9):1506-22. PubMed PMID: 25733683; PubMed Central PMCID: PMCPMC4387217.

What is claimed:

1. A polypeptide comprising an engineered p27, or a fragment thereof, wherein the engineered p27 comprises amino acid substitutions at positions Y74, Y88, and Y89, wherein the amino acid substitution at position Y74 is Y74E, Y74D, or Y74R, the amino acid substitution at Y88 is Y88E or Y88D, and the amino acid substitution at Y89 is Y89E or Y89D, wherein the engineered p27 forms a trimeric protein complex with (i) a cyclin-dependent kinase 4 (Cdk4) or a variant thereof, or a Cdk6 or a variant thereof, and (ii) a cyclin D (CycD) or a variant thereof, and wherein the amino acid positions are determined with reference to the sequence of SEQ ID NO: 1, wherein the engineered p27 comprises a sequence having at least 90% sequence identity to the sequence of SEQ ID NO: 1.

2. The polypeptide of claim 1, wherein the engineered p27 comprises a sequence of (SEQ ID NO: 59)
KPSACRNLFGPVDHEELTRDLEKHCRDMEEASQRKWNFDFQNHKPLEGK
X$_1$EWQEVEKGSLPEFX$_2$X$_3$RPPRPPKGA, wherein X$_1$ is E, D, or R; X$_2$ is E, or D; and X$_3$ is E, or D.

3. The polypeptide of claim 2, wherein the engineered p27 comprises a sequence having at least 90% sequence identity to a sequence comprising SEQ ID NO: 36 or 34.

* * * * *

SEQUENCE LISTING

```
<160> NUMBER OF SEQ ID NOS: 73

<210> SEQ ID NO 1
<211> LENGTH: 198
<212> TYPE: PRT
<213> ORGANISM: Unknown
<220> FEATURE:
<223> OTHER INFORMATION: Description of Unknown:
      p27 sequence

<400> SEQUENCE: 1

Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
        195

<210> SEQ ID NO 2
<211> LENGTH: 82
<212> TYPE: PRT
<213> ORGANISM: Unknown
```

```
<220> FEATURE:
<223> OTHER INFORMATION: Description of Unknown:
      p27 sequence

<400> SEQUENCE: 2

Lys Pro Ser Ala Cys Arg Asn Leu Phe Gly Pro Val Asp His Glu Glu
1               5                   10                  15

Leu Thr Arg Asp Leu Glu Lys His Cys Arg Asp Met Glu Glu Ala Ser
            20                  25                  30

Gln Arg Lys Trp Asn Phe Asp Phe Gln Asn His Lys Pro Leu Glu Gly
        35                  40                  45

Lys Tyr Glu Trp Gln Glu Val Glu Lys Gly Ser Leu Pro Glu Phe Tyr
    50                  55                  60

Tyr Arg Pro Pro Arg Pro Pro Lys Gly Ala Cys Lys Val Pro Ala Gln
65                  70                  75                  80

Glu Ser

<210> SEQ ID NO 3
<211> LENGTH: 74
<212> TYPE: PRT
<213> ORGANISM: Unknown
<220> FEATURE:
<223> OTHER INFORMATION: Description of Unknown:
      p27 sequence

<400> SEQUENCE: 3

Lys Pro Ser Ala Cys Arg Asn Leu Phe Gly Pro Val Asp His Glu Glu
1               5                   10                  15

Leu Thr Arg Asp Leu Glu Lys His Cys Arg Asp Met Glu Glu Ala Ser
            20                  25                  30

Gln Arg Lys Trp Asn Phe Asp Phe Gln Asn His Lys Pro Leu Glu Gly
        35                  40                  45

Lys Tyr Glu Trp Gln Glu Val Glu Lys Gly Ser Leu Pro Glu Phe Tyr
    50                  55                  60

Tyr Arg Pro Pro Arg Pro Pro Lys Gly Ala
65                  70

<210> SEQ ID NO 4
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
```

```
                   100                 105                 110
Arg Pro Ala Ala Pro Leu Ile Gly Ala Pro Ala Asn Ser Glu Asp Thr
            115                 120                 125

His Leu Val Asp Pro Lys Thr Asp Pro Ser Asp Ser Gln Thr Gly Leu
130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
            195

<210> SEQ ID NO 5
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Lys Pro Ser Ala Cys Arg Asn Leu Phe Gly Pro Val Asp His Glu Glu
1               5                   10                  15

Leu Thr Arg Asp Leu Glu Lys His Cys Arg Asp Met Glu Glu Ala Ser
                20                  25                  30

Gln Arg Lys Trp Asn Phe Asp Phe Gln Asn His Lys Pro Leu Glu Gly
            35                  40                  45

Lys Glu Glu Trp Gln Glu Val Glu Lys Gly Ser Leu Pro Glu Phe Tyr
        50                  55                  60

Tyr Arg Pro Pro Arg Pro Pro Lys Gly Ala Cys Lys Val Pro Ala Gln
65                  70                  75                  80

Glu Ser

<210> SEQ ID NO 6
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Lys Pro Ser Ala Cys Arg Asn Leu Phe Gly Pro Val Asp His Glu Glu
1               5                   10                  15

Leu Thr Arg Asp Leu Glu Lys His Cys Arg Asp Met Glu Glu Ala Ser
                20                  25                  30

Gln Arg Lys Trp Asn Phe Asp Phe Gln Asn His Lys Pro Leu Glu Gly
            35                  40                  45

Lys Glu Glu Trp Gln Glu Val Glu Lys Gly Ser Leu Pro Glu Phe Tyr
        50                  55                  60

Tyr Arg Pro Pro Arg Pro Pro Lys Gly Ala
65                  70

<210> SEQ ID NO 7
<211> LENGTH: 198
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 7

Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
50                  55                  60

Gln Asn His Lys Pro Leu Glu Gly Lys Asp Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
            195

<210> SEQ ID NO 8
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Lys Pro Ser Ala Cys Arg Asn Leu Phe Gly Pro Val Asp His Glu Glu
1               5                   10                  15

Leu Thr Arg Asp Leu Glu Lys His Cys Arg Asp Met Glu Glu Ala Ser
            20                  25                  30

Gln Arg Lys Trp Asn Phe Asp Phe Gln Asn His Lys Pro Leu Glu Gly
        35                  40                  45

Lys Asp Glu Trp Gln Glu Val Glu Lys Gly Ser Leu Pro Glu Phe Tyr
50                  55                  60

Tyr Arg Pro Pro Arg Pro Pro Lys Gly Ala Cys Lys Val Pro Ala Gln
65                  70                  75                  80

Glu Ser

<210> SEQ ID NO 9
<211> LENGTH: 74
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 9

Lys Pro Ser Ala Cys Arg Asn Leu Phe Gly Pro Val Asp His Glu Glu
1               5                   10                  15

Leu Thr Arg Asp Leu Glu Lys His Cys Arg Asp Met Glu Glu Ala Ser
            20                  25                  30

Gln Arg Lys Trp Asn Phe Asp Phe Gln Asn His Lys Pro Leu Glu Gly
        35                  40                  45

Lys Asp Glu Trp Gln Glu Val Glu Lys Gly Ser Leu Pro Glu Phe Tyr
    50                  55                  60

Tyr Arg Pro Pro Arg Pro Lys Gly Ala
65                  70

<210> SEQ ID NO 10
<211> LENGTH: 198
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 10

Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Arg Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
        195

<210> SEQ ID NO 11
<211> LENGTH: 82
<212> TYPE: PRT
<213> ORGANISM: Artificial Sequence
<220> FEATURE:
<223> OTHER INFORMATION: Description of Artificial Sequence: Synthetic
    polypeptide -continued

```
<400> SEQUENCE: 11

Lys Pro Ser Ala Cys Arg Asn Leu Phe Gly Pro Val Asp His Glu Glu
1               5                   10                  15

Leu Thr Arg Asp Leu Glu Lys His Cys Arg Asp Met Glu Glu Ala Ser
                20                  25                  30

Gln Arg Lys Trp Asn Phe Asp Phe Gln Asn His Lys Pro Leu Glu Gly
            35                  40                  45

Lys Arg Glu Trp Gln Glu Val Glu Lys Gly Ser Leu Pro Glu Phe Tyr
        50                  55                  60

Tyr Arg Pro Pro Arg Pro Pro Lys Gly Ala Cys Lys Val Pro Ala Gln
65                  70                  75                  80

Glu Ser

<210> SEQ ID NO 12
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Lys Pro Ser Ala Cys Arg Asn Leu Phe Gly Pro Val Asp His Glu Glu
1               5                   10                  15

Leu Thr Arg Asp Leu Glu Lys His Cys Arg Asp Met Glu Glu Ala Ser
                20                  25                  30

Gln Arg Lys Trp Asn Phe Asp Phe Gln Asn His Lys Pro Leu Glu Gly
            35                  40                  45

Lys Arg Glu Trp Gln Glu Val Glu Lys Gly Ser Leu Pro Glu Phe Tyr
        50                  55                  60

Tyr Arg Pro Pro Arg Pro Pro Lys Gly Ala
65                  70

<210> SEQ ID NO 13
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
                20                  25                  30

Phe Gly Pro Val Asp His Glu Glu Leu Thr Arg Asp Leu Glu Lys His
            35                  40                  45

Cys Arg Asp Met Glu Glu Ala Ser Gln Arg Lys Trp Asn Phe Asp Phe
        50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Arg Pro Arg Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125
```

```
His Leu Val Asp Pro Lys Thr Asp Pro Ser Asp Ser Gln Thr Gly Leu
        130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
                180                 185                 190

Leu Arg Arg Arg Gln Thr
            195

<210> SEQ ID NO 14
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Lys Pro Ser Ala Cys Arg Asn Leu Phe Gly Pro Val Asp His Glu Glu
1               5                   10                  15

Leu Thr Arg Asp Leu Glu Lys His Cys Arg Asp Met Glu Glu Ala Ser
                20                  25                  30

Gln Arg Lys Trp Asn Phe Asp Phe Gln Asn His Lys Pro Leu Glu Gly
            35                  40                  45

Lys Tyr Glu Trp Gln Glu Val Glu Lys Gly Ser Leu Pro Glu Phe Glu
        50                  55                  60

Tyr Arg Pro Pro Arg Pro Pro Lys Gly Ala Cys Lys Val Pro Ala Gln
65                  70                  75                  80

Glu Ser

<210> SEQ ID NO 15
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Lys Pro Ser Ala Cys Arg Asn Leu Phe Gly Pro Val Asp His Glu Glu
1               5                   10                  15

Leu Thr Arg Asp Leu Glu Lys His Cys Arg Asp Met Glu Glu Ala Ser
                20                  25                  30

Gln Arg Lys Trp Asn Phe Asp Phe Gln Asn His Lys Pro Leu Glu Gly
            35                  40                  45

Lys Tyr Glu Trp Gln Glu Val Glu Lys Gly Ser Leu Pro Glu Phe Glu
        50                  55                  60

Tyr Arg Pro Pro Arg Pro Pro Lys Gly Ala
65                  70

<210> SEQ ID NO 16
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 16

Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Val Glu
65                  70                  75                  80

Lys Gly Ser Leu Pro Glu Phe Asp Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
        195

<210> SEQ ID NO 17
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Lys Pro Ser Ala Cys Arg Asn Leu Phe Gly Pro Val Asp His Glu Glu
1               5                   10                  15

Leu Thr Arg Asp Leu Glu Lys His Cys Arg Asp Met Glu Glu Ala Ser
            20                  25                  30

Gln Arg Lys Trp Asn Phe Asp Phe Gln Asn His Lys Pro Leu Glu Gly
        35                  40                  45

Lys Tyr Glu Trp Gln Val Glu Lys Gly Ser Leu Pro Glu Phe Asp
    50                  55                  60

Tyr Arg Pro Pro Arg Pro Pro Lys Gly Ala Cys Lys Val Pro Ala Gln
65                  70                  75                  80

Glu Ser

<210> SEQ ID NO 18
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Lys Pro Ser Ala Cys Arg Asn Leu Phe Gly Pro Val Asp His Glu Glu
1               5                   10                  15

Leu Thr Arg Asp Leu Glu Lys His Cys Arg Asp Met Glu Glu Ala Ser
            20                  25                  30

Gln Arg Lys Trp Asn Phe Asp Phe Gln Asn His Lys Pro Leu Glu Gly
            35                  40                  45

Lys Tyr Glu Trp Gln Glu Val Glu Lys Gly Ser Leu Pro Glu Phe Asp
        50                  55                  60

Tyr Arg Pro Pro Arg Pro Pro Lys Gly Ala
65                  70
```

<210> SEQ ID NO 19
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
            35                  40                  45

Cys Arg Asp Met Glu Glu Ala Ser Gln Arg Lys Trp Asn Phe Asp Phe
        50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Glu Arg Pro Arg Pro Pro Lys
            85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
            115                 120                 125

His Leu Val Asp Pro Lys Thr Asp Pro Ser Asp Ser Gln Thr Gly Leu
        130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
        195
```

<210> SEQ ID NO 20
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Lys Pro Ser Ala Cys Arg Asn Leu Phe Gly Pro Val Asp His Glu Glu
1               5                   10                  15
```

Leu Thr Arg Asp Leu Glu Lys His Cys Arg Asp Met Glu Glu Ala Ser
            20                  25                  30

Gln Arg Lys Trp Asn Phe Asp Phe Gln Asn His Lys Pro Leu Glu Gly
        35                  40                  45

Lys Tyr Glu Trp Gln Glu Val Glu Lys Gly Ser Leu Pro Glu Phe Tyr
    50                  55                  60

Glu Arg Pro Pro Arg Pro Pro Lys Gly Ala Cys Lys Val Pro Ala Gln
65                  70                  75                  80

Glu Ser

<210> SEQ ID NO 21
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Lys Pro Ser Ala Cys Arg Asn Leu Phe Gly Pro Val Asp His Glu Glu
1               5                   10                  15

Leu Thr Arg Asp Leu Glu Lys His Cys Arg Asp Met Glu Glu Ala Ser
            20                  25                  30

Gln Arg Lys Trp Asn Phe Asp Phe Gln Asn His Lys Pro Leu Glu Gly
        35                  40                  45

Lys Tyr Glu Trp Gln Glu Val Glu Lys Gly Ser Leu Pro Glu Phe Tyr
    50                  55                  60

Glu Arg Pro Pro Arg Pro Pro Lys Gly Ala
65                  70

<210> SEQ ID NO 22
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Asp Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

```
Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
            165                 170                 175

Gly Ser Pro Asn Ala Gly Ser Val Glu Gln Thr Pro Lys Lys Pro Gly
        180                 185                 190

Leu Arg Arg Arg Gln Thr
            195
```

<210> SEQ ID NO 23
<211> LENGTH: 82
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Lys Pro Ser Ala Cys Arg Asn Leu Phe Gly Pro Val Asp His Glu Glu
1               5                   10                  15

Leu Thr Arg Asp Leu Glu Lys His Cys Arg Asp Met Glu Glu Ala Ser
            20                  25                  30

Gln Arg Lys Trp Asn Phe Asp Phe Gln Asn His Lys Pro Leu Glu Gly
        35                  40                  45

Lys Tyr Glu Trp Gln Glu Val Glu Lys Gly Ser Leu Pro Glu Phe Tyr
    50                  55                  60

Asp Arg Pro Pro Arg Pro Pro Lys Gly Ala Cys Lys Val Pro Ala Gln
65                  70                  75                  80

Glu Ser
```

<210> SEQ ID NO 24
<211> LENGTH: 74
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Lys Pro Ser Ala Cys Arg Asn Leu Phe Gly Pro Val Asp His Glu Glu
1               5                   10                  15

Leu Thr Arg Asp Leu Glu Lys His Cys Arg Asp Met Glu Glu Ala Ser
            20                  25                  30

Gln Arg Lys Trp Asn Phe Asp Phe Gln Asn His Lys Pro Leu Glu Gly
        35                  40                  45

Lys Tyr Glu Trp Gln Glu Val Glu Lys Gly Ser Leu Pro Glu Phe Tyr
    50                  55                  60

Asp Arg Pro Pro Arg Pro Pro Lys Gly Ala
65                  70
```

<210> SEQ ID NO 25
<211> LENGTH: 198
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Met Ser Asn Val Arg Val Ser Asn Gly Ser Pro Ser Leu Glu Arg Met
1               5                   10                  15
```

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
 50                  55                  60

Gln Asn His Lys Pro Leu Glu Gly Lys Glu Glu Trp Gln Glu Val Glu
 65                  70                  75                  80

Lys Gly Ser Leu Pro Glu Phe Glu Tyr Arg Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
            115                 120                 125

His Leu Val Asp Pro Lys Thr Asp Pro Ser Asp Ser Gln Thr Gly Leu
130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
            195

<210> SEQ ID NO 26
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Lys Pro Ser Ala Cys Arg Asn Leu Phe Gly Pro Val Asp His Glu Glu
1               5                   10                  15

Leu Thr Arg Asp Leu Glu Lys His Cys Arg Asp Met Glu Glu Ala Ser
            20                  25                  30

Gln Arg Lys Trp Asn Phe Asp Phe Gln Asn His Lys Pro Leu Glu Gly
        35                  40                  45

Lys Glu Glu Trp Gln Glu Val Glu Lys Gly Ser Leu Pro Glu Phe Glu
 50                  55                  60

Tyr Arg Pro Arg Pro Pro Lys Gly Ala Cys Lys Val Pro Ala Gln
 65                  70                  75                  80

Glu Ser

<210> SEQ ID NO 27
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Lys Pro Ser Ala Cys Arg Asn Leu Phe Gly Pro Val Asp His Glu Glu
1               5                   10                  15

```
Leu Thr Arg Asp Leu Glu Lys His Cys Arg Asp Met Glu Glu Ala Ser
            20                  25                  30

Gln Arg Lys Trp Asn Phe Asp Phe Gln Asn His Lys Pro Leu Glu Gly
            35                  40                  45

Lys Glu Glu Trp Gln Glu Val Glu Lys Gly Ser Leu Pro Glu Phe Glu
        50                  55                  60

Tyr Arg Pro Pro Arg Pro Pro Lys Gly Ala
 65                  70
```

<210> SEQ ID NO 28
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Met Ser Asn Val Arg Val Ser Asn Gly Ser Pro Ser Leu Glu Arg Met
 1               5                  10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Glu Glu Trp Gln Glu Val Glu
65                  70                  75                  80

Lys Gly Ser Leu Pro Glu Phe Tyr Glu Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
        195
```

<210> SEQ ID NO 29
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Lys Pro Ser Ala Cys Arg Asn Leu Phe Gly Pro Val Asp His Glu Glu
 1               5                  10                  15

Leu Thr Arg Asp Leu Glu Lys His Cys Arg Asp Met Glu Glu Ala Ser
            20                  25                  30
```

Gln Arg Lys Trp Asn Phe Asp Phe Gln Asn His Lys Pro Leu Glu Gly
            35                  40                  45

Lys Glu Glu Trp Gln Glu Val Glu Lys Gly Ser Leu Pro Glu Phe Tyr
 50                  55                  60

Glu Arg Pro Pro Arg Pro Pro Lys Gly Ala Cys Lys Val Pro Ala Gln
 65                  70                  75                  80

Glu Ser

<210> SEQ ID NO 30
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Lys Pro Ser Ala Cys Arg Asn Leu Phe Gly Pro Val Asp His Glu Glu
 1               5                  10                  15

Leu Thr Arg Asp Leu Glu Lys His Cys Arg Asp Met Glu Glu Ala Ser
            20                  25                  30

Gln Arg Lys Trp Asn Phe Asp Phe Gln Asn His Lys Pro Leu Glu Gly
            35                  40                  45

Lys Glu Glu Trp Gln Glu Val Glu Lys Gly Ser Leu Pro Glu Phe Tyr
 50                  55                  60

Glu Arg Pro Pro Arg Pro Pro Lys Gly Ala
 65                  70

<210> SEQ ID NO 31
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Ser Asn Val Arg Val Ser Asn Gly Ser Pro Ser Leu Glu Arg Met
 1               5                  10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
            35                  40                  45

Cys Arg Asp Met Glu Glu Ala Ser Gln Arg Lys Trp Asn Phe Asp Phe
 50                  55                  60

Gln Asn His Lys Pro Leu Glu Gly Lys Tyr Glu Trp Gln Glu Val Glu
 65                  70                  75                  80

Lys Gly Ser Leu Pro Glu Phe Glu Arg Pro Pro Arg Pro Pro Lys
                 85                  90                  95

Gly Ala Cys Lys Val Pro Ala Gln Glu Ser Gln Asp Val Ser Gly Ser
                100                 105                 110

Arg Pro Ala Ala Pro Leu Ile Gly Ala Pro Ala Asn Ser Glu Asp Thr
                115                 120                 125

His Leu Val Asp Pro Lys Thr Asp Pro Ser Asp Ser Gln Thr Gly Leu
                130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp 165                 170                 175
Gly Ser Pro Asn Ala Gly Ser Val Glu Gln Thr Pro Lys Lys Pro Gly
                180                 185                 190

Leu Arg Arg Arg Gln Thr
            195

<210> SEQ ID NO 32
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Lys Pro Ser Ala Cys Arg Asn Leu Phe Gly Pro Val Asp His Glu Glu
1               5                   10                  15

Leu Thr Arg Asp Leu Glu Lys His Cys Arg Asp Met Glu Glu Ala Ser
            20                  25                  30

Gln Arg Lys Trp Asn Phe Asp Phe Gln Asn His Lys Pro Leu Glu Gly
        35                  40                  45

Lys Tyr Glu Trp Gln Glu Val Glu Lys Gly Ser Leu Pro Glu Phe Glu
    50                  55                  60

Glu Arg Pro Pro Arg Pro Pro Lys Gly Ala Cys Lys Val Pro Ala Gln
65                  70                  75                  80

Glu Ser

<210> SEQ ID NO 33
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Lys Pro Ser Ala Cys Arg Asn Leu Phe Gly Pro Val Asp His Glu Glu
1               5                   10                  15

Leu Thr Arg Asp Leu Glu Lys His Cys Arg Asp Met Glu Glu Ala Ser
            20                  25                  30

Gln Arg Lys Trp Asn Phe Asp Phe Gln Asn His Lys Pro Leu Glu Gly
        35                  40                  45

Lys Tyr Glu Trp Gln Glu Val Glu Lys Gly Ser Leu Pro Glu Phe Glu
    50                  55                  60

Glu Arg Pro Pro Arg Pro Pro Lys Gly Ala
65                  70

<210> SEQ ID NO 34
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

```
Phe Gly Pro Val Asp His Glu Glu Leu Thr Arg Asp Leu Glu Lys His
            35                  40                  45

Cys Arg Asp Met Glu Glu Ala Ser Gln Arg Lys Trp Asn Phe Asp Phe
 50                  55                  60

Gln Asn His Lys Pro Leu Glu Gly Lys Glu Glu Trp Gln Val Glu
 65                  70                  75                  80

Lys Gly Ser Leu Pro Glu Phe Glu Arg Pro Pro Arg Pro Pro Lys
                 85                  90                  95

Gly Ala Cys Lys Val Pro Ala Gln Glu Ser Gln Asp Val Ser Gly Ser
                100                 105                 110

Arg Pro Ala Ala Pro Leu Ile Gly Ala Pro Ala Asn Ser Glu Asp Thr
            115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
            195

<210> SEQ ID NO 35
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Lys Pro Ser Ala Cys Arg Asn Leu Phe Gly Pro Val Asp His Glu Glu
 1               5                  10                  15

Leu Thr Arg Asp Leu Glu Lys His Cys Arg Asp Met Glu Glu Ala Ser
                20                  25                  30

Gln Arg Lys Trp Asn Phe Asp Phe Gln Asn His Lys Pro Leu Glu Gly
             35                  40                  45

Lys Glu Glu Trp Gln Val Glu Lys Gly Ser Leu Pro Glu Phe Glu
 50                  55                  60

Glu Arg Pro Pro Arg Pro Pro Lys Gly Ala Cys Lys Val Pro Ala Gln
 65                  70                  75                  80

Glu Ser

<210> SEQ ID NO 36
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Lys Pro Ser Ala Cys Arg Asn Leu Phe Gly Pro Val Asp His Glu Glu
 1               5                  10                  15

Leu Thr Arg Asp Leu Glu Lys His Cys Arg Asp Met Glu Glu Ala Ser
                20                  25                  30

Gln Arg Lys Trp Asn Phe Asp Phe Gln Asn His Lys Pro Leu Glu Gly
             35                  40                  45
```

```
                35                  40                  45
Lys Glu Glu Trp Gln Glu Val Glu Lys Gly Ser Leu Pro Glu Phe Glu
     50                  55                  60

Glu Arg Pro Arg Pro Pro Lys Gly Ala
65                  70

<210> SEQ ID NO 37
<211> LENGTH: 303
<212> TYPE: PRT
<213> ORGANISM: Unknown
<220> FEATURE:
<223> OTHER INFORMATION: Description of Unknown:
      Cdk4 sequence

<400> SEQUENCE: 37

Met Ala Thr Ser Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
                20                  25                  30

Ala Leu Lys Ser Val Arg Val Pro Asn Gly Gly Gly Gly Gly Gly Gly
            35                  40                  45

Leu Pro Ile Ser Thr Val Arg Glu Val Ala Leu Leu Arg Arg Leu Glu
     50                  55                  60

Ala Phe Glu His Pro Asn Val Val Arg Leu Met Asp Val Cys Ala Thr
65                  70                  75                  80

Ser Arg Thr Asp Arg Glu Ile Lys Val Thr Leu Val Phe Glu His Val
                85                  90                  95

Asp Gln Asp Leu Arg Thr Tyr Leu Asp Lys Ala Pro Pro Pro Gly Leu
            100                 105                 110

Pro Ala Glu Thr Ile Lys Asp Leu Met Arg Gln Phe Leu Arg Gly Leu
        115                 120                 125

Asp Phe Leu His Ala Asn Cys Ile Val His Arg Asp Leu Lys Pro Glu
    130                 135                 140

Asn Ile Leu Val Thr Ser Gly Gly Thr Val Lys Leu Ala Asp Phe Gly
145                 150                 155                 160

Leu Ala Arg Ile Tyr Ser Tyr Gln Met Ala Leu Thr Pro Val Val Val
                165                 170                 175

Thr Leu Trp Tyr Arg Ala Pro Glu Val Leu Leu Gln Ser Thr Tyr Ala
            180                 185                 190

Thr Pro Val Asp Met Trp Ser Val Gly Cys Ile Phe Ala Glu Met Phe
        195                 200                 205

Arg Arg Lys Pro Leu Phe Cys Gly Asn Ser Glu Ala Asp Gln Leu Gly
    210                 215                 220

Lys Ile Phe Asp Leu Ile Gly Leu Pro Pro Glu Asp Asp Trp Pro Arg
225                 230                 235                 240

Asp Val Ser Leu Pro Arg Gly Ala Phe Pro Pro Arg Gly Pro Arg Pro
                245                 250                 255

Val Gln Ser Val Val Pro Glu Met Glu Glu Ser Gly Ala Gln Leu Leu
            260                 265                 270

Leu Glu Met Leu Thr Phe Asn Pro His Lys Arg Ile Ser Ala Phe Arg
        275                 280                 285

Ala Leu Gln His Ser Tyr Leu His Lys Asp Glu Gly Asn Pro Glu
    290                 295                 300

<210> SEQ ID NO 38
<211> LENGTH: 303
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Ala Thr Ser Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
                20                  25                  30

Ala Leu Lys Ser Val Arg Val Pro Asn Gly Gly Gly Gly Gly Gly Gly
            35                  40                  45

Leu Pro Ile Ser Thr Val Arg Glu Val Ala Leu Leu Arg Arg Leu Glu
    50                  55                  60

Ala Phe Glu His Pro Asn Val Val Arg Leu Met Asp Val Cys Ala Thr
65                  70                  75                  80

Ser Arg Thr Asp Arg Glu Ile Lys Val Thr Leu Val Phe Glu His Val
                85                  90                  95

Asp Gln Asp Leu Arg Thr Tyr Leu Asp Lys Ala Pro Pro Pro Gly Leu
                100                 105                 110

Pro Ala Glu Thr Ile Lys Asp Leu Met Arg Gln Phe Leu Arg Gly Leu
            115                 120                 125

Asp Phe Leu His Ala Asn Cys Ile Val His Arg Asp Leu Lys Pro Glu
130                 135                 140

Asn Ile Leu Val Thr Ser Gly Gly Thr Val Lys Leu Ala Asp Phe Gly
145                 150                 155                 160

Leu Ala Arg Ile Tyr Ser Tyr Gln Met Ala Leu Asp Pro Val Val Val
                165                 170                 175

Thr Leu Trp Tyr Arg Ala Pro Glu Val Leu Leu Gln Ser Thr Tyr Ala
            180                 185                 190

Thr Pro Val Asp Met Trp Ser Val Gly Cys Ile Phe Ala Glu Met Phe
        195                 200                 205

Arg Arg Lys Pro Leu Phe Cys Gly Asn Ser Glu Ala Asp Gln Leu Gly
210                 215                 220

Lys Ile Phe Asp Leu Ile Gly Leu Pro Pro Glu Asp Asp Trp Pro Arg
225                 230                 235                 240

Asp Val Ser Leu Pro Arg Gly Ala Phe Pro Pro Arg Gly Pro Arg Pro
                245                 250                 255

Val Gln Ser Val Val Pro Glu Met Glu Glu Ser Gly Ala Gln Leu Leu
            260                 265                 270

Leu Glu Met Leu Thr Phe Asn Pro His Lys Arg Ile Ser Ala Phe Arg
        275                 280                 285

Ala Leu Gln His Ser Tyr Leu His Lys Asp Glu Gly Asn Pro Glu
290                 295                 300

<210> SEQ ID NO 39
<211> LENGTH: 303
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Ala Thr Ser Arg Tyr Glu Pro Val Ala Glu Ile Gly Val Gly Ala
1               5                   10                  15
```

```
Tyr Gly Thr Val Tyr Lys Ala Arg Asp Pro His Ser Gly His Phe Val
            20                  25                  30

Ala Leu Lys Ser Val Arg Val Pro Asn Gly Gly Gly Gly Gly Gly Gly
            35                  40                  45

Leu Pro Ile Ser Thr Val Arg Glu Val Ala Leu Leu Arg Arg Leu Glu
 50                  55                  60

Ala Phe Glu His Pro Asn Val Val Arg Leu Met Asp Val Cys Ala Thr
 65                  70                  75                  80

Ser Arg Thr Asp Arg Glu Ile Lys Val Thr Leu Val Phe Glu His Val
                85                  90                  95

Asp Gln Asp Leu Arg Thr Tyr Leu Asp Lys Ala Pro Pro Gly Leu
            100                 105                 110

Pro Ala Glu Thr Ile Lys Asp Leu Met Arg Gln Phe Leu Arg Gly Leu
            115                 120                 125

Asp Phe Leu His Ala Asn Cys Ile Val His Arg Asp Leu Lys Pro Glu
            130                 135                 140

Asn Ile Leu Val Thr Ser Gly Gly Thr Val Lys Leu Ala Asp Phe Gly
145                 150                 155                 160

Leu Ala Arg Ile Tyr Ser Tyr Gln Met Ala Leu Glu Pro Val Val
            165                 170                 175

Thr Leu Trp Tyr Arg Ala Pro Glu Val Leu Leu Gln Ser Thr Tyr Ala
            180                 185                 190

Thr Pro Val Asp Met Trp Ser Val Gly Cys Ile Phe Ala Glu Met Phe
            195                 200                 205

Arg Arg Lys Pro Leu Phe Cys Gly Asn Ser Glu Ala Asp Gln Leu Gly
210                 215                 220

Lys Ile Phe Asp Leu Ile Gly Leu Pro Pro Glu Asp Asp Trp Pro Arg
225                 230                 235                 240

Asp Val Ser Leu Pro Arg Gly Ala Phe Pro Pro Arg Gly Pro Arg Pro
                245                 250                 255

Val Gln Ser Val Val Pro Glu Met Glu Glu Ser Gly Ala Gln Leu Leu
            260                 265                 270

Leu Glu Met Leu Thr Phe Asn Pro His Lys Arg Ile Ser Ala Phe Arg
            275                 280                 285

Ala Leu Gln His Ser Tyr Leu His Lys Asp Glu Gly Asn Pro Glu
            290                 295                 300

<210> SEQ ID NO 40
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Ala Thr Ser Arg Tyr Glu Pro Val Ala Glu Ile Gly Val Gly Ala
 1               5                  10                  15

Tyr Gly Thr Val Tyr Lys Ala Arg Asp Pro His Ser Gly His Phe Val
            20                  25                  30

Ala Leu Lys Ser Val Arg Val Pro Asn Gly Glu Gly Leu Pro Ile
            35                  40                  45

Ser Thr Val Arg Glu Val Ala Leu Leu Arg Arg Leu Glu Ala Phe Glu
 50                  55                  60

His Pro Asn Val Val Arg Leu Met Asp Val Cys Ala Thr Ser Arg Thr
 65                  70                  75                  80
```

Asp Arg Glu Ile Lys Val Thr Leu Val Phe Glu His Val Asp Gln Asp
            85                  90                  95

Leu Arg Thr Tyr Leu Asp Lys Ala Pro Pro Gly Leu Pro Ala Glu
        100                 105                 110

Thr Ile Lys Asp Leu Met Arg Gln Phe Leu Arg Gly Leu Asp Phe Leu
            115                 120                 125

His Ala Asn Cys Ile Val His Arg Asp Leu Lys Pro Glu Asn Ile Leu
130                 135                 140

Val Thr Ser Gly Gly Thr Val Lys Leu Ala Asp Phe Gly Leu Ala Arg
145                 150                 155                 160

Ile Tyr Ser Tyr Gln Met Ala Leu Thr Pro Val Val Thr Leu Trp
            165                 170                 175

Tyr Arg Ala Pro Glu Val Leu Leu Gln Ser Thr Tyr Ala Thr Pro Val
        180                 185                 190

Asp Met Trp Ser Val Gly Cys Ile Phe Ala Glu Met Phe Arg Arg Lys
            195                 200                 205

Pro Leu Phe Cys Gly Asn Ser Glu Ala Asp Gln Leu Gly Lys Ile Phe
        210                 215                 220

Asp Leu Ile Gly Leu Pro Pro Glu Asp Trp Pro Arg Asp Val Ser
225                 230                 235                 240

Leu Pro Arg Gly Ala Phe Pro Pro Arg Gly Pro Arg Pro Val Gln Ser
            245                 250                 255

Val Val Pro Glu Met Glu Glu Ser Gly Ala Gln Leu Leu Leu Glu Met
            260                 265                 270

Leu Thr Phe Asn Pro His Lys Arg Ile Ser Ala Phe Arg Ala Leu Gln
        275                 280                 285

His Ser Tyr Leu His Lys Asp Glu Gly Asn Pro Glu
        290                 295                 300

<210> SEQ ID NO 41
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Ala Thr Ser Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
            20                  25                  30

Ala Leu Lys Ser Val Arg Val Pro Asn Gly Asp Glu Gly Leu Pro Ile
        35                  40                  45

Ser Thr Val Arg Glu Val Ala Leu Leu Arg Arg Leu Glu Ala Phe Glu
50                  55                  60

His Pro Asn Val Val Arg Leu Met Asp Val Cys Ala Thr Ser Arg Thr
65                  70                  75                  80

Asp Arg Glu Ile Lys Val Thr Leu Val Phe Glu His Val Asp Gln Asp
            85                  90                  95

Leu Arg Thr Tyr Leu Asp Lys Ala Pro Pro Gly Leu Pro Ala Glu
        100                 105                 110

Thr Ile Lys Asp Leu Met Arg Gln Phe Leu Arg Gly Leu Asp Phe Leu
            115                 120                 125

His Ala Asn Cys Ile Val His Arg Asp Leu Lys Pro Glu Asn Ile Leu

```
            130             135             140
Val Thr Ser Gly Gly Thr Val Lys Leu Ala Asp Phe Gly Leu Ala Arg
145                 150                 155                 160

Ile Tyr Ser Tyr Gln Met Ala Leu Thr Pro Val Val Thr Leu Trp
                165                 170                 175

Tyr Arg Ala Pro Glu Val Leu Leu Gln Ser Thr Tyr Ala Thr Pro Val
                180                 185                 190

Asp Met Trp Ser Val Gly Cys Ile Phe Ala Glu Met Phe Arg Arg Lys
                195                 200                 205

Pro Leu Phe Cys Gly Asn Ser Glu Ala Asp Gln Leu Gly Lys Ile Phe
                210                 215                 220

Asp Leu Ile Gly Leu Pro Pro Glu Asp Asp Trp Pro Arg Asp Val Ser
225                 230                 235                 240

Leu Pro Arg Gly Ala Phe Pro Pro Arg Gly Pro Arg Pro Val Gln Ser
                245                 250                 255

Val Val Pro Glu Met Glu Glu Ser Gly Ala Gln Leu Leu Leu Glu Met
                260                 265                 270

Leu Thr Phe Asn Pro His Lys Arg Ile Ser Ala Phe Arg Ala Leu Gln
                275                 280                 285

His Ser Tyr Leu His Lys Asp Glu Gly Asn Pro Glu
                290                 295                 300

<210> SEQ ID NO 42
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Ala Thr Ser Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
                20                  25                  30

Ala Leu Lys Ser Val Arg Val Pro Asn Gly Glu Asp Gly Leu Pro Ile
                35                  40                  45

Ser Thr Val Arg Glu Val Ala Leu Leu Arg Arg Leu Glu Ala Phe Glu
50                  55                  60

His Pro Asn Val Val Arg Leu Met Asp Val Cys Ala Thr Ser Arg Thr
65                  70                  75                  80

Asp Arg Glu Ile Lys Val Thr Leu Val Phe Glu His Val Asp Gln Asp
                85                  90                  95

Leu Arg Thr Tyr Leu Asp Lys Ala Pro Pro Pro Gly Leu Pro Ala Glu
                100                 105                 110

Thr Ile Lys Asp Leu Met Arg Gln Phe Leu Arg Gly Leu Asp Phe Leu
                115                 120                 125

His Ala Asn Cys Ile Val His Arg Asp Leu Lys Pro Glu Asn Ile Leu
                130                 135                 140

Val Thr Ser Gly Gly Thr Val Lys Leu Ala Asp Phe Gly Leu Ala Arg
145                 150                 155                 160

Ile Tyr Ser Tyr Gln Met Ala Leu Thr Pro Val Val Thr Leu Trp
                165                 170                 175

Tyr Arg Ala Pro Glu Val Leu Leu Gln Ser Thr Tyr Ala Thr Pro Val
                180                 185                 190
```

```
Asp Met Trp Ser Val Gly Cys Ile Phe Ala Glu Met Phe Arg Arg Lys
            195                 200                 205

Pro Leu Phe Cys Gly Asn Ser Glu Ala Asp Gln Leu Gly Lys Ile Phe
        210                 215                 220

Asp Leu Ile Gly Leu Pro Pro Glu Asp Asp Trp Pro Arg Asp Val Ser
225                 230                 235                 240

Leu Pro Arg Gly Ala Phe Pro Pro Arg Gly Pro Arg Pro Val Gln Ser
                245                 250                 255

Val Val Pro Glu Met Glu Glu Ser Gly Ala Gln Leu Leu Leu Glu Met
            260                 265                 270

Leu Thr Phe Asn Pro His Lys Arg Ile Ser Ala Phe Arg Ala Leu Gln
        275                 280                 285

His Ser Tyr Leu His Lys Asp Glu Gly Asn Pro Glu
    290                 295                 300

<210> SEQ ID NO 43
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Ala Thr Ser Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
            20                  25                  30

Ala Leu Lys Ser Val Arg Val Pro Asn Gly Asp Asp Gly Leu Pro Ile
        35                  40                  45

Ser Thr Val Arg Glu Val Ala Leu Leu Arg Arg Leu Glu Ala Phe Glu
    50                  55                  60

His Pro Asn Val Val Arg Leu Met Asp Val Cys Ala Thr Ser Arg Thr
65                  70                  75                  80

Asp Arg Glu Ile Lys Val Thr Leu Val Phe Glu His Val Asp Gln Asp
                85                  90                  95

Leu Arg Thr Tyr Leu Asp Lys Ala Pro Pro Pro Gly Leu Pro Ala Glu
            100                 105                 110

Thr Ile Lys Asp Leu Met Arg Gln Phe Leu Arg Gly Leu Asp Phe Leu
        115                 120                 125

His Ala Asn Cys Ile Val His Arg Asp Leu Lys Pro Glu Asn Ile Leu
    130                 135                 140

Val Thr Ser Gly Gly Thr Val Lys Leu Ala Asp Phe Gly Leu Ala Arg
145                 150                 155                 160

Ile Tyr Ser Tyr Gln Met Ala Leu Thr Pro Val Val Val Thr Leu Trp
                165                 170                 175

Tyr Arg Ala Pro Glu Val Leu Leu Gln Ser Thr Tyr Ala Thr Pro Val
            180                 185                 190

Asp Met Trp Ser Val Gly Cys Ile Phe Ala Glu Met Phe Arg Arg Lys
        195                 200                 205

Pro Leu Phe Cys Gly Asn Ser Glu Ala Asp Gln Leu Gly Lys Ile Phe
    210                 215                 220

Asp Leu Ile Gly Leu Pro Pro Glu Asp Asp Trp Pro Arg Asp Val Ser
225                 230                 235                 240

Leu Pro Arg Gly Ala Phe Pro Pro Arg Gly Pro Arg Pro Val Gln Ser
                245                 250                 255
```

Val Val Pro Glu Met Glu Glu Ser Gly Ala Gln Leu Leu Glu Met
            260                 265                 270

Leu Thr Phe Asn Pro His Lys Arg Ile Ser Ala Phe Arg Ala Leu Gln
        275                 280                 285

His Ser Tyr Leu His Lys Asp Glu Gly Asn Pro Glu
        290                 295                 300

<210> SEQ ID NO 44
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Ala Thr Ser Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
            20                  25                  30

Ala Leu Lys Ser Val Arg Val Pro Asn Gly Glu Glu Gly Leu Pro Ile
        35                  40                  45

Ser Thr Val Arg Glu Val Ala Leu Leu Arg Arg Leu Glu Ala Phe Glu
    50                  55                  60

His Pro Asn Val Val Arg Leu Met Asp Val Cys Ala Thr Ser Arg Thr
65                  70                  75                  80

Asp Arg Glu Ile Lys Val Thr Leu Val Phe Glu His Val Asp Gln Asp
                85                  90                  95

Leu Arg Thr Tyr Leu Asp Lys Ala Pro Pro Pro Gly Leu Pro Ala Glu
            100                 105                 110

Thr Ile Lys Asp Leu Met Arg Gln Phe Leu Arg Gly Leu Asp Phe Leu
        115                 120                 125

His Ala Asn Cys Ile Val His Arg Asp Leu Lys Pro Glu Asn Ile Leu
    130                 135                 140

Val Thr Ser Gly Gly Thr Val Lys Leu Ala Asp Phe Gly Leu Ala Arg
145                 150                 155                 160

Ile Tyr Ser Tyr Gln Met Ala Leu Asp Pro Val Val Thr Leu Trp
                165                 170                 175

Tyr Arg Ala Pro Glu Val Leu Leu Gln Ser Thr Tyr Ala Thr Pro Val
            180                 185                 190

Asp Met Trp Ser Val Gly Cys Ile Phe Ala Glu Met Phe Arg Arg Lys
        195                 200                 205

Pro Leu Phe Cys Gly Asn Ser Glu Ala Asp Gln Leu Gly Lys Ile Phe
    210                 215                 220

Asp Leu Ile Gly Leu Pro Pro Glu Asp Asp Trp Pro Arg Asp Val Ser
225                 230                 235                 240

Leu Pro Arg Gly Ala Phe Pro Pro Arg Gly Pro Arg Pro Val Gln Ser
                245                 250                 255

Val Val Pro Glu Met Glu Glu Ser Gly Ala Gln Leu Leu Glu Met
            260                 265                 270

Leu Thr Phe Asn Pro His Lys Arg Ile Ser Ala Phe Arg Ala Leu Gln
        275                 280                 285

His Ser Tyr Leu His Lys Asp Glu Gly Asn Pro Glu
        290                 295                 300

```
<210> SEQ ID NO 45
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45
```

Met Ala Thr Ser Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
                20                  25                  30

Ala Leu Lys Ser Val Arg Val Pro Asn Gly Asp Glu Gly Leu Pro Ile
            35                  40                  45

Ser Thr Val Arg Glu Val Ala Leu Leu Arg Arg Leu Glu Ala Phe Glu
50                  55                  60

His Pro Asn Val Val Arg Leu Met Asp Val Cys Ala Thr Ser Arg Thr
65                  70                  75                  80

Asp Arg Glu Ile Lys Val Thr Leu Val Phe Glu His Val Asp Gln Asp
                85                  90                  95

Leu Arg Thr Tyr Leu Asp Lys Ala Pro Pro Pro Gly Leu Pro Ala Glu
            100                 105                 110

Thr Ile Lys Asp Leu Met Arg Gln Phe Leu Arg Gly Leu Asp Phe Leu
        115                 120                 125

His Ala Asn Cys Ile Val His Arg Asp Leu Lys Pro Glu Asn Ile Leu
130                 135                 140

Val Thr Ser Gly Gly Thr Val Lys Leu Ala Asp Phe Gly Leu Ala Arg
145                 150                 155                 160

Ile Tyr Ser Tyr Gln Met Ala Leu Asp Pro Val Val Val Thr Leu Trp
                165                 170                 175

Tyr Arg Ala Pro Glu Val Leu Leu Gln Ser Thr Tyr Ala Thr Pro Val
            180                 185                 190

Asp Met Trp Ser Val Gly Cys Ile Phe Ala Glu Met Phe Arg Arg Lys
        195                 200                 205

Pro Leu Phe Cys Gly Asn Ser Glu Ala Asp Gln Leu Gly Lys Ile Phe
210                 215                 220

Asp Leu Ile Gly Leu Pro Pro Glu Asp Asp Trp Pro Arg Asp Val Ser
225                 230                 235                 240

Leu Pro Arg Gly Ala Phe Pro Pro Arg Gly Pro Arg Pro Val Gln Ser
                245                 250                 255

Val Val Pro Glu Met Glu Glu Ser Gly Ala Gln Leu Leu Leu Glu Met
            260                 265                 270

Leu Thr Phe Asn Pro His Lys Arg Ile Ser Ala Phe Arg Ala Leu Gln
        275                 280                 285

His Ser Tyr Leu His Lys Asp Glu Gly Asn Pro Glu
290                 295                 300

```
<210> SEQ ID NO 46
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46
```

Met Ala Thr Ser Arg Tyr Glu Pro Val Ala Glu Ile Gly Val Gly Ala

```
                1               5                  10                    15
            Tyr Gly Thr Val Tyr Lys Ala Arg Asp Pro His Ser Gly His Phe Val
                            20                  25                  30

Ala Leu Lys Ser Val Arg Val Pro Asn Gly Glu Asp Gly Leu Pro Ile
                            35                  40                  45

Ser Thr Val Arg Glu Val Ala Leu Leu Arg Arg Leu Glu Ala Phe Glu
                50                      55                  60

His Pro Asn Val Val Arg Leu Met Asp Val Cys Ala Thr Ser Arg Thr
            65                      70                  75                      80

Asp Arg Glu Ile Lys Val Thr Leu Val Phe Glu His Val Asp Gln Asp
                                85                  90                  95

Leu Arg Thr Tyr Leu Asp Lys Ala Pro Pro Gly Leu Pro Ala Glu
                            100                 105                 110

Thr Ile Lys Asp Leu Met Arg Gln Phe Leu Arg Gly Leu Asp Phe Leu
                            115                 120                 125

His Ala Asn Cys Ile Val His Arg Asp Leu Lys Pro Glu Asn Ile Leu
                130                     135                 140

Val Thr Ser Gly Gly Thr Val Lys Leu Ala Asp Phe Gly Leu Ala Arg
            145                     150                 155                     160

Ile Tyr Ser Tyr Gln Met Ala Leu Asp Pro Val Val Thr Leu Trp
                            165                 170                 175

Tyr Arg Ala Pro Glu Val Leu Leu Gln Ser Thr Tyr Ala Thr Pro Val
                            180                 185                 190

Asp Met Trp Ser Val Gly Cys Ile Phe Ala Glu Met Phe Arg Arg Lys
                            195                 200                 205

Pro Leu Phe Cys Gly Asn Ser Glu Ala Asp Gln Leu Gly Lys Ile Phe
                            210                 215                 220

Asp Leu Ile Gly Leu Pro Pro Glu Asp Asp Trp Pro Arg Asp Val Ser
            225                     230                 235                     240

Leu Pro Arg Gly Ala Phe Pro Pro Arg Gly Pro Arg Pro Val Gln Ser
                            245                 250                 255

Val Val Pro Glu Met Glu Glu Ser Gly Ala Gln Leu Leu Leu Glu Met
                            260                 265                 270

Leu Thr Phe Asn Pro His Lys Arg Ile Ser Ala Phe Arg Ala Leu Gln
                            275                 280                 285

His Ser Tyr Leu His Lys Asp Glu Gly Asn Pro Glu
                290                     295                 300

<210> SEQ ID NO 47
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Ala Thr Ser Arg Tyr Glu Pro Val Ala Glu Ile Gly Val Gly Ala
            1               5                   10                  15

Tyr Gly Thr Val Tyr Lys Ala Arg Asp Pro His Ser Gly His Phe Val
                            20                  25                  30

Ala Leu Lys Ser Val Arg Val Pro Asn Gly Asp Asp Gly Leu Pro Ile
                            35                  40                  45

Ser Thr Val Arg Glu Val Ala Leu Leu Arg Arg Leu Glu Ala Phe Glu
                50                      55                  60
```

```
His Pro Asn Val Val Arg Leu Met Asp Val Cys Ala Thr Ser Arg Thr
 65                  70                  75                  80

Asp Arg Glu Ile Lys Val Thr Leu Val Phe Glu His Val Asp Gln Asp
                 85                  90                  95

Leu Arg Thr Tyr Leu Asp Lys Ala Pro Pro Gly Leu Pro Ala Glu
            100                 105                 110

Thr Ile Lys Asp Leu Met Arg Gln Phe Leu Arg Gly Leu Asp Phe Leu
            115                 120                 125

His Ala Asn Cys Ile Val His Arg Asp Leu Lys Pro Glu Asn Ile Leu
130                 135                 140

Val Thr Ser Gly Gly Thr Val Lys Leu Ala Asp Phe Gly Leu Ala Arg
145                 150                 155                 160

Ile Tyr Ser Tyr Gln Met Ala Leu Asp Pro Val Val Thr Leu Trp
            165                 170                 175

Tyr Arg Ala Pro Glu Val Leu Leu Gln Ser Thr Tyr Ala Thr Pro Val
            180                 185                 190

Asp Met Trp Ser Val Gly Cys Ile Phe Ala Glu Met Phe Arg Arg Lys
            195                 200                 205

Pro Leu Phe Cys Gly Asn Ser Glu Ala Asp Gln Leu Gly Lys Ile Phe
        210                 215                 220

Asp Leu Ile Gly Leu Pro Pro Glu Asp Asp Trp Pro Arg Asp Val Ser
225                 230                 235                 240

Leu Pro Arg Gly Ala Phe Pro Pro Arg Gly Pro Arg Pro Val Gln Ser
                245                 250                 255

Val Val Pro Glu Met Glu Glu Ser Gly Ala Gln Leu Leu Leu Glu Met
            260                 265                 270

Leu Thr Phe Asn Pro His Lys Arg Ile Ser Ala Phe Arg Ala Leu Gln
        275                 280                 285

His Ser Tyr Leu His Lys Asp Glu Gly Asn Pro Glu
        290                 295                 300

<210> SEQ ID NO 48
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Ala Thr Ser Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
            20                  25                  30

Ala Leu Lys Ser Val Arg Val Pro Asn Gly Glu Gly Leu Pro Ile
        35                  40                  45

Ser Thr Val Arg Glu Val Ala Leu Leu Arg Arg Leu Glu Ala Phe Glu
    50                  55                  60

His Pro Asn Val Val Arg Leu Met Asp Val Cys Ala Thr Ser Arg Thr
65                  70                  75                  80

Asp Arg Glu Ile Lys Val Thr Leu Val Phe Glu His Val Asp Gln Asp
                85                  90                  95

Leu Arg Thr Tyr Leu Asp Lys Ala Pro Pro Gly Leu Pro Ala Glu
            100                 105                 110

Thr Ile Lys Asp Leu Met Arg Gln Phe Leu Arg Gly Leu Asp Phe Leu
            115                 120                 125
```

His Ala Asn Cys Ile Val His Arg Asp Leu Lys Pro Glu Asn Ile Leu
            130                 135                 140

Val Thr Ser Gly Gly Thr Val Lys Leu Ala Asp Phe Gly Leu Ala Arg
145                 150                 155                 160

Ile Tyr Ser Tyr Gln Met Ala Leu Glu Pro Val Val Thr Leu Trp
                165                 170                 175

Tyr Arg Ala Pro Glu Val Leu Leu Gln Ser Thr Tyr Ala Thr Pro Val
                180                 185                 190

Asp Met Trp Ser Val Gly Cys Ile Phe Ala Glu Met Phe Arg Arg Lys
                195                 200                 205

Pro Leu Phe Cys Gly Asn Ser Glu Ala Asp Gln Leu Gly Lys Ile Phe
                210                 215                 220

Asp Leu Ile Gly Leu Pro Pro Glu Asp Asp Trp Pro Arg Asp Val Ser
225                 230                 235                 240

Leu Pro Arg Gly Ala Phe Pro Pro Arg Gly Pro Arg Pro Val Gln Ser
                245                 250                 255

Val Val Pro Glu Met Glu Glu Ser Gly Ala Gln Leu Leu Leu Glu Met
                260                 265                 270

Leu Thr Phe Asn Pro His Lys Arg Ile Ser Ala Phe Arg Ala Leu Gln
                275                 280                 285

His Ser Tyr Leu His Lys Asp Glu Gly Asn Pro Glu
                290                 295                 300

<210> SEQ ID NO 49
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Ala Thr Ser Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
                20                  25                  30

Ala Leu Lys Ser Val Arg Val Pro Asn Gly Asp Glu Gly Leu Pro Ile
                35                  40                  45

Ser Thr Val Arg Glu Val Ala Leu Leu Arg Arg Leu Glu Ala Phe Glu
                50                  55                  60

His Pro Asn Val Val Arg Leu Met Asp Val Cys Ala Thr Ser Arg Thr
65                  70                  75                  80

Asp Arg Glu Ile Lys Val Thr Leu Val Phe Glu His Val Asp Gln Asp
                85                  90                  95

Leu Arg Thr Tyr Leu Asp Lys Ala Pro Pro Pro Gly Leu Pro Ala Glu
                100                 105                 110

Thr Ile Lys Asp Leu Met Arg Gln Phe Leu Arg Gly Leu Asp Phe Leu
                115                 120                 125

His Ala Asn Cys Ile Val His Arg Asp Leu Lys Pro Glu Asn Ile Leu
                130                 135                 140

Val Thr Ser Gly Gly Thr Val Lys Leu Ala Asp Phe Gly Leu Ala Arg
145                 150                 155                 160

Ile Tyr Ser Tyr Gln Met Ala Leu Glu Pro Val Val Thr Leu Trp
                165                 170                 175

Tyr Arg Ala Pro Glu Val Leu Leu Gln Ser Thr Tyr Ala Thr Pro Val

```
            180                 185                 190
Asp Met Trp Ser Val Gly Cys Ile Phe Ala Glu Met Phe Arg Arg Lys
        195                 200                 205

Pro Leu Phe Cys Gly Asn Ser Glu Ala Asp Gln Leu Gly Lys Ile Phe
        210                 215                 220

Asp Leu Ile Gly Leu Pro Pro Glu Asp Asp Trp Pro Arg Asp Val Ser
225                 230                 235                 240

Leu Pro Arg Gly Ala Phe Pro Pro Arg Gly Pro Arg Pro Val Gln Ser
                245                 250                 255

Val Val Pro Glu Met Glu Glu Ser Gly Ala Gln Leu Leu Leu Glu Met
                260                 265                 270

Leu Thr Phe Asn Pro His Lys Arg Ile Ser Ala Phe Arg Ala Leu Gln
        275                 280                 285

His Ser Tyr Leu His Lys Asp Glu Gly Asn Pro Glu
        290                 295                 300

<210> SEQ ID NO 50
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Ala Thr Ser Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
                20                  25                  30

Ala Leu Lys Ser Val Arg Val Pro Asn Gly Gly Asp Gly Leu Pro Ile
        35                  40                  45

Ser Thr Val Arg Glu Val Ala Leu Leu Arg Arg Leu Glu Ala Phe Glu
    50                  55                  60

His Pro Asn Val Val Arg Leu Met Asp Val Cys Ala Thr Ser Arg Thr
65                  70                  75                  80

Asp Arg Glu Ile Lys Val Thr Leu Val Phe Glu His Val Asp Gln Asp
                85                  90                  95

Leu Arg Thr Tyr Leu Asp Lys Ala Pro Pro Pro Gly Leu Pro Ala Glu
            100                 105                 110

Thr Ile Lys Asp Leu Met Arg Gln Phe Leu Arg Gly Leu Asp Phe Leu
        115                 120                 125

His Ala Asn Cys Ile Val His Arg Asp Leu Lys Pro Glu Asn Ile Leu
    130                 135                 140

Val Thr Ser Gly Gly Thr Val Lys Leu Ala Asp Phe Gly Leu Ala Arg
145                 150                 155                 160

Ile Tyr Ser Tyr Gln Met Ala Leu Glu Pro Val Val Val Thr Leu Trp
                165                 170                 175

Tyr Arg Ala Pro Glu Val Leu Leu Gln Ser Thr Tyr Ala Thr Pro Val
            180                 185                 190

Asp Met Trp Ser Val Gly Cys Ile Phe Ala Glu Met Phe Arg Arg Lys
        195                 200                 205

Pro Leu Phe Cys Gly Asn Ser Glu Ala Asp Gln Leu Gly Lys Ile Phe
        210                 215                 220

Asp Leu Ile Gly Leu Pro Pro Glu Asp Asp Trp Pro Arg Asp Val Ser
225                 230                 235                 240
```

```
Leu Pro Arg Gly Ala Phe Pro Pro Arg Gly Pro Arg Pro Val Gln Ser
                245                 250                 255

Val Val Pro Glu Met Glu Glu Ser Gly Ala Gln Leu Leu Leu Glu Met
            260                 265                 270

Leu Thr Phe Asn Pro His Lys Arg Ile Ser Ala Phe Arg Ala Leu Gln
        275                 280                 285

His Ser Tyr Leu His Lys Asp Glu Gly Asn Pro Glu
290                 295                 300

<210> SEQ ID NO 51
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Ala Thr Ser Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
            20                  25                  30

Ala Leu Lys Ser Val Arg Val Pro Asn Gly Asp Asp Gly Leu Pro Ile
        35                  40                  45

Ser Thr Val Arg Glu Val Ala Leu Leu Arg Arg Leu Glu Ala Phe Glu
    50                  55                  60

His Pro Asn Val Val Arg Leu Met Asp Val Cys Ala Thr Ser Arg Thr
65                  70                  75                  80

Asp Arg Glu Ile Lys Val Thr Leu Val Phe Glu His Val Asp Gln Asp
                85                  90                  95

Leu Arg Thr Tyr Leu Asp Lys Ala Pro Pro Gly Leu Pro Ala Glu
            100                 105                 110

Thr Ile Lys Asp Leu Met Arg Gln Phe Leu Arg Gly Leu Asp Phe Leu
        115                 120                 125

His Ala Asn Cys Ile Val His Arg Asp Leu Lys Pro Glu Asn Ile Leu
    130                 135                 140

Val Thr Ser Gly Gly Thr Val Lys Leu Ala Asp Phe Gly Leu Ala Arg
145                 150                 155                 160

Ile Tyr Ser Tyr Gln Met Ala Leu Glu Pro Val Val Thr Leu Trp
                165                 170                 175

Tyr Arg Ala Pro Glu Val Leu Leu Gln Ser Thr Tyr Ala Thr Pro Val
            180                 185                 190

Asp Met Trp Ser Val Gly Cys Ile Phe Ala Glu Met Phe Arg Arg Lys
        195                 200                 205

Pro Leu Phe Cys Gly Asn Ser Glu Ala Asp Gln Leu Gly Lys Ile Phe
    210                 215                 220

Asp Leu Ile Gly Leu Pro Pro Glu Asp Asp Trp Pro Arg Asp Val Ser
225                 230                 235                 240

Leu Pro Arg Gly Ala Phe Pro Pro Arg Gly Pro Arg Pro Val Gln Ser
                245                 250                 255

Val Val Pro Glu Met Glu Glu Ser Gly Ala Gln Leu Leu Leu Glu Met
            260                 265                 270

Leu Thr Phe Asn Pro His Lys Arg Ile Ser Ala Phe Arg Ala Leu Gln
        275                 280                 285

His Ser Tyr Leu His Lys Asp Glu Gly Asn Pro Glu
    290                 295                 300
```

<210> SEQ ID NO 52
<211> LENGTH: 326
<212> TYPE: PRT
<213> ORGANISM: Unknown
<220> FEATURE:
<223> OTHER INFORMATION: Description of Unknown:
      Cdk6 sequence

<400> SEQUENCE: 52

Met Glu Lys Asp Gly Leu Cys Arg Ala Asp Gln Gln Tyr Glu Cys Val
1               5                   10                  15

Ala Glu Ile Gly Glu Gly Ala Tyr Gly Lys Val Phe Lys Ala Arg Asp
            20                  25                  30

Leu Lys Asn Gly Gly Arg Phe Val Ala Leu Lys Arg Val Arg Val Gln
        35                  40                  45

Thr Gly Glu Glu Gly Met Pro Leu Ser Thr Ile Arg Glu Val Ala Val
    50                  55                  60

Leu Arg His Leu Glu Thr Phe Glu His Pro Asn Val Val Arg Leu Phe
65                  70                  75                  80

Asp Val Cys Thr Val Ser Arg Thr Asp Arg Glu Thr Lys Leu Thr Leu
                85                  90                  95

Val Phe Glu His Val Asp Gln Asp Leu Thr Thr Tyr Leu Asp Lys Val
            100                 105                 110

Pro Glu Pro Gly Val Pro Thr Glu Thr Ile Lys Asp Met Met Phe Gln
        115                 120                 125

Leu Leu Arg Gly Leu Asp Phe Leu His Ser His Arg Val Val His Arg
130                 135                 140

Asp Leu Lys Pro Gln Asn Ile Leu Val Thr Ser Ser Gly Gln Ile Lys
145                 150                 155                 160

Leu Ala Asp Phe Gly Leu Ala Arg Ile Tyr Ser Phe Gln Met Ala Leu
                165                 170                 175

Thr Ser Val Val Val Thr Leu Trp Tyr Arg Ala Pro Glu Val Leu Leu
            180                 185                 190

Gln Ser Ser Tyr Ala Thr Pro Val Asp Leu Trp Ser Val Gly Cys Ile
        195                 200                 205

Phe Ala Glu Met Phe Arg Arg Lys Pro Leu Phe Arg Gly Ser Ser Asp
210                 215                 220

Val Asp Gln Leu Gly Lys Ile Leu Asp Val Ile Gly Leu Pro Gly Glu
225                 230                 235                 240

Glu Asp Trp Pro Arg Asp Val Ala Leu Pro Arg Gln Ala Phe His Ser
                245                 250                 255

Lys Ser Ala Gln Pro Ile Glu Lys Phe Val Thr Asp Ile Asp Glu Leu
            260                 265                 270

Gly Lys Asp Leu Leu Leu Lys Cys Leu Thr Phe Asn Pro Ala Lys Arg
        275                 280                 285

Ile Ser Ala Tyr Ser Ala Leu Ser His Pro Tyr Phe Gln Asp Leu Glu
290                 295                 300

Arg Cys Lys Glu Asn Leu Asp Ser His Leu Pro Pro Ser Gln Asn Thr
305                 310                 315                 320

Ser Glu Leu Asn Thr Ala
                325

<210> SEQ ID NO 53
<211> LENGTH: 326
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 53

Met Glu Lys Asp Gly Leu Cys Arg Ala Asp Gln Gln Tyr Glu Cys Val
1               5                   10                  15
Ala Glu Ile Gly Glu Gly Ala Tyr Gly Lys Val Phe Lys Ala Arg Asp
            20                  25                  30
Leu Lys Asn Gly Gly Arg Phe Val Ala Leu Lys Arg Val Arg Val Gln
        35                  40                  45
Thr Gly Glu Glu Gly Met Pro Leu Ser Thr Ile Arg Glu Val Ala Val
    50                  55                  60
Leu Arg His Leu Glu Thr Phe Glu His Pro Asn Val Val Arg Leu Phe
65                  70                  75                  80
Asp Val Cys Thr Val Ser Arg Thr Asp Arg Glu Thr Lys Leu Thr Leu
                85                  90                  95
Val Phe Glu His Val Asp Gln Asp Leu Thr Thr Tyr Leu Asp Lys Val
            100                 105                 110
Pro Glu Pro Gly Val Pro Thr Glu Thr Ile Lys Asp Met Met Phe Gln
        115                 120                 125
Leu Leu Arg Gly Leu Asp Phe Leu His Ser His Arg Val Val His Arg
    130                 135                 140
Asp Leu Lys Pro Gln Asn Ile Leu Val Thr Ser Ser Gly Gln Ile Lys
145                 150                 155                 160
Leu Ala Asp Phe Gly Leu Ala Arg Ile Tyr Ser Phe Gln Met Ala Leu
                165                 170                 175
Asp Ser Val Val Val Thr Leu Trp Tyr Arg Ala Pro Glu Val Leu Leu
            180                 185                 190
Gln Ser Ser Tyr Ala Thr Pro Val Asp Leu Trp Ser Val Gly Cys Ile
        195                 200                 205
Phe Ala Glu Met Phe Arg Arg Lys Pro Leu Phe Arg Gly Ser Ser Asp
    210                 215                 220
Val Asp Gln Leu Gly Lys Ile Leu Asp Val Ile Gly Leu Pro Gly Glu
225                 230                 235                 240
Glu Asp Trp Pro Arg Asp Val Ala Leu Pro Arg Gln Ala Phe His Ser
                245                 250                 255
Lys Ser Ala Gln Pro Ile Glu Lys Phe Val Thr Asp Ile Asp Glu Leu
            260                 265                 270
Gly Lys Asp Leu Leu Leu Lys Cys Leu Thr Phe Asn Pro Ala Lys Arg
        275                 280                 285
Ile Ser Ala Tyr Ser Ala Leu Ser His Pro Tyr Phe Gln Asp Leu Glu
    290                 295                 300
Arg Cys Lys Glu Asn Leu Asp Ser His Leu Pro Pro Ser Gln Asn Thr
305                 310                 315                 320
Ser Glu Leu Asn Thr Ala
                325

<210> SEQ ID NO 54
<211> LENGTH: 326
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

```
Met Glu Lys Asp Gly Leu Cys Arg Ala Asp Gln Gln Tyr Glu Cys Val
1               5                   10                  15

Ala Glu Ile Gly Glu Gly Ala Tyr Gly Lys Val Phe Lys Ala Arg Asp
            20                  25                  30

Leu Lys Asn Gly Gly Arg Phe Val Ala Leu Lys Arg Val Arg Val Gln
        35                  40                  45

Thr Gly Glu Glu Gly Met Pro Leu Ser Thr Ile Arg Glu Val Ala Val
    50                  55                  60

Leu Arg His Leu Glu Thr Phe Glu His Pro Asn Val Val Arg Leu Phe
65                  70                  75                  80

Asp Val Cys Thr Val Ser Arg Thr Asp Arg Glu Thr Lys Leu Thr Leu
                85                  90                  95

Val Phe Glu His Val Asp Gln Asp Leu Thr Thr Tyr Leu Asp Lys Val
            100                 105                 110

Pro Glu Pro Gly Val Pro Thr Glu Thr Ile Lys Asp Met Met Phe Gln
        115                 120                 125

Leu Leu Arg Gly Leu Asp Phe Leu His Ser His Arg Val Val His Arg
    130                 135                 140

Asp Leu Lys Pro Gln Asn Ile Leu Val Thr Ser Ser Gly Gln Ile Lys
145                 150                 155                 160

Leu Ala Asp Phe Gly Leu Ala Arg Ile Tyr Ser Phe Gln Met Ala Leu
                165                 170                 175

Glu Ser Val Val Val Thr Leu Trp Tyr Arg Ala Pro Glu Val Leu Leu
            180                 185                 190

Gln Ser Ser Tyr Ala Thr Pro Val Asp Leu Trp Ser Val Gly Cys Ile
        195                 200                 205

Phe Ala Glu Met Phe Arg Arg Lys Pro Leu Phe Arg Gly Ser Ser Asp
    210                 215                 220

Val Asp Gln Leu Gly Lys Ile Leu Asp Val Ile Gly Leu Pro Gly Glu
225                 230                 235                 240

Glu Asp Trp Pro Arg Asp Val Ala Leu Pro Arg Gln Ala Phe His Ser
                245                 250                 255

Lys Ser Ala Gln Pro Ile Glu Lys Phe Val Thr Asp Ile Asp Glu Leu
            260                 265                 270

Gly Lys Asp Leu Leu Leu Lys Cys Leu Thr Phe Asn Pro Ala Lys Arg
        275                 280                 285

Ile Ser Ala Tyr Ser Ala Leu Ser His Pro Tyr Phe Gln Asp Leu Glu
    290                 295                 300

Arg Cys Lys Glu Asn Leu Asp Ser His Leu Pro Pro Ser Gln Asn Thr
305                 310                 315                 320

Ser Glu Leu Asn Thr Ala
                325
```

<210> SEQ ID NO 55
<211> LENGTH: 295
<212> TYPE: PRT
<213> ORGANISM: Unknown
<220> FEATURE:
<223> OTHER INFORMATION: Description of Unknown:
    CycD1 sequence

<400> SEQUENCE: 55

```
Met Glu His Gln Leu Leu Cys Cys Glu Val Glu Thr Ile Arg Arg Ala
1               5                   10                  15
```

```
Tyr Pro Asp Ala Asn Leu Leu Asn Asp Arg Val Leu Arg Ala Met Leu
             20                  25                  30
Lys Ala Glu Glu Thr Cys Ala Pro Ser Val Ser Tyr Phe Lys Cys Val
         35                  40                  45
Gln Lys Glu Val Leu Pro Ser Met Arg Lys Ile Val Ala Thr Trp Met
 50                  55                  60
Leu Glu Val Cys Glu Glu Gln Lys Cys Glu Glu Val Phe Pro Leu
 65                  70                  75                  80
Ala Met Asn Tyr Leu Asp Arg Phe Leu Ser Leu Glu Pro Val Lys Lys
                 85                  90                  95
Ser Arg Leu Gln Leu Leu Gly Ala Thr Cys Met Phe Val Ala Ser Lys
            100                 105                 110
Met Lys Glu Thr Ile Pro Leu Thr Ala Glu Lys Leu Cys Ile Tyr Thr
        115                 120                 125
Asp Asn Ser Ile Arg Pro Glu Glu Leu Leu Gln Met Glu Leu Leu Leu
    130                 135                 140
Val Asn Lys Leu Lys Trp Asn Leu Ala Ala Met Thr Pro His Asp Phe
145                 150                 155                 160
Ile Glu His Phe Leu Ser Lys Met Pro Glu Ala Glu Glu Asn Lys Gln
                165                 170                 175
Ile Ile Arg Lys His Ala Gln Thr Phe Val Ala Leu Cys Ala Thr Asp
            180                 185                 190
Val Lys Phe Ile Ser Asn Pro Pro Ser Met Val Ala Ala Gly Ser Val
        195                 200                 205
Val Ala Ala Val Gln Gly Leu Asn Leu Arg Ser Pro Asn Asn Phe Leu
    210                 215                 220
Ser Tyr Tyr Arg Leu Thr Arg Phe Leu Ser Arg Val Ile Lys Cys Asp
225                 230                 235                 240
Pro Asp Cys Leu Arg Ala Cys Gln Glu Gln Ile Glu Ala Leu Leu Glu
                245                 250                 255
Ser Ser Leu Arg Gln Ala Gln Gln Asn Met Asp Pro Lys Ala Ala Glu
            260                 265                 270
Glu Glu Glu Glu Glu Glu Glu Val Asp Leu Ala Cys Thr Pro Thr
        275                 280                 285
Asp Val Arg Asp Val Asp Ile
    290                 295

<210> SEQ ID NO 56
<211> LENGTH: 249
<212> TYPE: PRT
<213> ORGANISM: Unknown
<220> FEATURE:
<223> OTHER INFORMATION: Description of Unknown:
      CycD1 sequence

<400> SEQUENCE: 56

Asp Ala Asn Leu Leu Asn Asp Arg Val Leu Arg Ala Met Leu Lys Ala
1               5                  10                  15
Glu Glu Thr Cys Ala Pro Ser Val Ser Tyr Phe Lys Cys Val Gln Lys
            20                  25                  30
Glu Val Leu Pro Ser Met Arg Lys Ile Val Ala Thr Trp Met Leu Glu
        35                  40                  45
Val Cys Glu Glu Gln Lys Cys Glu Glu Val Phe Pro Leu Ala Met
    50                  55                  60
Asn Tyr Leu Asp Arg Phe Leu Ser Leu Glu Pro Val Lys Lys Ser Arg
65                  70                  75                  80
```

```
Leu Gln Leu Leu Gly Ala Thr Cys Met Phe Val Ala Ser Lys Met Lys
                85                  90                  95

Glu Thr Ile Pro Leu Thr Ala Glu Lys Leu Cys Ile Tyr Thr Asp Asn
            100                 105                 110

Ser Ile Arg Pro Glu Glu Leu Leu Gln Met Glu Leu Leu Val Asn
        115                 120                 125

Lys Leu Lys Trp Asn Leu Ala Ala Met Thr Pro His Asp Phe Ile Glu
130                 135                 140

His Phe Leu Ser Lys Met Pro Glu Ala Glu Glu Asn Lys Gln Ile Ile
145                 150                 155                 160

Arg Lys His Ala Gln Thr Phe Val Ala Leu Cys Ala Thr Asp Val Lys
                165                 170                 175

Phe Ile Ser Asn Pro Pro Ser Met Val Ala Ala Gly Ser Val Val Ala
            180                 185                 190

Ala Val Gln Gly Leu Asn Leu Arg Ser Pro Asn Asn Phe Leu Ser Tyr
        195                 200                 205

Tyr Arg Leu Thr Arg Phe Leu Ser Arg Val Ile Lys Cys Asp Pro Asp
210                 215                 220

Cys Leu Arg Ala Cys Gln Glu Gln Ile Glu Ala Leu Leu Glu Ser Ser
225                 230                 235                 240

Leu Arg Gln Ala Gln Gln Asn Met Asp
                245

<210> SEQ ID NO 57
<211> LENGTH: 289
<212> TYPE: PRT
<213> ORGANISM: Unknown
<220> FEATURE:
<223> OTHER INFORMATION: Description of Unknown:
      CycD2 sequence

<400> SEQUENCE: 57

Met Glu Leu Leu Cys His Glu Val Asp Pro Val Arg Arg Ala Val Arg
1               5                   10                  15

Asp Arg Asn Leu Leu Arg Asp Asp Arg Val Leu Gln Asn Leu Leu Thr
            20                  25                  30

Ile Glu Glu Arg Tyr Leu Pro Gln Cys Ser Tyr Phe Lys Cys Val Gln
        35                  40                  45

Lys Asp Ile Gln Pro Tyr Met Arg Arg Met Val Ala Thr Trp Met Leu
    50                  55                  60

Glu Val Cys Glu Glu Gln Lys Cys Glu Glu Val Phe Pro Leu Ala
65                  70                  75                  80

Met Asn Tyr Leu Asp Arg Phe Leu Ala Gly Val Pro Thr Pro Lys Ser
                85                  90                  95

His Leu Gln Leu Leu Gly Ala Val Cys Met Phe Leu Ala Ser Lys Leu
            100                 105                 110

Lys Glu Thr Ser Pro Leu Thr Ala Glu Lys Leu Cys Ile Tyr Thr Asp
        115                 120                 125

Asn Ser Ile Lys Pro Gln Glu Leu Leu Glu Trp Glu Leu Val Val Leu
    130                 135                 140

Gly Lys Leu Lys Trp Asn Leu Ala Ala Val Thr Pro His Asp Phe Ile
145                 150                 155                 160

Glu His Ile Leu Arg Lys Leu Pro Gln Gln Arg Glu Lys Leu Ser Leu
                165                 170                 175

Ile Arg Lys His Ala Gln Thr Phe Ile Ala Leu Cys Ala Thr Asp Phe
```

```
            180                 185                 190
Lys Phe Ala Met Tyr Pro Pro Ser Met Ile Ala Thr Gly Ser Val Gly
            195                 200                 205

Ala Ala Ile Cys Gly Leu Gln Gln Asp Glu Glu Val Ser Ser Leu Thr
            210                 215                 220

Cys Asp Ala Leu Thr Glu Leu Leu Ala Lys Ile Thr Asn Thr Asp Val
225                 230                 235                 240

Asp Cys Leu Lys Ala Cys Gln Glu Gln Ile Glu Ala Val Leu Leu Asn
                245                 250                 255

Ser Leu Gln Gln Tyr Arg Gln Asp Gln Arg Asp Gly Ser Lys Ser Glu
            260                 265                 270

Asp Glu Leu Asp Gln Ala Ser Thr Pro Thr Asp Val Arg Asp Ile Asp
            275                 280                 285

Leu

<210> SEQ ID NO 58
<211> LENGTH: 292
<212> TYPE: PRT
<213> ORGANISM: Unknown
<220> FEATURE:
<223> OTHER INFORMATION: Description of Unknown:
      CycD3 sequence

<400> SEQUENCE: 58

Met Glu Leu Leu Cys Cys Glu Gly Thr Arg His Ala Pro Arg Ala Gly
1               5                   10                  15

Pro Asp Pro Arg Leu Leu Gly Asp Gln Arg Val Leu Gln Ser Leu Leu
            20                  25                  30

Arg Leu Glu Glu Arg Tyr Val Pro Arg Ala Ser Tyr Phe Gln Cys Val
        35                  40                  45

Gln Arg Glu Ile Lys Pro His Met Arg Lys Met Leu Ala Tyr Trp Met
    50                  55                  60

Leu Glu Val Cys Glu Glu Gln Arg Cys Glu Glu Val Phe Pro Leu
65                  70                  75                  80

Ala Met Asn Tyr Leu Asp Arg Tyr Leu Ser Cys Val Pro Thr Arg Lys
                85                  90                  95

Ala Gln Leu Gln Leu Leu Gly Ala Val Cys Met Leu Leu Ala Ser Lys
            100                 105                 110

Leu Arg Glu Thr Thr Pro Leu Thr Ile Glu Lys Leu Cys Ile Tyr Thr
            115                 120                 125

Asp His Ala Val Ser Pro Arg Gln Leu Arg Asp Trp Glu Val Leu Val
130                 135                 140

Leu Gly Lys Leu Lys Trp Asp Leu Ala Ala Val Ile Ala His Asp Phe
145                 150                 155                 160

Leu Ala Phe Ile Leu His Arg Leu Ser Leu Pro Arg Asp Arg Gln Ala
                165                 170                 175

Leu Val Lys Lys His Ala Gln Thr Phe Leu Ala Leu Cys Ala Thr Asp
            180                 185                 190

Tyr Thr Phe Ala Met Tyr Pro Pro Ser Met Ile Ala Thr Gly Ser Ile
            195                 200                 205

Gly Ala Ala Val Gln Gly Leu Gly Ala Cys Ser Met Ser Gly Asp Glu
            210                 215                 220

Leu Thr Glu Leu Leu Ala Gly Ile Thr Gly Thr Glu Val Asp Cys Leu
225                 230                 235                 240

Arg Ala Cys Gln Glu Gln Ile Glu Ala Ala Leu Arg Glu Ser Leu Arg
```

```
                     245                 250                 255

Glu Ala Ser Gln Thr Ser Ser Pro Ala Pro Lys Ala Pro Arg Gly
            260                 265                 270

Ser Ser Ser Gln Gly Pro Ser Gln Thr Ser Thr Pro Thr Asp Val Thr
        275                 280                 285

Ala Ile His Leu
    290

<210> SEQ ID NO 59
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (50)..(50)
<223> OTHER INFORMATION: Tyr, Glu, Asp or Arg
<220> FEATURE:
<221> NAME/KEY: MOD_RES
<222> LOCATION: (64)..(64)
<223> OTHER INFORMATION: Tyr, Glu or Asp
<220> FEATURE:
<221> NAME/KEY: MOD_RES
<222> LOCATION: (65)..(65)
<223> OTHER INFORMATION: Tyr, Glu or Asp
<220> FEATURE:
<223> OTHER INFORMATION: See specification as filed for detailed
      description of substitutions and preferred embodiments

<400> SEQUENCE: 59

Lys Pro Ser Ala Cys Arg Asn Leu Phe Gly Pro Val Asp His Glu Glu
1               5                   10                  15

Leu Thr Arg Asp Leu Glu Lys His Cys Arg Asp Met Glu Glu Ala Ser
            20                  25                  30

Gln Arg Lys Trp Asn Phe Asp Phe Gln Asn His Lys Pro Leu Glu Gly
        35                  40                  45

Lys Xaa Glu Trp Gln Glu Val Glu Lys Gly Ser Leu Pro Glu Phe Xaa
    50                  55                  60

Xaa Arg Pro Pro Arg Pro Pro Lys Gly Ala
65                  70

<210> SEQ ID NO 60
<211> LENGTH: 4
<212> TYPE: PRT
<213> ORGANISM: Unknown
<220> FEATURE:
<223> OTHER INFORMATION: Description of Unknown:
      Phosphorylation site
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Lys or Arg

<400> SEQUENCE: 60

Xaa Pro Xaa Xaa
1
```

```
<210> SEQ ID NO 61
<211> LENGTH: 928
<212> TYPE: PRT
<213> ORGANISM: Unknown
<220> FEATURE:
<223> OTHER INFORMATION: Description of Unknown:
      Rb sequence

<400> SEQUENCE: 61

Met Pro Pro Lys Thr Pro Arg Lys Thr Ala Thr Ala Ala Ala Ala
1               5                   10                  15

Ala Ala Glu Pro Pro Ala Pro Pro Pro Pro Pro Pro Glu Glu Asp
                20                  25                  30

Pro Glu Gln Asp Ser Gly Pro Glu Asp Leu Pro Leu Val Arg Leu Glu
            35                  40                  45

Phe Glu Glu Thr Glu Glu Pro Asp Phe Thr Ala Leu Cys Gln Lys Leu
    50                  55                  60

Lys Ile Pro Asp His Val Arg Glu Arg Ala Trp Leu Thr Trp Glu Lys
65                  70                  75                  80

Val Ser Ser Val Asp Gly Val Leu Gly Gly Tyr Ile Gln Lys Lys Lys
                85                  90                  95

Glu Leu Trp Gly Ile Cys Ile Phe Ile Ala Ala Val Asp Leu Asp Glu
                100                 105                 110

Met Ser Phe Thr Phe Thr Glu Leu Gln Lys Asn Ile Glu Ile Ser Val
            115                 120                 125

His Lys Phe Phe Asn Leu Leu Lys Glu Ile Asp Thr Ser Thr Lys Val
            130                 135                 140

Asp Asn Ala Met Ser Arg Leu Leu Lys Lys Tyr Asp Val Leu Phe Ala
145                 150                 155                 160

Leu Phe Ser Lys Leu Glu Arg Thr Cys Glu Leu Ile Tyr Leu Thr Gln
                165                 170                 175

Pro Ser Ser Ser Ile Ser Thr Glu Ile Asn Ser Ala Leu Val Leu Lys
            180                 185                 190

Val Ser Trp Ile Thr Phe Leu Leu Ala Lys Gly Glu Val Leu Gln Met
            195                 200                 205

Glu Asp Asp Leu Val Ile Ser Phe Gln Leu Met Leu Cys Val Leu Asp
        210                 215                 220

Tyr Phe Ile Lys Leu Ser Pro Pro Met Leu Leu Lys Glu Pro Tyr Lys
225                 230                 235                 240

Thr Ala Val Ile Pro Ile Asn Gly Ser Pro Arg Thr Pro Arg Arg Gly
                245                 250                 255

Gln Asn Arg Ser Ala Arg Ile Ala Lys Gln Leu Glu Asn Asp Thr Arg
            260                 265                 270

Ile Ile Glu Val Leu Cys Lys Glu His Glu Cys Asn Ile Asp Glu Val
        275                 280                 285

Lys Asn Val Tyr Phe Lys Asn Phe Ile Pro Phe Met Asn Ser Leu Gly
        290                 295                 300

Leu Val Thr Ser Asn Gly Leu Pro Glu Val Glu Asn Leu Ser Lys Arg
305                 310                 315                 320

Tyr Glu Glu Ile Tyr Leu Lys Asn Lys Asp Leu Asp Ala Arg Leu Phe
                325                 330                 335

Leu Asp His Asp Lys Thr Leu Gln Thr Asp Ser Ile Asp Ser Phe Glu
            340                 345                 350

Thr Gln Arg Thr Pro Arg Lys Ser Asn Leu Asp Glu Glu Val Asn Val
        355                 360                 365
```

-continued

```
Ile Pro Pro His Thr Pro Val Arg Thr Val Met Asn Thr Ile Gln Gln
370                 375                 380

Leu Met Met Ile Leu Asn Ser Ala Ser Asp Gln Pro Ser Glu Asn Leu
385                 390                 395                 400

Ile Ser Tyr Phe Asn Asn Cys Thr Val Asn Pro Lys Glu Ser Ile Leu
                405                 410                 415

Lys Arg Val Lys Asp Ile Gly Tyr Ile Phe Lys Glu Lys Phe Ala Lys
                420                 425                 430

Ala Val Gly Gln Gly Cys Val Glu Ile Gly Ser Gln Arg Tyr Lys Leu
            435                 440                 445

Gly Val Arg Leu Tyr Tyr Arg Val Met Glu Ser Met Leu Lys Ser Glu
450                 455                 460

Glu Glu Arg Leu Ser Ile Gln Asn Phe Ser Lys Leu Leu Asn Asp Asn
465                 470                 475                 480

Ile Phe His Met Ser Leu Leu Ala Cys Ala Leu Glu Val Val Met Ala
                485                 490                 495

Thr Tyr Ser Arg Ser Thr Ser Gln Asn Leu Asp Ser Gly Thr Asp Leu
            500                 505                 510

Ser Phe Pro Trp Ile Leu Asn Val Leu Asn Leu Lys Ala Phe Asp Phe
            515                 520                 525

Tyr Lys Val Ile Glu Ser Phe Ile Lys Ala Glu Gly Asn Leu Thr Arg
530                 535                 540

Glu Met Ile Lys His Leu Glu Arg Cys Glu His Arg Ile Met Glu Ser
545                 550                 555                 560

Leu Ala Trp Leu Ser Asp Ser Pro Leu Phe Asp Leu Ile Lys Gln Ser
                565                 570                 575

Lys Asp Arg Glu Gly Pro Thr Asp His Leu Glu Ser Ala Cys Pro Leu
            580                 585                 590

Asn Leu Pro Leu Gln Asn Asn His Thr Ala Ala Asp Met Tyr Leu Ser
            595                 600                 605

Pro Val Arg Ser Pro Lys Lys Lys Gly Ser Thr Thr Arg Val Asn Ser
            610                 615                 620

Thr Ala Asn Ala Glu Thr Gln Ala Thr Ser Ala Phe Gln Thr Gln Lys
625                 630                 635                 640

Pro Leu Lys Ser Thr Ser Leu Ser Leu Phe Tyr Lys Lys Val Tyr Arg
                645                 650                 655

Leu Ala Tyr Leu Arg Leu Asn Thr Leu Cys Glu Arg Leu Leu Ser Glu
            660                 665                 670

His Pro Glu Leu Glu His Ile Ile Trp Thr Leu Phe Gln His Thr Leu
            675                 680                 685

Gln Asn Glu Tyr Glu Leu Met Arg Asp Arg His Leu Asp Gln Ile Met
690                 695                 700

Met Cys Ser Met Tyr Gly Ile Cys Lys Val Lys Asn Ile Asp Leu Lys
705                 710                 715                 720

Phe Lys Ile Ile Val Thr Ala Tyr Lys Asp Leu Pro His Ala Val Gln
                725                 730                 735

Glu Thr Phe Lys Arg Val Leu Ile Lys Glu Glu Tyr Asp Ser Ile
                740                 745                 750

Ile Val Phe Tyr Asn Ser Val Phe Met Gln Arg Leu Lys Thr Asn Ile
                755                 760                 765

Leu Gln Tyr Ala Ser Thr Arg Pro Pro Thr Leu Ser Pro Ile Pro His
770                 775                 780

Ile Pro Arg Ser Pro Tyr Lys Phe Pro Ser Ser Pro Leu Arg Ile Pro
```

```
                785                 790                 795                 800
Gly Gly Asn Ile Tyr Ile Ser Pro Leu Lys Ser Pro Tyr Lys Ile Ser
                805                 810                 815
Glu Gly Leu Pro Thr Pro Thr Lys Met Thr Pro Arg Ser Arg Ile Leu
                820                 825                 830
Val Ser Ile Gly Glu Ser Phe Gly Thr Ser Glu Lys Phe Gln Lys Ile
                835                 840                 845
Asn Gln Met Val Cys Asn Ser Asp Arg Val Leu Lys Arg Ser Ala Glu
                850                 855                 860
Gly Ser Asn Pro Pro Lys Pro Leu Lys Leu Arg Phe Asp Ile Glu
            865                 870                 875                 880
Gly Ser Asp Glu Ala Asp Gly Ser Lys His Leu Pro Gly Glu Ser Lys
                885                 890                 895
Phe Gln Gln Lys Leu Ala Glu Met Thr Ser Thr Arg Thr Arg Met Gln
                900                 905                 910
Lys Gln Lys Met Asn Asp Ser Met Asp Thr Ser Asn Lys Glu Glu Lys
                915                 920                 925

<210> SEQ ID NO 62
<211> LENGTH: 158
<212> TYPE: PRT
<213> ORGANISM: Unknown
<220> FEATURE:
<223> OTHER INFORMATION: Description of Unknown:
      Rb sequence

<400> SEQUENCE: 62

Tyr Ala Ser Thr Arg Pro Pro Thr Leu Ser Pro Ile Pro His Ile Pro
1               5                   10                  15
Arg Ser Pro Tyr Lys Phe Pro Ser Ser Pro Leu Arg Ile Pro Gly Gly
                20                  25                  30
Asn Ile Tyr Ile Ser Pro Leu Lys Ser Pro Tyr Lys Ile Ser Glu Gly
                35                  40                  45
Leu Pro Thr Pro Thr Lys Met Thr Pro Arg Ser Arg Ile Leu Val Ser
    50                  55                  60
Ile Gly Glu Ser Phe Gly Thr Ser Glu Lys Phe Gln Lys Ile Asn Gln
65                  70                  75                  80
Met Val Cys Asn Ser Asp Arg Val Leu Lys Arg Ser Ala Glu Gly Ser
                85                  90                  95
Asn Pro Pro Lys Pro Leu Lys Leu Arg Phe Asp Ile Glu Gly Ser
                100                 105                 110
Asp Glu Ala Asp Gly Ser Lys His Leu Pro Gly Glu Ser Lys Phe Gln
            115                 120                 125
Gln Lys Leu Ala Glu Met Thr Ser Thr Arg Thr Arg Met Gln Lys Gln
            130                 135                 140
Lys Met Asn Asp Ser Met Asp Thr Ser Asn Lys Glu Glu Lys
145                 150                 155

<210> SEQ ID NO 63
<211> LENGTH: 763
<212> TYPE: PRT
<213> ORGANISM: Unknown
<220> FEATURE:
<223> OTHER INFORMATION: Description of Unknown:
      FoxM1 sequence

<400> SEQUENCE: 63

Met Lys Thr Ser Pro Arg Arg Pro Leu Ile Leu Lys Arg Arg Arg Leu
```

-continued

```
1               5                   10                  15
Pro Leu Pro Val Gln Asn Ala Pro Ser Glu Thr Ser Glu Glu Glu Pro
            20                  25                  30

Lys Arg Ser Pro Ala Gln Gln Glu Ser Asn Gln Ala Glu Ala Ser Lys
            35                  40                  45

Glu Val Ala Glu Ser Asn Ser Cys Lys Phe Pro Ala Gly Ile Lys Ile
            50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                    85                  90                  95

Glu Ser Gly Ser Ser Gly Pro Asn Lys Phe Ile Leu Ile Ser Cys Gly
                100                 105                 110

Gly Ala Pro Thr Gln Pro Pro Gly Leu Arg Pro Gln Thr Gln Thr Ser
                115                 120                 125

Tyr Asp Ala Lys Arg Thr Glu Val Thr Leu Glu Thr Leu Gly Pro Lys
                130                 135                 140

Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
                180                 185                 190

Asp Gly Leu Gly Ser Arg Ser Ile Lys Gln Glu Met Glu Glu Lys Glu
                195                 200                 205

Asn Cys His Leu Glu Gln Arg Gln Val Lys Val Glu Glu Pro Ser Arg
                210                 215                 220

Pro Ser Ala Ser Trp Gln Asn Ser Val Ser Glu Arg Pro Pro Tyr Ser
225                 230                 235                 240

Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
                260                 265                 270

Phe Lys His Ile Ala Lys Pro Gly Trp Lys Asn Ser Ile Arg His Asn
                275                 280                 285

Leu Ser Leu His Asp Met Phe Val Arg Glu Thr Ser Ala Asn Gly Lys
                290                 295                 300

Val Ser Phe Trp Thr Ile His Pro Ser Ala Asn Arg Tyr Leu Thr Leu
305                 310                 315                 320

Asp Gln Val Phe Lys Pro Leu Asp Pro Gly Ser Pro Gln Leu Pro Glu
                325                 330                 335

His Leu Glu Ser Gln Gln Lys Arg Pro Asn Pro Glu Leu Arg Arg Asn
                340                 345                 350

Met Thr Ile Lys Thr Glu Leu Pro Leu Gly Ala Arg Arg Lys Met Lys
                355                 360                 365

Pro Leu Leu Pro Arg Val Ser Ser Tyr Leu Val Pro Ile Gln Phe Pro
                370                 375                 380

Val Asn Gln Ser Leu Val Leu Gln Pro Ser Val Lys Val Pro Leu Pro
385                 390                 395                 400

Leu Ala Ala Ser Leu Met Ser Ser Glu Leu Ala Arg His Ser Lys Arg
                405                 410                 415

Val Arg Ile Ala Pro Lys Val Leu Leu Ala Glu Glu Gly Ile Ala Pro
                420                 425                 430
```

```
Leu Ser Ser Ala Gly Pro Gly Lys Glu Glu Lys Leu Leu Phe Gly Glu
        435                 440                 445

Gly Phe Ser Pro Leu Leu Pro Val Gln Thr Ile Lys Glu Glu Glu Ile
450                 455                 460

Gln Pro Gly Glu Glu Met Pro His Leu Ala Arg Pro Ile Lys Val Glu
465                 470                 475                 480

Ser Pro Pro Leu Glu Glu Trp Pro Ser Pro Ala Pro Ser Phe Lys Glu
                485                 490                 495

Glu Ser Ser His Ser Trp Glu Asp Ser Ser Gln Ser Pro Thr Pro Arg
            500                 505                 510

Pro Lys Lys Ser Tyr Ser Gly Leu Arg Ser Pro Thr Arg Cys Val Ser
        515                 520                 525

Glu Met Leu Val Ile Gln His Arg Glu Arg Arg Glu Arg Ser Arg Ser
        530                 535                 540

Arg Arg Lys Gln His Leu Leu Pro Pro Cys Val Asp Glu Pro Glu Leu
545                 550                 555                 560

Leu Phe Ser Glu Gly Pro Ser Thr Ser Arg Trp Ala Ala Glu Leu Pro
                565                 570                 575

Phe Pro Ala Asp Ser Ser Asp Pro Ala Ser Gln Leu Ser Tyr Ser Gln
                580                 585                 590

Glu Val Gly Gly Pro Phe Lys Thr Pro Ile Lys Glu Thr Leu Pro Ile
            595                 600                 605

Ser Ser Thr Pro Ser Lys Ser Val Leu Pro Arg Thr Pro Glu Ser Trp
        610                 615                 620

Arg Leu Thr Pro Pro Ala Lys Val Gly Gly Leu Asp Phe Ser Pro Val
625                 630                 635                 640

Gln Thr Ser Gln Gly Ala Ser Asp Pro Leu Pro Asp Pro Leu Gly Leu
                645                 650                 655

Met Asp Leu Ser Thr Thr Pro Leu Gln Ser Ala Pro Pro Leu Glu Ser
                660                 665                 670

Pro Gln Arg Leu Leu Ser Ser Glu Pro Leu Asp Leu Ile Ser Val Pro
            675                 680                 685

Phe Gly Asn Ser Ser Pro Ser Asp Ile Asp Val Pro Lys Pro Gly Ser
        690                 695                 700

Pro Glu Pro Gln Val Ser Gly Leu Ala Ala Asn Arg Ser Leu Thr Glu
705                 710                 715                 720

Gly Leu Val Leu Asp Thr Met Asn Asp Ser Leu Ser Lys Ile Leu Leu
                725                 730                 735

Asp Ile Ser Phe Pro Gly Leu Asp Glu Asp Pro Leu Gly Pro Asp Asn
            740                 745                 750

Ile Asn Trp Ser Gln Phe Ile Pro Glu Leu Gln
        755                 760

<210> SEQ ID NO 64
<211> LENGTH: 223
<212> TYPE: PRT
<213> ORGANISM: Unknown
<220> FEATURE:
<223> OTHER INFORMATION: Description of Unknown:
      FoxM1 sequence

<400> SEQUENCE: 64

Cys Val Ser Glu Met Leu Val Ile Gln His Arg Glu Arg Arg Glu Arg
1               5                   10                  15

Ser Arg Ser Arg Arg Lys Gln His Leu Leu Pro Pro Cys Val Asp Glu
```

```
                 20                  25                  30
Pro Glu Leu Leu Phe Ser Glu Gly Pro Ser Thr Ser Arg Trp Ala Ala
            35                  40                  45

Glu Leu Pro Phe Pro Ala Asp Ser Ser Asp Pro Ala Ser Gln Leu Ser
    50                  55                  60

Tyr Ser Gln Glu Val Gly Gly Pro Phe Lys Thr Pro Ile Lys Glu Thr
65                  70                  75                  80

Leu Pro Ile Ser Ser Thr Pro Ser Lys Ser Val Leu Pro Arg Thr Pro
                85                  90                  95

Glu Ser Trp Arg Leu Thr Pro Ala Lys Val Gly Gly Leu Asp Phe
            100                 105                 110

Ser Pro Val Gln Thr Ser Gln Gly Ala Ser Asp Pro Leu Pro Asp Pro
        115                 120                 125

Leu Gly Leu Met Asp Leu Ser Thr Thr Pro Leu Gln Ser Ala Pro Pro
    130                 135                 140

Leu Glu Ser Pro Gln Arg Leu Leu Ser Ser Glu Pro Leu Asp Leu Ile
145                 150                 155                 160

Ser Val Pro Phe Gly Asn Ser Ser Pro Ser Asp Ile Asp Val Pro Lys
                165                 170                 175

Pro Gly Ser Pro Glu Pro Gln Val Ser Gly Leu Ala Ala Asn Arg Ser
            180                 185                 190

Leu Thr Glu Gly Leu Val Leu Asp Thr Met Asn Asp Ser Leu Ser Lys
        195                 200                 205

Ile Leu Leu Asp Ile Ser Phe Pro Gly Leu Asp Glu Asp Pro Leu
    210                 215                 220

<210> SEQ ID NO 65
<211> LENGTH: 215
<212> TYPE: PRT
<213> ORGANISM: Unknown
<220> FEATURE:
<223> OTHER INFORMATION: Description of Unknown:
      Histone H1 sequence

<400> SEQUENCE: 65

Met Ser Glu Thr Val Pro Pro Ala Pro Ala Ala Ser Ala Ala Pro Glu
1               5                   10                  15

Lys Pro Leu Ala Gly Lys Lys Ala Lys Lys Pro Ala Lys Ala Ala Ala
            20                  25                  30

Ala Ser Lys Lys Lys Pro Ala Gly Pro Ser Val Ser Glu Leu Ile Val
        35                  40                  45

Gln Ala Ala Ser Ser Ser Lys Glu Arg Gly Gly Val Ser Leu Ala Ala
    50                  55                  60

Leu Lys Lys Ala Leu Ala Ala Gly Tyr Asp Val Glu Lys Asn Asn
65                  70                  75                  80

Ser Arg Ile Lys Leu Gly Ile Lys Ser Leu Val Ser Lys Gly Thr Leu
                85                  90                  95

Val Gln Thr Lys Gly Thr Gly Ala Ser Gly Ser Phe Lys Leu Asn Lys
            100                 105                 110

Lys Ala Ser Ser Val Glu Thr Lys Pro Gly Ala Ser Lys Val Ala Thr
        115                 120                 125

Lys Thr Lys Ala Thr Gly Ala Ser Lys Lys Leu Lys Lys Ala Thr Gly
    130                 135                 140

Ala Ser Lys Lys Ser Val Lys Thr Pro Lys Lys Ala Lys Lys Pro Ala
145                 150                 155                 160
```

Ala Thr Arg Lys Ser Ser Lys Asn Pro Lys Lys Pro Lys Thr Val Lys
            165                 170                 175

Pro Lys Lys Val Ala Lys Ser Pro Ala Lys Ala Lys Ala Val Lys Pro
            180                 185                 190

Lys Ala Ala Lys Ala Arg Val Thr Pro Lys Thr Ala Lys Pro Lys
        195                 200                 205

Lys Ala Ala Pro Lys Lys Lys
        210             215

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 66

His His His His His His
1               5

<210> SEQ ID NO 67
<211> LENGTH: 7
<212> TYPE: PRT
<213> ORGANISM: Unknown
<220> FEATURE:
<223> OTHER INFORMATION: Description of Unknown:
      TEV protease cleavage sequence

<400> SEQUENCE: 67

Glu Asn Leu Tyr Phe Gln Gly
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Tyr Lys Asp Asp Asp Asp Lys
1               5

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Glu Gln Lys Leu Ile Ser Glu Glu Asp Leu
1               5                   10

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 70

Tyr Pro Tyr Asp Val Pro Asp Tyr Ala
1               5

<210> SEQ ID NO 71
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Tyr Lys Asp Asp Asp Lys Asp Tyr Lys Asp Asp Asp Lys
1               5                   10                  15

Asp Tyr Lys Asp Asp Asp Asp Lys
            20

<210> SEQ ID NO 72
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Gln Lys Leu Ile Ser Glu Glu Asp Leu Glu Gln Lys Leu Ile Ser
1               5                   10                  15

Glu Glu Asp Leu Glu Gln Lys Leu Ile Ser Glu Glu Asp Leu
            20                  25                  30

<210> SEQ ID NO 73
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Tyr Pro Tyr Asp Val Pro Asp Tyr Ala Tyr Pro Tyr Asp Val Pro Asp
1               5                   10                  15

Tyr Ala Tyr Pro Tyr Asp Val Pro Asp Tyr Ala
            20                  25
```